US011350995B2

(12) United States Patent
Finley et al.

(10) Patent No.: US 11,350,995 B2
(45) Date of Patent: Jun. 7, 2022

(54) SURGICAL NAVIGATION SYSTEMS AND METHODS

(71) Applicant: NuVasive, Inc., San Diego, CA (US)

(72) Inventors: Eric Finley, San Diego, CA (US); Mark Covell, Carlsbad, CA (US); D. J. Geiger, San Diego, CA (US); Shannon Murray, Orange County, CA (US); Bryce Nesbitt, San Diego, CA (US); Guy Nimrodi, San Diego, CA (US); Antonio Ubach, Tuscon, AZ (US)

(73) Assignee: NuVasive, Inc., San Diego, CA (US)

(*) Notice: Subject to any disclaimer, the term of this patent is extended or adjusted under 35 U.S.C. 154(b) by 1030 days.

(21) Appl. No.: 15/725,791

(22) Filed: Oct. 5, 2017

(65) Prior Publication Data

US 2018/0092699 A1    Apr. 5, 2018

Related U.S. Application Data

(60) Provisional application No. 62/457,610, filed on Feb. 10, 2017, provisional application No. 62/404,761, filed on Oct. 5, 2016.

(51) Int. Cl.
*A61B 34/20* (2016.01)
*A61B 5/06* (2006.01)
(Continued)

(52) U.S. Cl.
CPC ............. *A61B 34/20* (2016.02); *A61B 5/064* (2013.01); *A61B 5/743* (2013.01); *A61B 17/70* (2013.01);
(Continued)

(58) Field of Classification Search
CPC ............ A61B 90/39; A61B 2090/3991; A61B 2090/3966; A61B 5/064; A61B 5/743;
(Continued)

(56) References Cited

U.S. PATENT DOCUMENTS

| 4,945,914 A | 8/1990 | Allen |
| 5,211,164 A | 5/1993 | Allen |

(Continued)

FOREIGN PATENT DOCUMENTS

| AU | 2013204941 B2 | 10/2015 |
| CN | 101904770 | 12/2010 |

(Continued)

OTHER PUBLICATIONS

Schlenzka et al., Computer Assisted Spine Surgery, Eur Spine J (2000) 9 (Suppl 1) : S56-S64.
(Continued)

*Primary Examiner* — Colin T. Sakamoto
(74) *Attorney, Agent, or Firm* — Merchant & Gould P.C.

(57) ABSTRACT

A system, including various apparatus and methods, for surgical navigation is provided. The system is configured to track the spine of a patient by capturing images via one or more cameras. The cameras are configured to capture images of one or more arrays. The system transmits the images to a computer system. The one or more arrays are releasably secured with the spine of the patient, such as by a spine pin or a spine clamp. The system can determine the spatial position and orientation of relevant anatomical features, implants, and instruments using and processing the captured images.

19 Claims, 45 Drawing Sheets

(51) Int. Cl.

| | | |
|---|---|---|
| *A61B 34/00* | (2016.01) | |
| *A61B 17/70* | (2006.01) | |
| *A61B 90/00* | (2016.01) | |
| *A61B 34/10* | (2016.01) | |
| *A61B 5/00* | (2006.01) | |
| A61B 17/56 | (2006.01) | |
| A61B 17/17 | (2006.01) | |

(52) U.S. Cl.
CPC ...... *A61B 17/7047* (2013.01); *A61B 17/7062* (2013.01); *A61B 17/7074* (2013.01); *A61B 17/7083* (2013.01); *A61B 34/10* (2016.02); *A61B 34/25* (2016.02); *A61B 90/36* (2016.02); *A61B 90/37* (2016.02); *A61B 90/39* (2016.02); A61B 5/4893 (2013.01); A61B 17/1757 (2013.01); A61B 2017/564 (2013.01); A61B 2034/102 (2016.02); A61B 2034/107 (2016.02); A61B 2034/2046 (2016.02); A61B 2034/2055 (2016.02); A61B 2034/2057 (2016.02); A61B 2034/252 (2016.02); A61B 2034/254 (2016.02); A61B 2034/258 (2016.02); A61B 2090/365 (2016.02); A61B 2090/371 (2016.02); A61B 2090/372 (2016.02); A61B 2090/376 (2016.02); A61B 2090/3764 (2016.02); A61B 2090/3937 (2016.02); A61B 2090/3966 (2016.02); A61B 2090/3983 (2016.02); A61B 2090/3991 (2016.02)

(58) Field of Classification Search
CPC ... A61B 5/4893; A61B 17/1757; A61B 17/70; A61B 17/7047; A61B 17/7062; A61B 17/7074; A61B 17/7083; A61B 2017/564; A61B 90/36; A61B 90/37; A61B 2090/365; A61B 2090/371; A61B 2090/372; A61B 2090/376; A61B 2090/3764; A61B 2090/3937; A61B 2090/3983; A61B 34/10; A61B 34/20; A61B 34/25; A61B 2034/102; A61B 2034/107; A61B 2034/252; A61B 2034/254; A61B 2034/258; A61B 2034/2046; A61B 2034/2055; A61B 2034/2057
USPC ........................................................ 600/424
See application file for complete search history.

(56) References Cited

U.S. PATENT DOCUMENTS

| | | | |
|---|---|---|---|
| 5,383,454 A | 1/1995 | Bucholz | |
| 5,389,101 A | 2/1995 | Heilbrun | |
| 5,603,318 A | 2/1997 | Heilbrun | |
| 5,682,886 A | 11/1997 | Delp | |
| 5,799,055 A | 8/1998 | Peshkin | |
| 5,836,954 A | 11/1998 | Heilbrun | |
| 5,871,018 A | 2/1999 | Delp | |
| 5,880,976 A | 3/1999 | Digioia | |
| 5,930,384 A | 7/1999 | Guillemaud | |
| 5,951,475 A | 9/1999 | Gueziec | |
| 5,995,738 A | 11/1999 | Digioia | |
| 6,002,859 A | 12/1999 | Digioia | |
| 6,025,411 A | 2/2000 | Wong | |
| 6,049,582 A | 4/2000 | Navab | |
| 6,151,404 A | 11/2000 | Pieper | |
| 6,190,395 B1 | 2/2001 | Williams | |
| 6,273,896 B1 | 8/2001 | Franck | |
| 6,285,902 B1 | 9/2001 | Kienzle | |
| 6,289,235 B1 | 9/2001 | Webber | |
| 6,314,310 B1 * | 11/2001 | Ben-Haim | A61B 90/36 600/424 |
| 6,359,960 B1 | 3/2002 | Wahl | |
| 6,396,939 B1 | 5/2002 | Hu | |
| 6,405,072 B1 | 6/2002 | Cosman | |
| 6,470,207 B1 | 10/2002 | Simon | |
| 6,490,477 B1 | 12/2002 | Zylka | |
| 6,527,443 B1 | 3/2003 | Vilsmeier | |
| 6,533,455 B2 | 3/2003 | Graumann | |
| 6,533,737 B1 | 3/2003 | Brosseau | |
| 6,535,756 B1 | 3/2003 | Simon | |
| 6,556,857 B1 | 4/2003 | Estes | |
| 6,584,174 B2 | 6/2003 | Schubert | |
| 6,606,091 B2 | 8/2003 | Liang | |
| 6,608,916 B1 | 8/2003 | Wei | |
| 6,608,917 B1 | 8/2003 | Wei | |
| 6,609,022 B2 | 8/2003 | Vilsmeier | |
| 6,640,128 B2 | 10/2003 | Vilsmeier | |
| 6,697,664 B2 | 2/2004 | Kienzle | |
| 6,714,629 B2 | 3/2004 | Vilsmeier | |
| 6,715,918 B2 | 4/2004 | Mitschke | |
| 6,725,079 B2 | 4/2004 | Zuk | |
| 6,772,002 B2 | 8/2004 | Schmidt | |
| 6,796,988 B2 | 9/2004 | Melkent | |
| 6,801,643 B2 | 10/2004 | Pieper | |
| 6,808,526 B1 * | 10/2004 | Magerl | A61B 17/685 606/308 |
| 6,810,278 B2 | 10/2004 | Webber | |
| 6,810,280 B2 | 10/2004 | Strobel | |
| 6,851,855 B2 | 2/2005 | Mitschke | |
| 6,873,867 B2 | 3/2005 | Vilsmeier | |
| 6,877,239 B2 | 4/2005 | Leitner | |
| 6,912,265 B2 | 6/2005 | Hebecker | |
| 6,920,347 B2 | 7/2005 | Simon | |
| 6,940,941 B2 | 9/2005 | Gregerson | |
| 6,947,786 B2 | 9/2005 | Simon | |
| 6,993,374 B2 | 1/2006 | Sasso | |
| 6,996,487 B2 | 2/2006 | Jutras | |
| 7,001,045 B2 | 2/2006 | Gregerson | |
| 7,010,151 B2 | 3/2006 | Wei | |
| 7,035,371 B2 | 4/2006 | Boese | |
| RE39,133 E | 6/2006 | Clayton | |
| 7,106,825 B2 | 9/2006 | Gregerson | |
| 7,108,421 B2 | 9/2006 | Gregerson | |
| 7,123,760 B2 | 10/2006 | Mullick | |
| 7,139,418 B2 | 11/2006 | Abovitz | |
| 7,142,633 B2 | 11/2006 | Eberhard | |
| 7,149,333 B2 | 12/2006 | Pieper | |
| 7,188,998 B2 | 3/2007 | Gregerson | |
| 7,197,170 B2 | 3/2007 | Dwyer | |
| 7,218,766 B2 | 5/2007 | Eberhard | |
| 7,233,820 B2 | 6/2007 | Gilboa | |
| 7,275,218 B2 | 9/2007 | Petrella | |
| 7,324,660 B2 | 1/2008 | Oosawa | |
| RE40,176 E | 3/2008 | Peshkin | |
| 7,409,033 B2 | 8/2008 | Zhu | |
| 7,426,256 B2 | 9/2008 | Rasche | |
| 7,427,200 B2 | 9/2008 | Noble | |
| 7,519,415 B2 | 4/2009 | Mitschke | |
| 7,522,779 B2 | 4/2009 | Fu | |
| 7,542,791 B2 | 6/2009 | Mire | |
| 7,561,733 B2 | 7/2009 | Vilsmeier | |
| 7,567,834 B2 | 7/2009 | Clayton | |
| 7,570,791 B2 | 8/2009 | Frank | |
| 7,606,613 B2 | 10/2009 | Simon | |
| 7,630,753 B2 | 12/2009 | Simon | |
| 7,634,122 B2 | 12/2009 | Bertram | |
| 7,660,623 B2 | 2/2010 | Hunter | |
| 7,661,881 B2 | 2/2010 | Gregerson | |
| 7,697,972 B2 | 4/2010 | Verard | |
| 7,712,961 B2 | 5/2010 | Hoerndler | |
| 7,715,605 B2 | 5/2010 | Verre | |
| 7,734,329 B2 | 6/2010 | Boese | |
| 7,751,865 B2 | 7/2010 | Jascob et al. | |
| 7,760,926 B2 | 7/2010 | Boese | |
| 7,776,000 B2 | 8/2010 | Schaffrath | |
| 7,797,030 B2 | 9/2010 | Lahm | |
| 7,803,164 B2 | 9/2010 | Gielen | |
| 7,822,244 B2 | 10/2010 | Blumhofer | |

(56) References Cited

U.S. PATENT DOCUMENTS

| | | |
|---|---|---|
| 7,831,292 B2 | 11/2010 | Quaid |
| 7,831,294 B2 | 11/2010 | Viswanathan |
| 7,835,497 B2 | 11/2010 | Haras |
| 7,835,561 B2 | 11/2010 | Meyer |
| 7,835,778 B2 | 11/2010 | Foley |
| 7,835,784 B2 | 11/2010 | Mire |
| 7,840,253 B2 | 11/2010 | Tremblay |
| 7,853,305 B2 | 12/2010 | Simon |
| 7,879,045 B2 | 2/2011 | Gielen |
| 7,883,545 B2 | 2/2011 | Tuma |
| RE42,194 E | 3/2011 | Foley |
| RE42,226 E | 3/2011 | Foley |
| 7,903,779 B2 | 3/2011 | Gregerson |
| 7,903,859 B2 | 3/2011 | Boeing |
| 7,922,391 B2 | 4/2011 | Essenreiter |
| 7,925,328 B2 | 4/2011 | Urquhart |
| 7,953,471 B2 | 5/2011 | Clayton |
| 7,957,831 B2 | 6/2011 | Isaacs |
| 7,965,811 B1 | 6/2011 | Gregerson |
| 7,974,677 B2 | 7/2011 | Mire |
| 7,987,001 B2 | 7/2011 | Teichman |
| 7,995,811 B2 | 8/2011 | Feuerlein |
| 7,995,819 B2 | 8/2011 | Vaillant |
| 7,996,064 B2 | 8/2011 | Simon |
| 8,005,284 B2 | 8/2011 | Sakaguchi |
| 8,010,177 B2 | 8/2011 | Csavoy |
| 8,010,180 B2 | 8/2011 | Quaid |
| 8,014,575 B2 | 9/2011 | Weiss |
| 8,018,456 B2 | 9/2011 | Blumhofer |
| 8,023,706 B2 | 9/2011 | Witte |
| 8,031,922 B2 | 10/2011 | Haimerl |
| 8,036,441 B2 | 10/2011 | Frank |
| 8,041,089 B2 | 10/2011 | Drumm |
| 8,046,051 B2 | 10/2011 | Homan |
| 8,050,483 B2 | 11/2011 | Boese |
| 8,055,046 B2 | 11/2011 | Feilkas |
| 8,094,906 B2 | 1/2012 | Porat |
| 8,098,909 B2 | 1/2012 | Hibbard |
| 8,104,957 B2 | 1/2012 | Maier |
| 8,104,958 B2 | 1/2012 | Weiser |
| 8,108,025 B2 | 1/2012 | Csavoy |
| 8,112,292 B2 | 2/2012 | Simon |
| 8,126,111 B2 | 2/2012 | Uhde |
| 8,126,535 B2 | 2/2012 | Maier |
| RE43,328 E | 4/2012 | Foley |
| 8,150,494 B2 | 4/2012 | Simon |
| 8,165,366 B2 | 4/2012 | Haimerl |
| 8,170,310 B2 | 5/2012 | Woo |
| 8,175,349 B2 | 5/2012 | Jerebko |
| 8,175,365 B2 | 5/2012 | Edlauer |
| 8,199,986 B2 | 6/2012 | Wang |
| 8,218,843 B2 | 7/2012 | Edlauer |
| 8,218,846 B2 | 7/2012 | Trumer |
| 8,233,690 B2 | 7/2012 | Ng |
| 8,233,963 B2 | 7/2012 | Hartmann |
| 8,238,631 B2 | 8/2012 | Hartmann |
| 8,239,001 B2 | 8/2012 | Verard |
| 8,244,064 B2 | 8/2012 | Boese |
| 8,244,495 B2 | 8/2012 | Goldbach |
| 8,285,023 B2 | 10/2012 | Tsujii |
| 8,295,909 B2 | 10/2012 | Goldbach |
| 8,311,611 B2 | 11/2012 | Csavoy |
| 8,320,991 B2 | 11/2012 | Jascob |
| 8,320,992 B2 | 11/2012 | Frenkel |
| 8,328,793 B2 | 12/2012 | Birkenbach |
| 8,335,357 B2 | 12/2012 | Sakaguchi |
| 8,335,364 B2 | 12/2012 | Osmundson |
| 8,340,751 B2 | 12/2012 | Markowitz |
| 8,374,673 B2 | 2/2013 | Adcox |
| 8,374,678 B2 | 2/2013 | Graumann |
| 8,423,124 B2 | 4/2013 | Kiraly |
| 8,442,622 B2 | 5/2013 | Wang |
| RE44,305 E | 6/2013 | Foley |
| 8,463,010 B2 | 6/2013 | Batman |
| 8,463,013 B2 | 6/2013 | Ohishi |
| 8,467,851 B2 | 6/2013 | Mire |
| 8,467,852 B2 | 6/2013 | Csavoy |
| 8,472,691 B2 | 6/2013 | Furst |
| 8,483,434 B2 | 7/2013 | Buehner |
| 8,494,242 B2 | 7/2013 | Kitamura |
| 8,494,613 B2 | 7/2013 | Markowitz |
| 8,494,614 B2 | 7/2013 | Markowitz |
| 8,503,745 B2 | 8/2013 | Simon |
| 8,509,502 B2 | 8/2013 | Porat |
| 8,538,539 B2 | 9/2013 | Gharib et al. |
| 8,548,563 B2 | 10/2013 | Simon |
| 8,548,579 B2 | 10/2013 | Gharib et al. |
| 8,549,888 B2 | 10/2013 | Isaacs |
| 8,550,994 B2 | 10/2013 | Miles et al. |
| 8,551,024 B2 | 10/2013 | Gruenschlaeger |
| 8,556,808 B2 | 10/2013 | Miles et al. |
| 8,562,211 B2 | 10/2013 | Helm |
| 8,562,521 B2 | 10/2013 | Miles et al. |
| 8,577,114 B2 | 11/2013 | Faul |
| 8,591,432 B2 | 11/2013 | Pimenta et al. |
| 8,594,407 B2 | 11/2013 | Jerebko |
| 8,597,211 B2 | 12/2013 | Berlinger |
| 8,602,982 B2 | 12/2013 | Miles et al. |
| 8,628,469 B2 | 1/2014 | Miles et al. |
| 8,634,897 B2 | 1/2014 | Simon |
| 8,634,904 B2 | 1/2014 | Kaula et al. |
| 8,644,570 B2 | 2/2014 | Hartmann |
| 8,644,573 B2 | 2/2014 | Riddell |
| 8,663,100 B2 | 3/2014 | Miles et al. |
| 8,672,840 B2 | 3/2014 | Miles et al. |
| 8,678,647 B2 | 3/2014 | Gregerson |
| 8,679,006 B2 | 3/2014 | Miles et al. |
| 8,685,093 B2 | 4/2014 | Anderson |
| 8,688,409 B2 | 4/2014 | Tuma |
| 8,694,075 B2 | 4/2014 | Groszmann |
| 8,696,559 B2 | 4/2014 | Miles et al. |
| 8,705,829 B2 | 4/2014 | Frank |
| 8,708,899 B2 | 4/2014 | Miles et al. |
| 8,725,235 B2 | 5/2014 | Gielen |
| 8,734,432 B2 | 5/2014 | Tuma |
| 8,737,567 B2 | 5/2014 | Shah |
| 8,737,708 B2 | 5/2014 | Hartmann |
| 8,738,123 B2 | 5/2014 | Gharib et al. |
| 8,744,819 B2 | 6/2014 | Rodriguez Y Baena |
| 8,747,307 B2 | 6/2014 | Miles et al. |
| 8,750,582 B2 | 6/2014 | Boese |
| 8,753,271 B1 | 6/2014 | Miles et al. |
| 8,761,484 B2 | 6/2014 | Tsujii |
| 8,764,649 B2 | 7/2014 | Miles et al. |
| 8,767,910 B2 | 7/2014 | Shi |
| 8,768,029 B2 | 7/2014 | Helm |
| 8,768,450 B2 | 7/2014 | Gharib et al. |
| 8,784,330 B1 | 7/2014 | Scholl et al. |
| 8,798,357 B2 | 8/2014 | Sinha |
| 8,805,042 B2 | 8/2014 | Weiss |
| 8,811,699 B2 | 8/2014 | Lu |
| 8,821,396 B1 | 9/2014 | Miles et al. |
| 8,831,303 B2 | 9/2014 | Villain |
| 8,831,324 B2 | 9/2014 | Penenberg |
| 8,842,893 B2 | 9/2014 | Teichman |
| 8,845,656 B2 | 9/2014 | Skakoon |
| 8,848,999 B2 | 9/2014 | Boese |
| 8,885,899 B2 | 11/2014 | Illes |
| 8,886,286 B2 | 11/2014 | Graumann |
| 8,891,847 B2 | 11/2014 | Helm |
| 8,897,514 B2 | 11/2014 | Feikas |
| 8,908,918 B2 | 12/2014 | Daon |
| 8,908,950 B2 | 12/2014 | Barfuss |
| 8,938,113 B2 | 1/2015 | Kovalan |
| 8,938,282 B2 | 1/2015 | Daon |
| 8,942,450 B2 | 1/2015 | Riddell |
| 8,942,455 B2 | 1/2015 | Chou |
| 8,942,801 B2 | 1/2015 | Miles et al. |
| 8,945,004 B2 | 2/2015 | Miles et al. |
| 8,948,472 B2 | 2/2015 | Wohlgemuth |
| 8,956,283 B2 | 2/2015 | Miles et al. |
| 8,958,614 B2 | 2/2015 | Zhan |
| 8,971,495 B2 | 3/2015 | Shah |
| 8,971,606 B2 | 3/2015 | Chaoui |

(56) References Cited

U.S. PATENT DOCUMENTS

| | | |
|---|---|---|
| 8,977,352 B2 | 3/2015 | Gharib et al. |
| 8,989,866 B2 | 3/2015 | Gharib et al. |
| 8,992,580 B2 | 3/2015 | Bar |
| RE45,484 E | 4/2015 | Foley |
| 9,002,076 B2 | 4/2015 | Khadem |
| 9,020,235 B2 | 4/2015 | Krishnan |
| RE45,509 E | 5/2015 | Foley |
| 9,037,250 B2 | 5/2015 | Kaula et al. |
| 9,042,513 B2 | 5/2015 | Shi |
| 9,044,269 B2 | 6/2015 | Woerlein |
| 9,066,751 B2 | 6/2015 | Sasso |
| 9,066,755 B1 | 6/2015 | Jacobs |
| 9,084,888 B2 | 7/2015 | Poulsen |
| 9,095,375 B2 | 8/2015 | Haimerl |
| 9,098,899 B2 | 8/2015 | Waechter-Stehle |
| 9,098,912 B2 | 8/2015 | Kriston |
| 9,105,085 B2 | 8/2015 | Bond |
| 9,122,950 B2 | 9/2015 | Han |
| 9,125,680 B2 | 9/2015 | Kostrzewski |
| 9,135,706 B2 | 9/2015 | Zagorchev |
| 9,138,204 B2 | 9/2015 | Koenig |
| 9,142,020 B2 | 9/2015 | Deguise |
| 9,152,854 B2 | 10/2015 | Lee |
| 9,161,799 B2 | 10/2015 | Benson |
| 9,183,628 B2 | 11/2015 | Wang |
| 9,196,035 B2 | 11/2015 | Weiss |
| 9,196,091 B2 | 11/2015 | Papageorgiou |
| 9,198,707 B2 | 12/2015 | Mckay |
| 9,198,737 B2 | 12/2015 | Daon |
| 9,220,573 B2 | 12/2015 | Kendrick |
| 9,224,204 B2 | 12/2015 | Vija |
| 9,224,229 B2 | 12/2015 | Panter |
| 9,237,931 B2 | 1/2016 | Gowda |
| 9,240,046 B2 | 1/2016 | Carrell |
| 9,241,634 B2 | 1/2016 | Wang |
| 9,241,657 B2 | 1/2016 | Vollmer |
| 9,256,916 B2 | 2/2016 | Omi |
| 9,256,965 B2 | 2/2016 | Han |
| 9,265,463 B1 | 2/2016 | Hipp |
| 9,265,589 B2 | 2/2016 | Hartmann |
| 9,280,815 B2 | 3/2016 | Slutsky |
| 9,286,688 B2 | 3/2016 | Reda |
| 9,289,270 B2 | 3/2016 | Gielen |
| 9,299,146 B2 | 3/2016 | Wang |
| 9,305,354 B2 | 4/2016 | Burlon |
| 9,311,335 B2 | 4/2016 | Simon |
| 9,317,926 B2 | 4/2016 | Wang |
| 9,367,917 B2 | 6/2016 | Eriksson |
| 9,401,020 B1 | 7/2016 | Li |
| 9,406,122 B2 | 8/2016 | Hladuvka |
| 9,406,124 B2 | 8/2016 | Merckx |
| 9,408,584 B2 | 8/2016 | Major |
| 9,418,468 B2 | 8/2016 | Paragios |
| 9,439,623 B2 | 9/2016 | Frank |
| 9,443,346 B2 | 9/2016 | Ikits |
| 9,468,412 B2 | 10/2016 | Hamadeh |
| 9,486,295 B2 | 11/2016 | Vilsmeier |
| 9,498,182 B2 | 11/2016 | Case |
| 9,504,531 B2 | 11/2016 | Teichman |
| 9,508,149 B2 | 11/2016 | Simon |
| 9,642,560 B2 | 5/2017 | Schubert |
| 9,652,591 B2 | 5/2017 | Moctezuma De La Barrera et al. |
| 9,668,820 B2 | 6/2017 | Neubauer |
| 9,675,424 B2 | 6/2017 | Jascob |
| 9,681,925 B2 | 6/2017 | Azar |
| 9,697,600 B2 | 7/2017 | Keuchel |
| 9,717,442 B2 | 8/2017 | Jacobsen |
| 9,717,898 B2 | 8/2017 | Thompson-Nauman |
| 9,724,165 B2 | 8/2017 | Arata |
| 9,775,681 B2 | 10/2017 | Quaid |
| 9,820,818 B2 | 11/2017 | Malackowski |
| 9,943,369 B2 | 4/2018 | Heigl |
| 9,974,615 B2 | 5/2018 | Woerlein |
| 10,016,243 B2 | 7/2018 | Esterberg |
| 10,055,848 B2 | 8/2018 | Gassner |
| 10,105,168 B2 | 10/2018 | Blau |
| 10,143,839 B1 | 12/2018 | Christie |
| 10,165,981 B2 | 1/2019 | Schoepp |
| 10,179,031 B2 | 1/2019 | Haimerl |
| 10,191,615 B2 | 1/2019 | Helm |
| 10,297,042 B2 | 5/2019 | Berlinger |
| 10,357,315 B2 | 7/2019 | Otto |
| 10,363,102 B2 | 7/2019 | Abovitz |
| 10,388,066 B2 | 8/2019 | Averbuch |
| 10,413,752 B2 | 9/2019 | Berlinger |
| 10,456,204 B2 | 10/2019 | Park |
| 10,478,254 B2 | 11/2019 | Krimsky |
| 10,485,617 B2 | 11/2019 | Crawford |
| 10,492,868 B2 | 12/2019 | Hartmann |
| 10,492,875 B2 | 12/2019 | Janik |
| 10,512,522 B2 | 12/2019 | Verard |
| 10,531,814 B2 | 1/2020 | Reddy |
| 10,531,925 B2 | 1/2020 | Malackowski |
| 10,531,926 B2 | 1/2020 | Roessler |
| 10,561,345 B2 | 2/2020 | Brack |
| 10,575,755 B2 | 3/2020 | Breisacher |
| 10,653,497 B2 | 5/2020 | Crawford |
| 10,660,711 B2 | 5/2020 | Moctezuma De La Barrera et al. |
| 10,667,864 B2 | 6/2020 | Feilkas |
| 10,667,868 B2 | 6/2020 | Malackowski |
| 10,675,094 B2 | 6/2020 | Crawford |
| 10,758,315 B2 | 9/2020 | Johnson |
| 10,799,298 B2 | 10/2020 | Crawford |
| 10,813,704 B2 | 10/2020 | Kostrzewski |
| 10,828,113 B2 | 11/2020 | Melkent |
| 2001/0044624 A1 | 11/2001 | Seraj |
| 2004/0147837 A1 | 7/2004 | Macaulay |
| 2004/0220581 A1 | 11/2004 | Foley |
| 2005/0021031 A1 | 1/2005 | Foley |
| 2005/0277832 A1* | 12/2005 | Foley ............... A61B 34/20 600/426 |
| 2006/0036189 A1 | 2/2006 | Martinelli |
| 2006/0094958 A1 | 5/2006 | Marquart |
| 2007/0270866 A1* | 11/2007 | von Jako .......... A61B 17/3423 606/86 R |
| 2007/0293721 A1 | 12/2007 | Gilboa |
| 2008/0004516 A1* | 1/2008 | DiSilvestro ........ A61B 90/36 600/407 |
| 2008/0118135 A1 | 5/2008 | Averbuch |
| 2008/0154125 A1* | 6/2008 | Maier ................ G16H 50/50 600/424 |
| 2008/0200794 A1 | 8/2008 | Teichman |
| 2008/0255442 A1 | 10/2008 | Ashby |
| 2008/0262342 A1 | 10/2008 | Averbruch |
| 2008/0287781 A1 | 11/2008 | Revie |
| 2008/0294265 A1* | 11/2008 | Warkentine ......... A61B 34/20 623/22.4 |
| 2009/0264738 A1 | 10/2009 | Markowitz |
| 2009/0264751 A1 | 10/2009 | Markowitz |
| 2009/0297001 A1 | 12/2009 | Markowitz |
| 2010/0030219 A1 | 2/2010 | Lerner |
| 2010/0034449 A1 | 2/2010 | Averbuch |
| 2010/0046718 A1* | 2/2010 | Weiser ................ A61B 6/583 378/163 |
| 2010/0152571 A1 | 6/2010 | Hartmann |
| 2010/0172557 A1 | 7/2010 | Richard |
| 2010/0192961 A1 | 8/2010 | Amiot |
| 2010/0228117 A1 | 9/2010 | Hartmann |
| 2010/0249576 A1 | 9/2010 | Askarinya |
| 2010/0249581 A1 | 9/2010 | Mccombs |
| 2011/0004224 A1 | 1/2011 | Daigneault |
| 2011/0004259 A1 | 1/2011 | Stallings |
| 2011/0015521 A1 | 1/2011 | Faul |
| 2011/0034796 A1* | 2/2011 | Ma ..................... A61B 5/4312 600/407 |
| 2011/0237935 A1 | 9/2011 | Kalpin |
| 2011/0257653 A1 | 10/2011 | Hughes et al. |
| 2012/0197108 A1 | 8/2012 | Hartmann |
| 2012/0197110 A1 | 8/2012 | Hartmann |
| 2012/0220859 A1 | 8/2012 | Amiot |
| 2012/0221017 A1 | 8/2012 | Bonutti |
| 2012/0232377 A1 | 9/2012 | Nottmeier |
| 2012/0323247 A1 | 12/2012 | Bettenga |
| 2012/0330135 A1 | 12/2012 | Millahn |

(56) References Cited

U.S. PATENT DOCUMENTS

| | | |
|---|---|---|
| 2013/0102878 A1 | 4/2013 | Burg |
| 2013/0131504 A1 | 5/2013 | Daon |
| 2013/0131505 A1 | 5/2013 | Daon |
| 2013/0137972 A1 | 5/2013 | Malackowski |
| 2013/0150863 A1 | 6/2013 | Baumgartner |
| 2013/0218216 A1 | 8/2013 | Mast |
| 2013/0303890 A1 | 11/2013 | Duindam |
| 2013/0317351 A1 | 11/2013 | Case |
| 2013/0317363 A1 | 11/2013 | Case |
| 2013/0331686 A1 | 12/2013 | Freysinger |
| 2013/0345718 A1* | 12/2013 | Crawford ............ A61B 5/066 606/130 |
| 2014/0005527 A1* | 1/2014 | Nagarkar ............ A61B 5/05 600/424 |
| 2014/0024927 A1 | 1/2014 | Piferi |
| 2014/0039517 A1 | 2/2014 | Bowling |
| 2014/0049629 A1* | 2/2014 | Siewerdsen ........ A61B 34/20 348/77 |
| 2014/0051980 A1 | 2/2014 | Frigg |
| 2014/0148692 A1 | 5/2014 | Hartmann |
| 2014/0171962 A1 | 6/2014 | Kang |
| 2015/0025367 A1 | 1/2015 | Malackowski |
| 2015/0031985 A1 | 1/2015 | Reddy |
| 2015/0073269 A1 | 3/2015 | Stopek |
| 2015/0094736 A1 | 4/2015 | Malackowski |
| 2015/0100091 A1* | 4/2015 | Tohmeh ............ A61B 17/7083 606/279 |
| 2015/0132720 A1 | 5/2015 | Daon |
| 2015/0147714 A1 | 5/2015 | Daon |
| 2015/0150641 A1 | 6/2015 | Daon |
| 2015/0150692 A1 | 6/2015 | Lye |
| 2015/0182296 A1 | 7/2015 | Daon |
| 2015/0209119 A1 | 7/2015 | Theodore |
| 2016/0120609 A1 | 5/2016 | Jacobsen |
| 2016/0128789 A1 | 5/2016 | Kostrzewski |
| 2016/0174873 A1 | 6/2016 | Greenburg |
| 2016/0220320 A1 | 8/2016 | Crawford |
| 2016/0278864 A1 | 9/2016 | Paitel |
| 2016/0278875 A1 | 9/2016 | Crawford |
| 2016/0310218 A1 | 10/2016 | Ruckel |
| 2016/0354160 A1 | 12/2016 | Crowley |
| 2016/0371883 A1 | 12/2016 | Merkine |
| 2017/0007334 A1 | 1/2017 | Crawford |
| 2017/0020491 A1 | 1/2017 | Ogawa |
| 2017/0020630 A1 | 1/2017 | Johnson |
| 2017/0112411 A1 | 4/2017 | Costello |
| 2017/0119339 A1 | 5/2017 | Johnson |
| 2017/0165006 A1* | 6/2017 | Woods ............ A61B 90/39 |
| 2017/0172669 A1 | 6/2017 | Berkowitz |
| 2017/0231702 A1 | 8/2017 | Crawford |
| 2017/0239003 A1 | 8/2017 | Crawford |
| 2017/0239007 A1 | 8/2017 | Crawford |
| 2017/0245951 A1 | 8/2017 | Crawford |
| 2017/0311880 A1 | 11/2017 | Jacobsen |
| 2017/0348061 A1 | 12/2017 | Joshi |
| 2018/0153622 A1 | 6/2018 | Dohmen |
| 2018/0200002 A1 | 7/2018 | Kostrzewski |
| 2018/0217734 A1 | 8/2018 | Koenig |
| 2018/0228623 A1 | 8/2018 | Benson |
| 2018/0263714 A1 | 9/2018 | Kostrzewski |
| 2018/0296283 A1 | 10/2018 | Crawford |
| 2018/0325608 A1 | 11/2018 | Kang |
| 2018/0333207 A1 | 11/2018 | Moctezuma De La Barrera |
| 2018/0367765 A1 | 12/2018 | Vilsmeier |
| 2019/0021795 A1 | 1/2019 | Crawford |
| 2019/0021800 A1 | 1/2019 | Crawford |
| 2019/0029765 A1 | 1/2019 | Crawford |
| 2019/0105116 A1 | 4/2019 | Johnson |
| 2019/0239961 A1 | 8/2019 | Birenbaum |
| 2019/0240489 A1 | 8/2019 | Tsay |
| 2019/0269467 A1 | 9/2019 | Forsyth |
| 2019/0274765 A1 | 9/2019 | Crawford |
| 2019/0321108 A1 | 10/2019 | Ghanam |
| 2019/0328461 A1 | 10/2019 | Kemp |
| 2019/0357986 A1 | 11/2019 | Morgan |
| 2019/0374289 A1 | 12/2019 | Stawiaski |
| 2020/0030040 A1 | 1/2020 | Kostrzewski |
| 2020/0107877 A1 | 4/2020 | Koblish |
| 2020/0155243 A1 | 5/2020 | Crawford |
| 2020/0170723 A1 | 6/2020 | Crawford |
| 2020/0188032 A1 | 6/2020 | Komp |
| 2020/0188033 A1 | 6/2020 | Komp |
| 2020/0237444 A1 | 7/2020 | Snyder |
| 2020/0237445 A1 | 7/2020 | Snyder |
| 2020/0297251 A1 | 9/2020 | Herrmann |
| 2020/0297426 A1 | 9/2020 | Cameron |
| 2020/0297427 A1 | 9/2020 | Cameron |
| 2020/0297428 A1 | 9/2020 | Schöpp |
| 2020/0297435 A1 | 9/2020 | Cameron |
| 2020/0305979 A1 | 10/2020 | Crawford |
| 2020/0315737 A1 | 10/2020 | Crawford |
| 2020/0323609 A1 | 10/2020 | Johnson |
| 2020/0323654 A1 | 10/2020 | Marrapode |
| 2020/0330162 A1 | 10/2020 | Gamm |
| 2020/0345424 A1 | 11/2020 | Wolfsberger |
| 2020/0345430 A1 | 11/2020 | Junio |

FOREIGN PATENT DOCUMENTS

| | | | |
|---|---|---|---|
| DE | 10114910 | | 10/2002 |
| DE | 10306793 A1 | | 12/2003 |
| EP | 1669027 A1 | | 6/2006 |
| EP | 1872737 | | 10/2011 |
| JP | 2014524776 A1 | | 9/2014 |
| WO | 1999015097 | | 4/1999 |
| WO | 1999029253 | | 6/1999 |
| WO | WO-2004075768 A2 * | 9/2004 | ............ A61B 34/20 |
| WO | 2008064126 A2 | | 5/2008 |
| WO | 2012173890 A2 | | 12/2012 |
| WO | 2012177475 A1 | | 12/2012 |
| WO | 2016044934 | | 3/2016 |

OTHER PUBLICATIONS

Stryker, Integrated Spine Navigation Solution (2016).
Ziehm NaviPort, 3D Interface for Image-Guided Navigation, Ziehm Imaging, 280943 Sep. 2016.

* cited by examiner

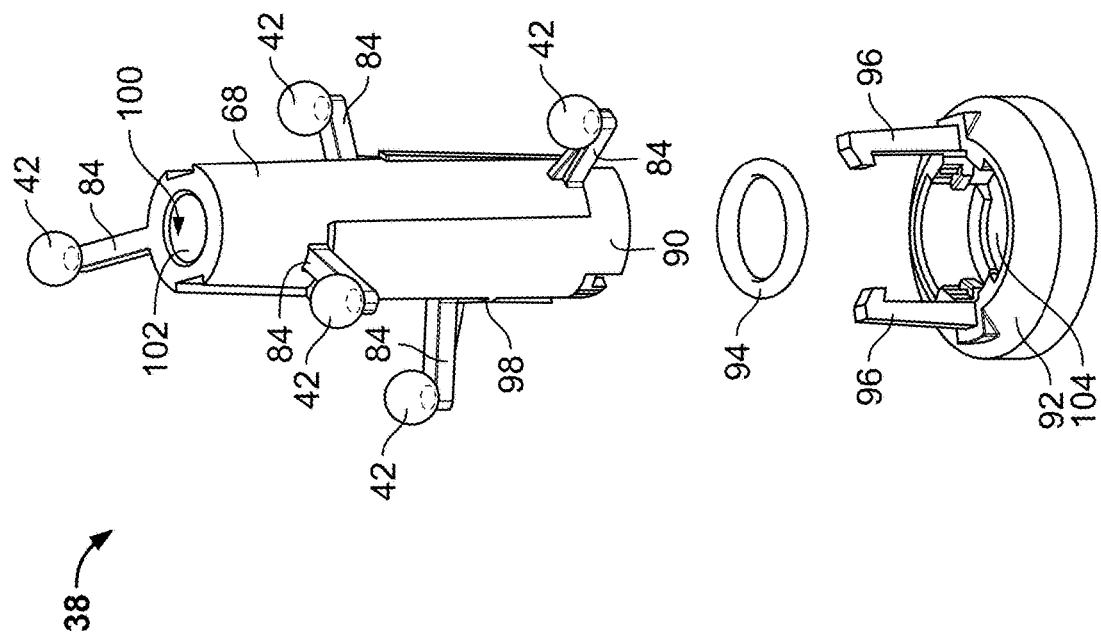
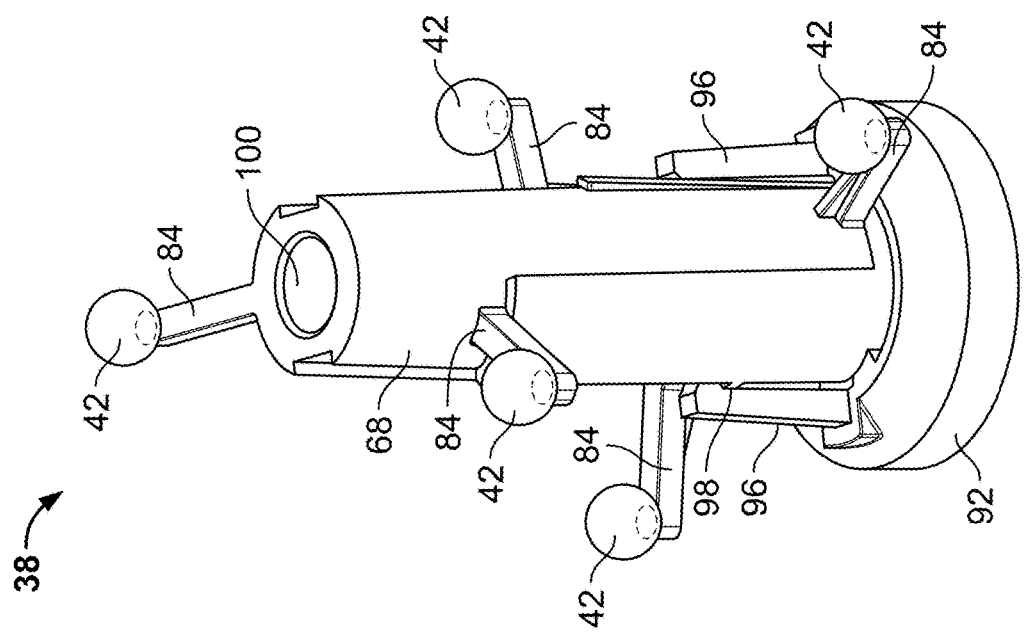

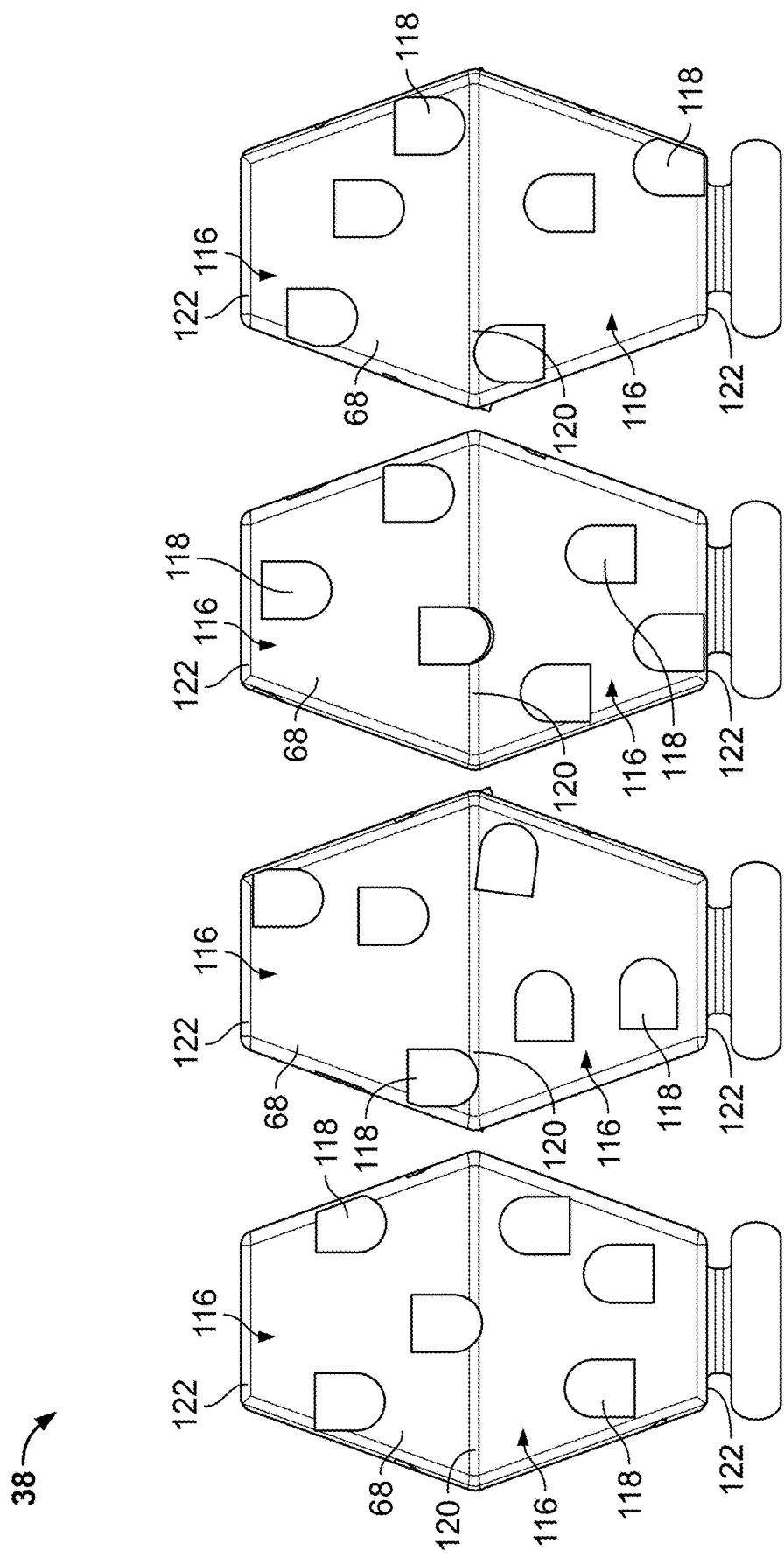

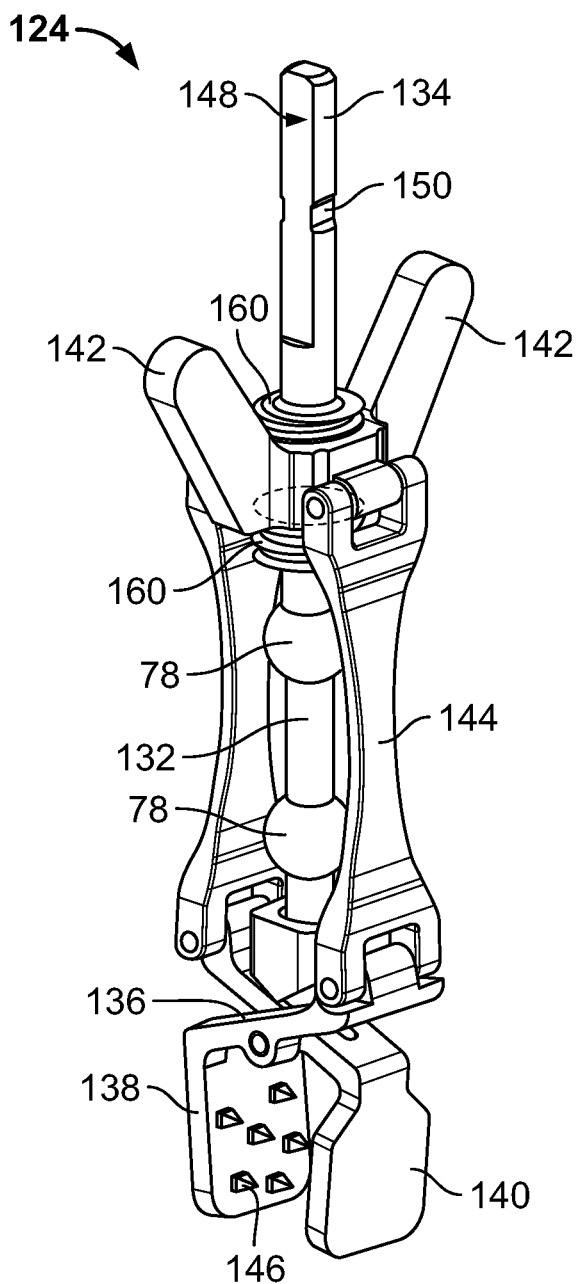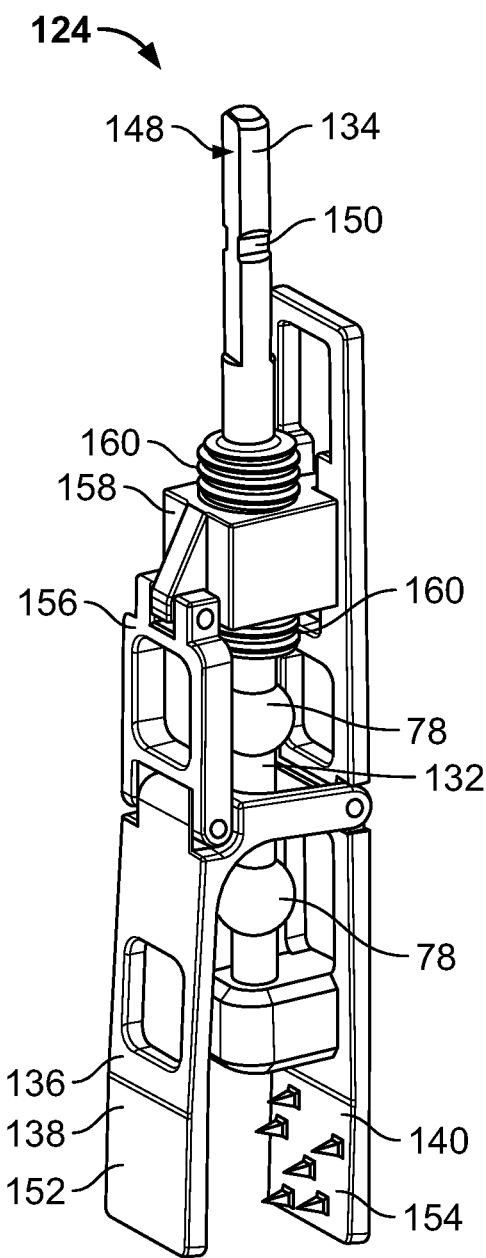
FIG. 8D
FIG. 8E

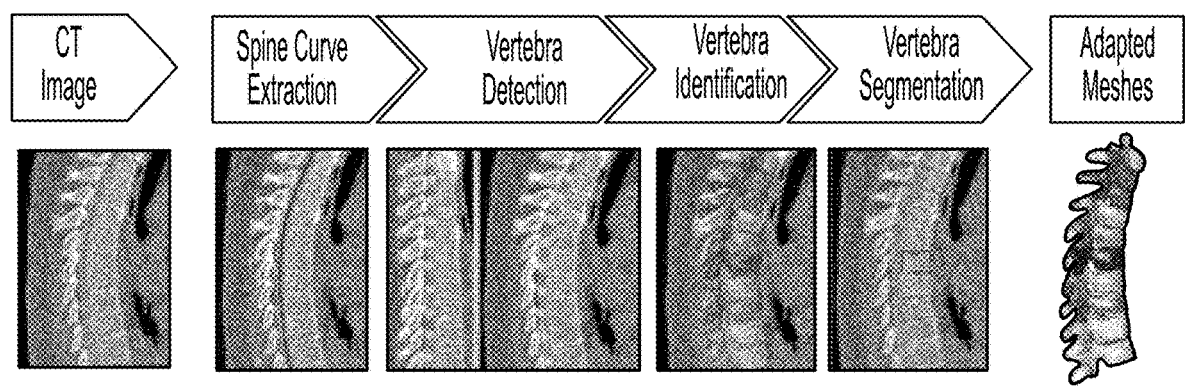
FIG. 15
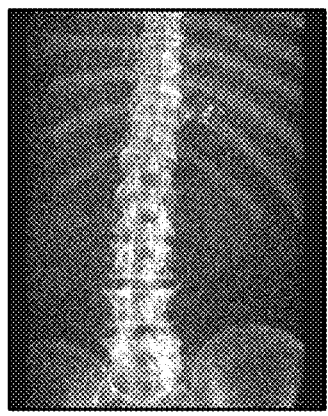 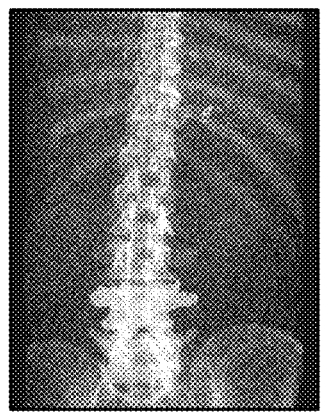 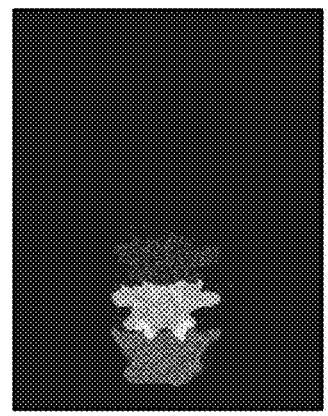
FIG. 16A FIG. 16B FIG. 16C

Axial

Sagittal

Coronal

SURGICAL NAVIGATION SYSTEMS AND METHODS

CROSS REFERENCE TO RELATED APPLICATIONS

The present application claims the benefit of the priority dates from U.S. Provisional Application Ser. No. 62/404,761, filed on Oct. 5, 2016, and U.S. Provisional Application Ser. No. 62/457,610, filed on Feb. 10, 2017, the entire contents of which are hereby expressly incorporated by reference into this disclosure as if set forth fully herein.

FIELD

The present application pertains to spine surgery. More particularly, the present application pertains to a navigation system used to enhance spatial awareness and instrument visualization while concurrently minimizing radiation exposure. Such devices, systems, and methods for use are described.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions usually experience extreme and debilitating pain, as well as diminished nerve function.

A noteworthy trend in the medical community is the move away from performing surgery via traditional "open" techniques in favor of so-called "minimally invasive" or "minimally disruptive" techniques. Open surgical techniques are generally undesirable in that they typically require large incisions with high amounts of tissue displacement to gain access to the surgical target site, which produces concomitantly high amounts of pain, lengthened hospitalization (increasing health care costs), and high morbidity in the patient population. Less-invasive surgical techniques (including minimal access and minimally invasive techniques) are gaining favor due to the fact that they involve accessing the surgical target site via incisions of substantially smaller size with greatly reduced tissue displacement requirements. This, in turn, reduces the pain, morbidity, and cost associated with such procedures. Despite the advancement in such minimally invasive techniques developed to date, there remain unmet clinical needs.

Minimally invasive surgery (MIS) involves small surgical incisions which reduce surgeon visualization of patient anatomy and three dimensional (3D) spatial awareness in comparison to traditional "open" techniques. Reduced visualization can lead to reduced location awareness and inaccurate implant placement. Technical challenges of minimally invasive surgery can lead to longer operating room time and/or increased risk of misplaced implants.

Intraoperative fluoroscopy, medical imaging that shows a continuous X-ray image on a monitor, is the current "gold standard" for surgeon visualization during minimally invasive procedures. Repeated intra-operative fluoroscopy of the patient is often required to assess the location of instruments and implants during surgery. While the x-ray exposure is generally negligible for the patient, over time and over multiple procedures on different patients, this increased exposure exposes the surgeon and operating room (OR) staff to increased health risks.

Current spine navigation technologies present numerous barriers to widespread adoption. System setup time, potential for inaccuracy, and disruption to surgical workflow have limited the widespread adoption of spine navigation technologies. Meanwhile, ORs are becoming more crowded and have limited space for additional technologies. Standalone systems that are not integrated with other OR systems add complexity, clutter, and inefficiency to the OR environment.

Therefore, a need continues to exist for systems and methods that: include compensatory changes as part of surgical planning, provide improved surgeon visualization, reduce radiation to patients and OR staff, increase surgical efficiency, and reduce OR equipment footprint.

SUMMARY

The needs described above, as well as others, are addressed by embodiments of a system for surgical navigation and related methods described in this disclosure (although it is to be understood that not all needs described above will necessarily be addressed by any one embodiment), as the system for surgical navigation of the present disclosure is separable into multiple pieces and can be used in methods, such as surgical planning and navigation methods.

In an aspect, a system for surgical navigation is provided. The system includes a first array including tracking markers, the first array releasably secured with a first anatomical feature. The system includes at least one camera configured to track the array and transmit the images of the array to a computer system including a processor, wherein the computer system is configured to display a simulation of the anatomical feature on a display screen. The first anatomical feature may be a vertebra. The first array may be releasably secured with the vertebra by a spine clamp or a spine pin. The first array may include markers in six degrees of freedom. The markers may be hemispherical. The first array may comprise recesses, and the markers may be at least partially received in the recesses. The first array may include at least two oppositely facing surfaces, each surface having a plurality of markers. The markers may be scattered over the at least two surfaces of the first array. The first array may be a 360 degree array or a 360 degree prismatic array.

The system may include a C-arm coupled with a C-arm array mount including at least one marker. The at least one camera may be configured to track the at least one marker of the C-arm array mount. The at least one camera may include an infrared camera and a visible light camera.

In another aspect, a method of guiding a second screw based on a first screw in a first vertebra of a spine of a subject is provided. The method includes providing at least one array releasably secured with the first vertebra of the spine. The method includes providing an optical tracking system in communication with a navigation system including a computer system having a processor, wherein the optical tracking system captures images of the array and the spine and communicates the images to the computer system. The method includes tracking the insertion of the first screw into the first vertebra with the optical tracking system and communicating images of the tracked first screw to the computer system. The method includes simulating, via the computing system, a second screw at a predetermined orientation based on the images of the tracked spine and the tracked first screw. The method includes displaying the simulated second screw on a display in communication with the computer system.

The simulated second screw may include a simulated trajectory. The computer system may be configured to receive instructions from a user to bookmark a representation of the tracked and inserted first screw and cause the display screen to display the representation of the tracked and inserted first screw. The computer system may be configured to generate a simulated three dimensional model of the spine of the subject. The computer system may be configured to determine the vertebral levels of the spine. The method may include releasing the at least one array from the first vertebra; releasably securing the at least one array with a second vertebra of the spine; capturing images of the at least one array with the second vertebra with the optical tracking system; communicating captured images of the at least one array with the second vertebra to the computer system; tracking the insertion of a third screw into the second vertebra with the optical tracking system and communicating images of the tracked third screw to the computer system; simulating, via the computing system, a fourth screw at a predetermined orientation based on the images of the tracked spine and the tracked third screw; and displaying the simulated fourth screw on a display in communication with the computer system.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 6E illustrates a front perspective view of an array according to an embodiment of the navigation system.

FIG. 6F illustrates an exploded view of the array of FIG. 6E.

FIG. 6K illustrates elevation views over 90 degree rotations of the array of FIG. 6I.

FIG. 8D illustrates a front perspective view of a clamp according to an embodiment of the navigation system.

FIG. 8E illustrates a front perspective view of a clamp according to another embodiment of the navigation system.

FIG. 15 depicts a segmentation process according to an embodiment of the navigation system.

FIGS. 16A-16C illustrate vertebrae segmentation from a CT model of the spine according to an embodiment of the navigation system.

DETAILED DESCRIPTION

Figure 1:
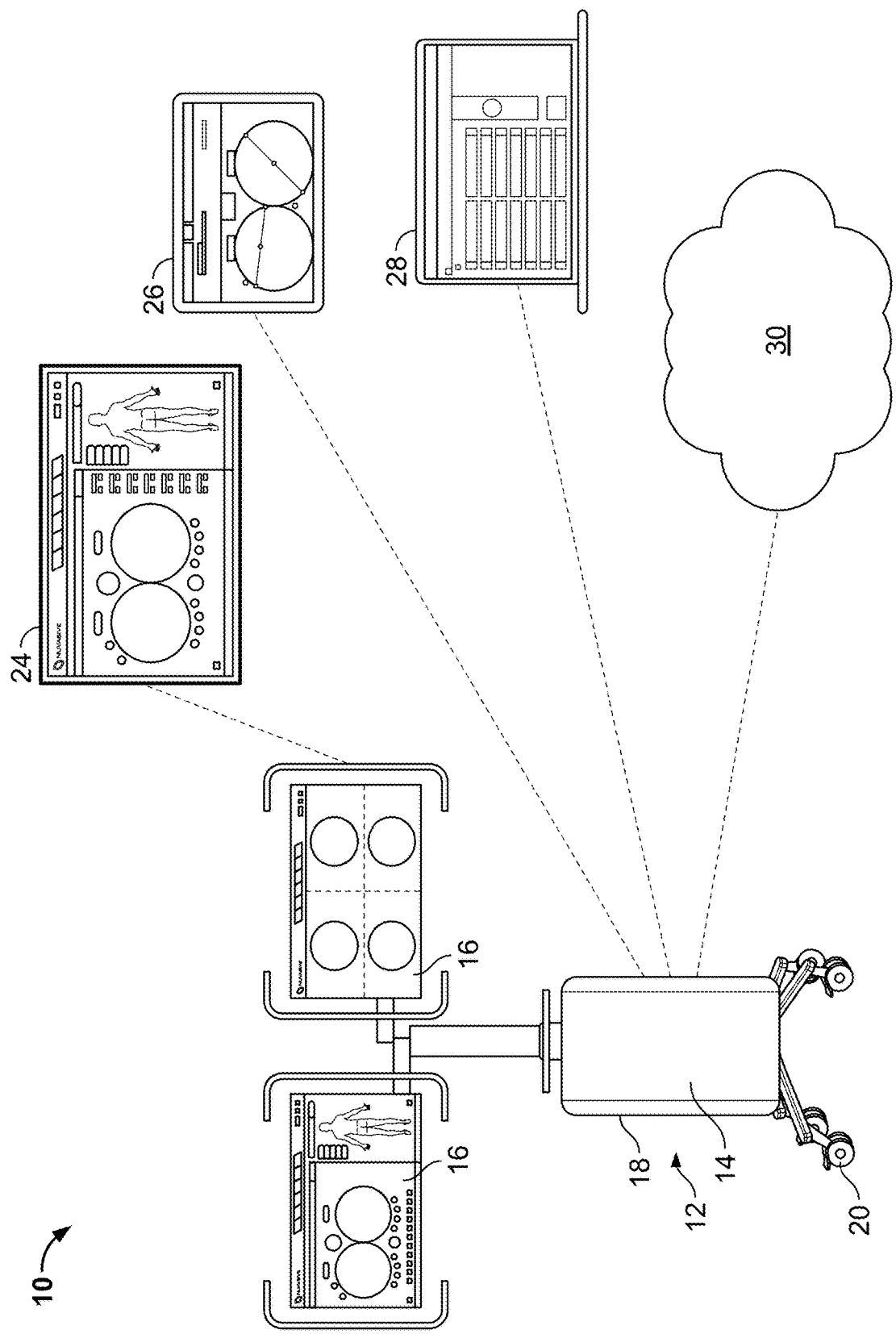
FIG. 1 illustrates a computer system according to one embodiment of the navigation system.

Illustrative embodiments of a system for surgical navigation system and related methods are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for surgical navigation system and related methods disclosed herein boast a variety of inventive features and components that warrant patent protection, both individually and in combination.

As shown and described herein, the term "navigation" describes the ability to leverage intraoperative imaging in real-time to obtain spatial awareness between anatomical structures and instrumentation. The navigation system provides maximum surgeon visualization with minimal radiation exposure through an innovative and efficient solution during MIS and traditional open spine procedures. Specifically, the navigation system enables surgeons to perform 3D image-guided surgery with increased accuracy exposure during posterior and anterior column procedures. This provides benefits for surgeons and hospitals alike: 1) for degenerative and MIS surgeons who desire improved visualization while simultaneously reducing radiation exposure; 2) for deformity surgeons who desire real-time spinopelvic parameter assessment and anatomical orientation in complex spine procedures; and 3) for hospital administrators who desire to reduce the total cost of health care through more predictable outcomes form accurate implant placement and reduced morbidity of MIS procedures. Indeed, the system of the present disclosure provides for reduced total cost of care though facilitating more predictable outcomes, reduced OR time, reduced hospital length of stay, reduced post-op complication rates, and reduced revision operations (due to accurate and repeatable implant placement).

The navigation systems and methods described herein are compatible with spine procedures and the instruments and implants associated therewith. By way of example, the navigation system and methods described herein are compatible with open and MIS pedicle screw placements for thoracolumbar fusions, lateral interbody fusion procedures including lateral lumbar interbody fusion (XLIF), trauma procedures, maximum access surgery transforaminal lumbar interbody fusion (MAS TLIF), maximum access surgery posterior lumbar interbody fusion (MAS PLIF), lateral fixation procedures, corpectomies, anterior cervical discectomy and fusion (ACDF), and posterior cervical fusion (PCF). It is contemplated that the navigation systems and methods will integrate planning, such as the iGA platform by NuVasive, Inc., intraoperative monitoring, automated rod bending, etc. to provide a holistic view of the anatomy and foster enhanced procedural solutions.

In a first aspect, a navigation system 10 is provided. As shown in FIG. 1, the navigation system 10 may include one or more hardware components, one or more software components, and one or more auxiliary components. For example, the navigation system 10 may include a computer system 12 including a control unit 14 including at least one processor configured to execute computer executable instructions (i.e., software), and one or more display screens 16. The control unit 14 may be housed in a technology hub 18 having one or more locking wheels 20 disposed thereon such that the technology hub 18 may be easily positionable around the OR. The technology hub 18 may include one or more arms 22 connecting to the display screens 16. The control unit 14 may be configured for executing the application software and algorithms, and communicating and interfacing with other system components associated with the navigation system 10, such as auxiliary displays 24, remote control devices 26, such as tablets or phones, and mobile computing devices 28, such as intraoperative neuromonitoring technician laptops, and cloud remote and cloud planning systems 30.

The computer system 12 may receive universal imaging inputs, meaning that it has the ability to work with a pre-operative CT input, a pre-operative MRI input, a 3D C-arm input, or an intraoperative CT input. The imaging inputs may be formatted according to industry standards, such as the Digital Imaging and Communications in Medicine (DICOM) standard, the Picture Archive and Communication System (PACS) standard, Phase Alternating Line (PAL) standard, and National Television System Committee (NTSC) standard. The system 12 may receive the input over one or more networks (e.g., wired or wireless local area network, such as a hospital PACS) or via USB, CD, DVD, DVI, composite video, or analog video. Advantageously, as discussed herein, the present system 10 employs automatic registration with intra-operative and pre-op CT images, the system 10 is configured to perform segmentation of each vertebral body through image recognition, and the system 10 is configured to register individual vertebral bodies such that the spine can be dynamically tracked during the surgical procedure.

The one or more display screens 16 may be touch screens such that they include a graphical user interface (GUI) with which the user can directly input commands by touching the screen 16. The system 10 offers intuitive and convenient system interaction with the software and hardware available to surgeons (and users others within the surgical field) and other hospital personnel (outside the surgical field). While various descriptions of the aspects of the present disclosure may refer to a surgeon, or surgeons, it is to be understood that the functionality of such aspects may extend to other users, as contextually appropriate, such that the term "surgeon(s)" supports the term "user(s)." The software may be primarily controlled through the touch screen graphical user interface on the one or more display screens 16, which controls the navigation system 10. In one embodiment, the system 10 includes a secondary control through the one or more remote control devices 26.

The navigation system 10 receives data and inputs from various other parts of the system 10, including the 3D imaging data and optical camera(s) 34, 36 that track the vertebrae and surgical instruments (discussed in further detail below), surgeon inputs, and processing to provide real-time navigation information to the surgeon or OR personnel. The surgeon/OR personnel can interact with the navigation software from the sterile field for navigation view settings, instrument selection/calibration real-time implant planning and sizing, administrative features, and option selection. The software is controlled without interfering with other intraoperative computer-assisted modalities and the system 10 is able to easily transition between navigation modes and other modes, for example, intraoperative neuromonitoring (TOM) services, NUVAMAP O.R., and BENDINI software modes.

Figure 2:
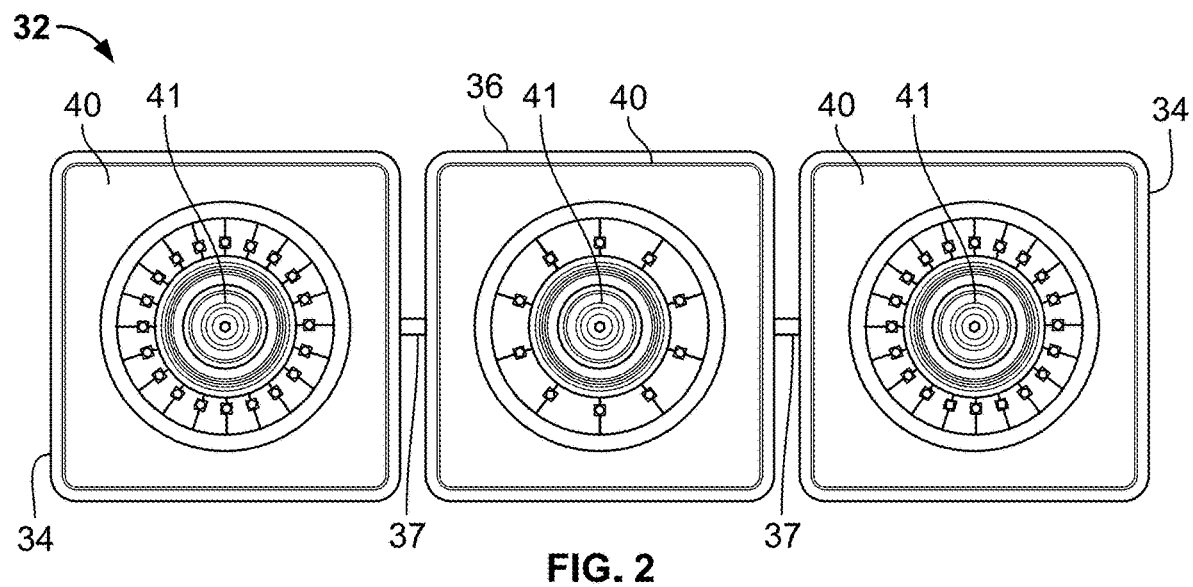
FIG. 2 illustrates an optical tracking system according to an embodiment of the navigation system.
Figure 3:
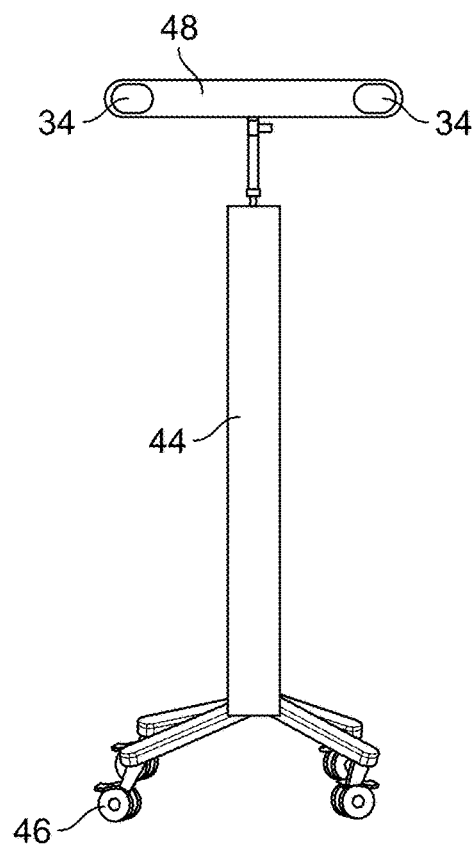
FIG. 3 illustrates an optical tracking system and a mobile cart according to an embodiment of the navigation system.

In a second aspect of the navigation system 10, the system 10 includes an optical tracking system 32, shown in FIGS. 2 and 3. The optical tracking system 32 may provide real-time location of objects (e.g., one or more body locations such as vertebral bodies of the spine, and one or more instruments for use in surgery) in relationship to each other as the objects move through space. The optical tracking system 32 may be in communication with the control unit 14 of the computer system 12 of the navigation system 10. The optical tracking system 32 may include one or more cameras that are infrared (IR) cameras 34 and/or visible light cameras 36 (i.e., sense and transmit data from the IR or visible light spectrums). Each camera 34, 36 may be selected between IR and visible light modes under software control by the control unit 14. The optical tracking system 32 senses (i.e., sees) the location of one or more tracking arrays 38 (FIGS. 4A and 4B) within the field of view of the system 32. The tracking arrays 38 may be positioned on one or more anatomical features 4 of a subject 2, such as vertebral bodies of a human undergoing spinal surgery, and one or more surgical instruments 6. The optical tracking system 32 provides the navigation system 10 with dynamic 3D position information corresponding to the anatomical features 4 and/or the surgical instruments 6 being tracked.

The optical tracking system 32 may be configured in any suitable orientation. In one embodiment, illustrated in FIG. 2, the optical tracking system 32 includes a first and a second IR camera 34 flanking a first visible light camera 36. The cameras 34, 36 may be discrete units or connected together by a camera base 37. The cameras 34, 36 may be compact enough to be positioned within a sterile field of a surgical procedure without interfering with the procedure. The cameras 34, 36 may contain a high number of pixels. As used herein, the term, "pixel" is used to refer to a single scalar element of a multi-component representation (also referred to as a photosite). The cameras 34, 36 may capture at least 1 megapixel, at least 2 megapixels, at least 5 megapixels, at least 10 megapixels, at least 12 megapixels, at least 15 megapixels, or at least 20 megapixels. A thin, transparent barrier 40 may be placed over the lenses 41 of the cameras 34, 36. Advantageously, a high pixel count enables the barrier 40 to be placed over the lenses 41 of the cameras 34, 36 while the cameras 34, 36 are in-use without sacrificing the accuracy of the position of the sensed tracking arrays 38. The barrier 40 also enables the cameras 34, 36 to be draped and placed within the sterile field. Another benefit of embodiments of the system 10 having the barrier 40 is that the barrier 40 enables the cameras 34, 36 to be in close proximity with the tracking arrays 38, which further allows the arrays 38 to be reduced in dimensions such that the arrays 38 are less likely to interfere with the surgical procedure being performed.

The optical tracking system 32 may be used with markers 42 disposed on one or more arrays 38 (discussed below). The markers 42 may be small in size (e.g., 3 mm diameter or as small as technologically feasible) with a minimal tracking array footprint (less than 10 mm between markers 42 allowing for small array 38 size). In addition to tracking spatially track arrays 38, the optical tracking system 32 may track objects that have arrays 38 as the objects change orientation (e.g., rotation, yaw, roll). The optical tracking system 32 may be positioned within the OR to minimize the potential for line-of-sight disruptions with the subject 2 for the surgeon performing the surgical procedure.

In embodiments of the navigation system 10 where the cameras 34, 36 are placed outside of the sterile field, the cameras 34, 36 may be placed on a mobile cart 44 (FIG. 3) with one or more locking wheels 46 such that the cart 44 may be positioned variously by rolling the cart 44 within the OR. The cart 44 may be placed proximate to one end of a surgical bed. The cart 44 may comprise a base 48 for receiving the cameras 34, 36. The base 48 may be lockingly adjustable, including height, longitudinally, and laterally so that the cameras 34, 36 may be optimally positioned for the surgical procedure.

In embodiments of the navigation system 10 where the cameras 34, 36 are placed within the sterile field, the draped cameras 34, 36 may be configured to view the C-arm 194, arrays 38 (including on anatomical features 4 and/or instruments 6) by placing one or more cameras 34, 36 at one of the following locations: patient anchor attachment, bedrail attachment, cart attachment, an overhead boom/light attachment, or any combination thereof. Some embodiments of the navigation system 10, discussed below, include the optical tracking system 32 that allows a single (i.e., initial) set up of the cameras 34, 36 with no additional adjustments necessary or made during a surgical procedure, thereby improving surgical workflow efficiency by eliminating the need for hospital personnel to adjust and re-adjust the cameras 34, 36 during the operative procedure to "see" or calibrate the navigated instruments 6 or the markers 42.

Referring to FIGS. 4-12B, in a third aspect, the navigation system 10 includes one or more tracking arrays 38 that can be securely disposed on the anatomical features 4 and/or the surgical instruments 6. The navigation system 10 tracks the tracking arrays 38, such by information received by cameras 34, 36, to effectuate the navigation and tracking of anatomical features 4 and surgical instruments 6 as will be described in greater detail below. According to one or more implementations, the navigation system 10 may track the spine using tracker 50.

Figures 4A, 4B:
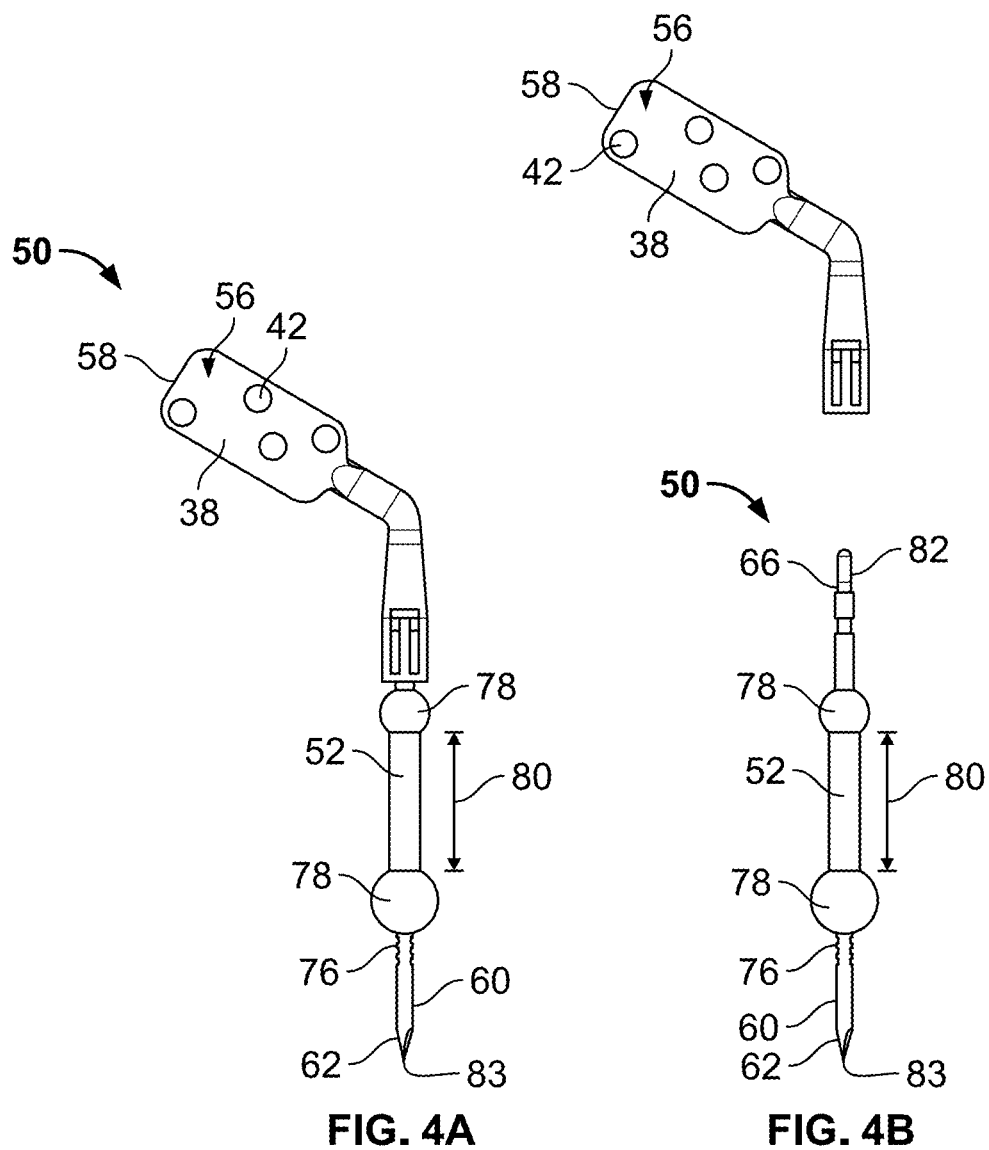
FIG. 4A illustrates an assembled tracker according to an embodiment of the navigation system.
FIG. 4B is an exploded view of the assembled tracker of FIG. 4A.
Figure 9A:
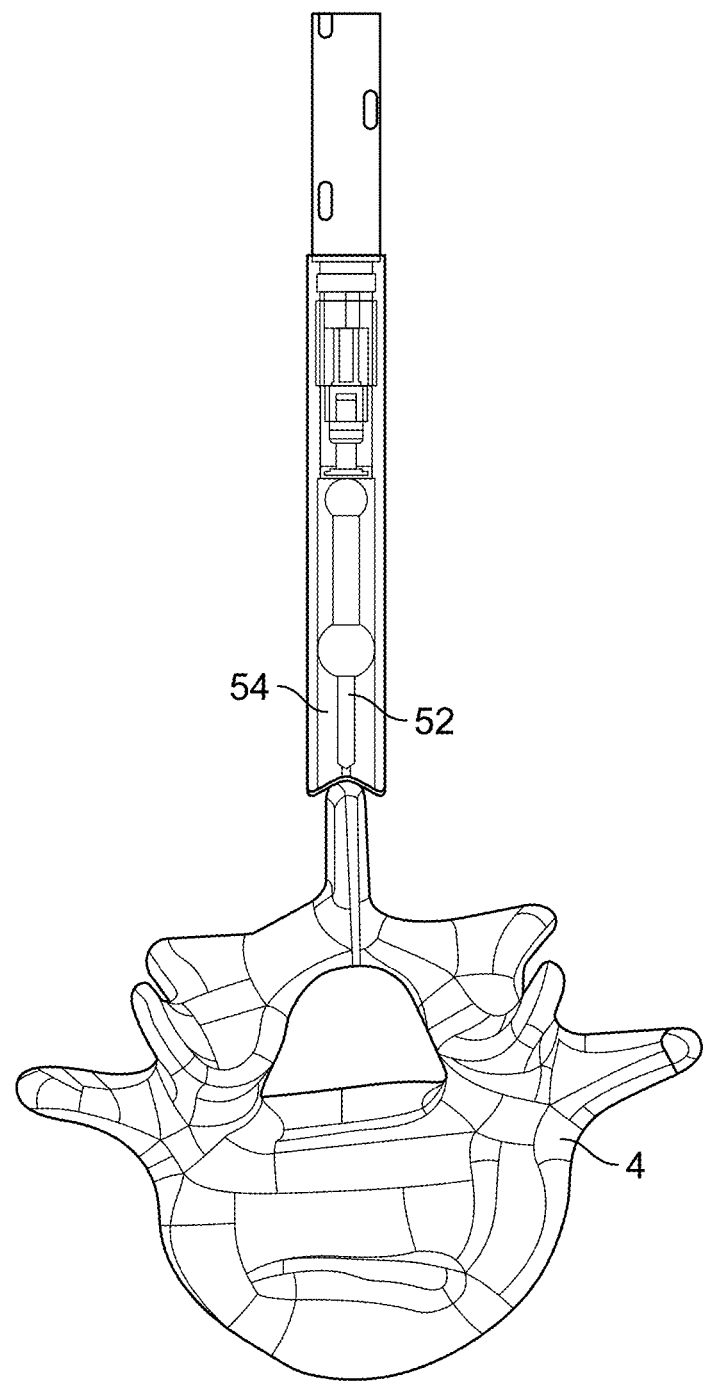
FIGS. 9A-9C illustrate the use of a spine tracker inserter affixing a spine pin and an array to a spinous process in accordance with an embodiment of the navigation system.
Figure 9C:
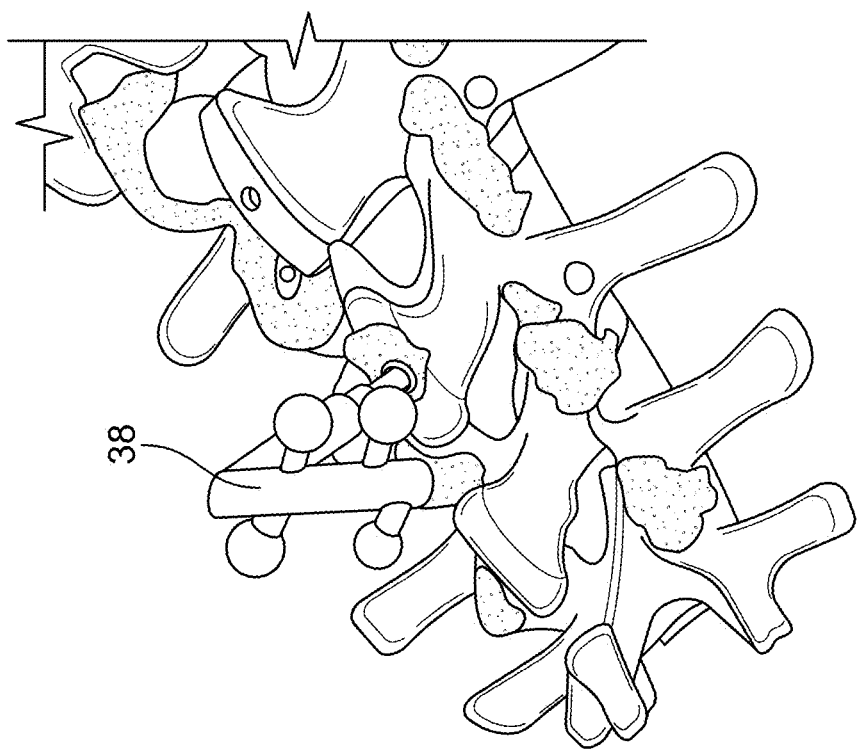
Figure 9B:
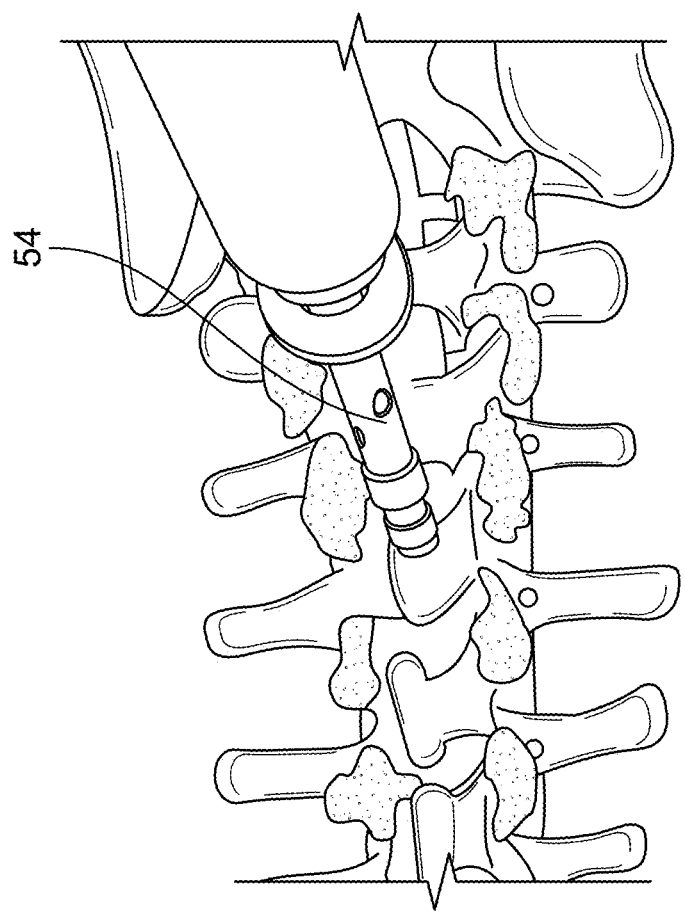

As shown in the embodiment of FIGS. 4A-4B, the tracker 50 (i.e., the assembly of the array 38 and pin 52) comprises the array 38 having one or more markers 42 disposed thereon. The arrays 38 may securely, or lockingly and releaseably, engage with a spine pin 52. The markers 42 may be variously positioned on the array 38. The markers 42 may be positioned at various points on a first surface 56 of the array 38. The arrays 38 may be scattered over the first surface 56, as shown in FIGS. 4A and 4B. The spine pin 52 may be positioned with or engage one or more anatomical feature 4 (e.g., vertebrae) by use of a spine tracker inserter 54 (FIGS. 9A-9C). Advantageously, when engaged via the spine pin 52, navigation system 10 may sense and track the position of the arrays 38 engaged with the spine pin 52, thereby tracking the position of the vertebrae 4 with which the spine pin 52 is engaged. The tracker 50 may have a first end 58 and an oppositely disposed second end 60, the array 38 disposed at the first end 58 and the spine pin 52 disposed at the second end 60. At the terminus of the second end 60, the spine pin 52 may include a sharp tip 62 configured to engage and be removably insertable into anatomical feature 4. Thus, when the array 38 is connected to the spine pin 52 that is inserted with the anatomical feature 4, such as vertebrae, the tracker 50 enables individual vertebral level registration and dynamic spine tracking as will be explained in greater detail below. The spine pin 52 may include an axial retention feature 76 (e.g., a helical thread) proximate to the tip 62 for axially securing the pin 52 with the anatomical feature 4.

Figure 4C:
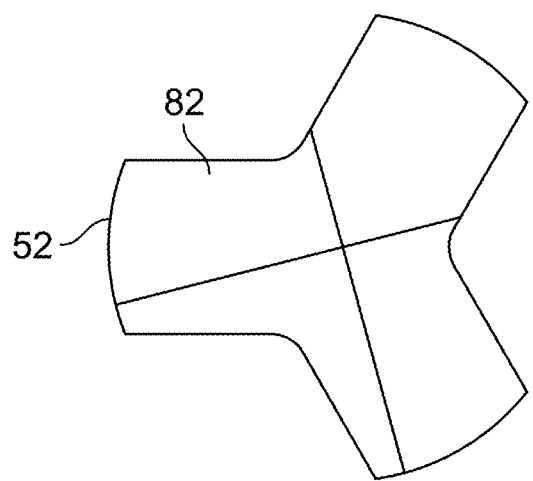
FIG. 4C is a cross section view of a spine pin according to an embodiment of the navigation system.

The tracker 50 may include one or more radiographic glyph elements 78, such as a sphere. The tracker 50 may include a first radiographic glyph element 78 proximate to where the array 38 interfaces with the spine pin 52, and a second radiographic glyph element 78 proximate to the axial retention feature 76. The distance 80 between the radiographic glyph elements 78 may be from 5 mm to 100 mm, from 15 mm to 80 mm, about 40 mm, or any value or subrange thereof. As shown in FIG. 4C, an array end 82 of the spine pin 52 may have a tri-lobular profile (i.e., cross-section) to prevent the rotation of the pin 52 when the pin 52 is engaged with the array 38. The array 38 may be coupled with the spine pin 52 after the spine pin 52 is secured with the anatomical feature 4. The spine pin 52 may serve as a fiducial for image registration with the system 10, allowing for registration within multiple degrees of freedom, such as at least 4 degrees of freedom, at least 5 degrees of freedom, or at least 6 degrees of freedom, as will be explained in greater detail below.

Figure 5:
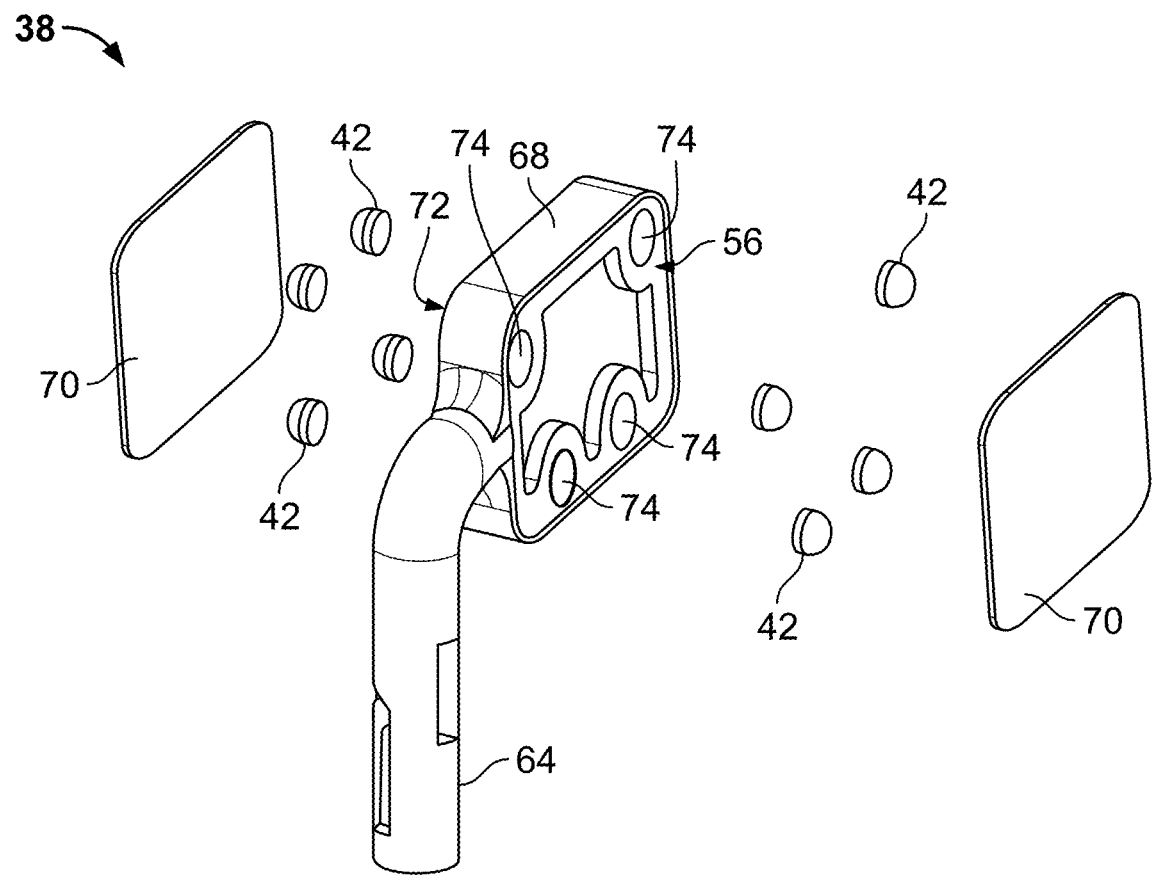
FIG. 5 is an exploded view of an array according to an embodiment of the navigation system.

FIG. 5 illustrates an exploded view of the array 38 according to an embodiment of the system 10. The array 38 comprises a connecting portion 64 for securely coupling the array 38 at the first end 58 of the tracker 50. The connecting portion 64 is sized and dimensioned to securely couple with to a complementary surface (e.g., a reference surface) 66 of the tracker 50. The array 38 includes a body 68 for supporting the various components of the array 38, such as the markers 42 and a cover 70 for protecting the markers 42. The markers 42 may be disposed on opposite sides (e.g., on the first surface 56 and an oppositely facing second surface 72) of the array 38. The markers 42 may be at least partially received in complementarily-shaped recesses 74 in the body 68. The markers 42 and/or body 68 may be provided in a sterile form such that they can be utilized within the sterile surgical field. The markers 42 may be provided in sterile packaging. The protective cover 70 may be clear and thin, and protect the markers 42 from being obscured from the system 10, particularly the optical tracking system 32, by debris such as blood from the patient undergoing surgery. The cover 70 may be constructed of a polymer or glass, or may be a film. The cover 70 may be polarized to limit the field of view if so desired.

The markers 42 may be reflective and hemispherical in shape, as shown in FIG. 5, or spherical in shape. In embodiments of the system 10 having hemispherical markers 42, the hemispherical shape offers several advantages relative to a reflective sphere. Advantages of the hemispherical shape include the ability to be more fully recessed with recesses 74 such that the viewing angle is physically limited so that the markers 42 are not presented to the camera when other markers 42 are directly facing the cameras 34, 36 allowing for accurate marker 42 tracking by the system 10. Additionally, because the markers 42 are recessed, the cover 70 can be placed over the markers 42. When used in conjunction with other components of the system 10, such as high pixel count cameras 34, 36, the markers 42 may be dimensioned to be about 3 mm in size. The markers 42 create a distinctive pattern around the body 68 of the array 38 such that the cameras 34, 36 can sense and track the location and orientation of the anatomical feature 4 or an instrument 6.

FIGS. 6A-6K illustrate embodiments of the array 38. In FIGS. 6A-6D, the body 68 of the array 38 is elongated and comprises a plurality of arms 84 extending from the body 68. The body 68 may comprise a spine pin engagement feature 88 for releasably securing the spine pin 52. The array 38 is removable and repositionable such that the array 38 may be positioned with the spine pin 52 or a surgical instrument 6 in either of a right handed or a left handed orientation. Beneficially, this feature allows the surgeon to reposition the array 38 away from the side where the surgical procedure is being performed such that the array 38 does not interfere, whether by view or physical obstruction, with the surgical procedure. This feature also aids in the ability for the cameras 34, 36 to see the markers 42 without, or with fewer, obstructions, as the surgeon can alternate the array 38 between left and right orientations as the surgeon progresses, for example, down the spine, allowing the cameras 34, 36 to view multiple vertebrae levels. If line of sight due to position of the arrays 38 becomes an issue during the surgery, vertebrae that are not being operated on can have their respective array 38 removed from the pin 52 to declutter the operative area and then releasably resecured when the surgeon has moved past that location. The benefits of decluttering the operative area are enormous, as the minimized footprint of the present system reduces hospital employee demand (saving money and hospital resources), and integrates with existing technologies on a single system. The relatively small size of the arrays 38 also reduces patient and surgeon impact, allowing the surgeon to work freely and minimize OR time, which is beneficial for the patient.

Figure 6A:
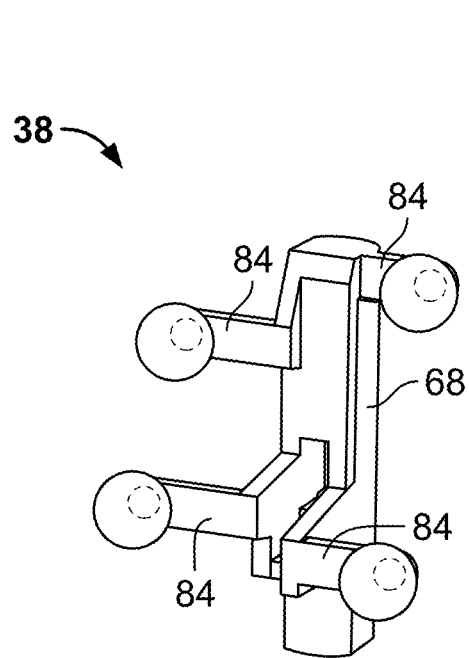
FIG. 6A illustrates a front perspective view of an array according to one embodiment of the navigation system.
Figure 6B:
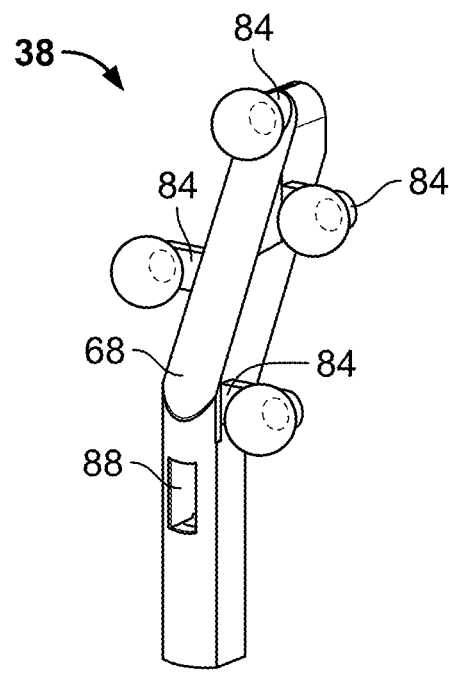
FIG. 6B illustrates a front perspective view of an array according to another embodiment of the navigation system.
Figure 6C:
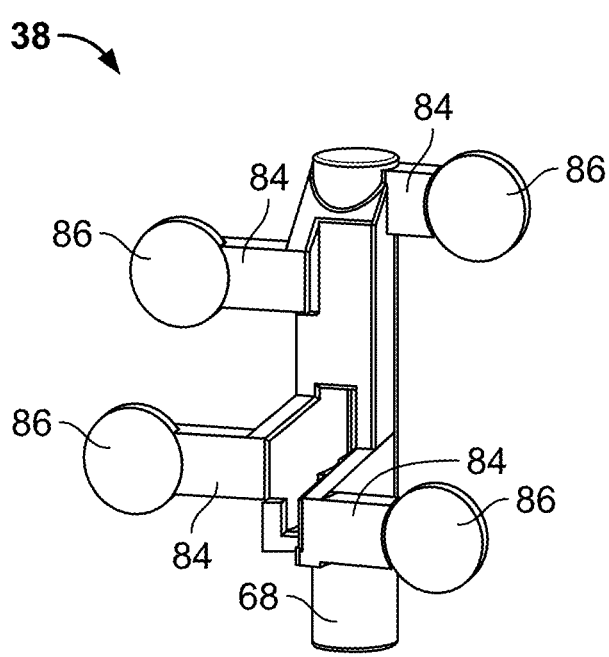
FIG. 6C illustrates a front perspective view of an array according to an embodiment of the navigation system.
Figure 6D:
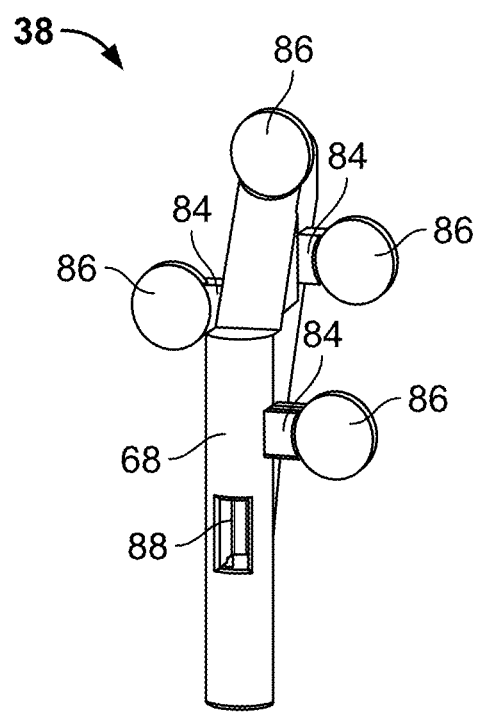
FIG. 6D illustrates a front perspective view of an array according to yet another embodiment of the navigation system.

The arms 84 may variously extend laterally, longitudinally, and vertically from the body 68 such that each arm 84 terminates in a different position relative to the body 68. Each arm 84 may include a marker 42, such as a spherical marker 42 (FIGS. 6A-6B). In the array 38, depicted in FIGS. 6C-6D, the arms 84 terminate to paddles 86 such that reflective markers 42, such as adhesive reflective dots, can be disposed on the paddles 86.

As shown in FIGS. 6E-6K, the array 38 may be a 360 degree array 38. The 360 degree array 38 may include the body 68 that is frustoconical, as shown in FIGS. 6E-6H. The frustoconical body 68 may comprise one or more arms 84 that variously (vertically and around the body) extend from the body 68 to spherical markers 42. The array 38 may include a base 90. The base 90 may interface with a collar 92 by a retention mechanism 94, such as an O-ring seal, that secures and seals the interface between the base 90 and the collar 92. The collar 92 may comprise one or more legs 96, such as an oppositely disposed pair, that upwardly extend away from the collar 92 and are configured for engaging corresponding apertures (which can alternatively be recesses) 98 in the body 68. The body 68 may comprise a top aperture 100 that is open to an internal chamber 102, the internal chamber 102 opens to a collar aperture 104. The arms 84 may extend away from the body 68 farther than the collar 92 extends from the body 68 (FIGS. 6E-6F).

Figure 6H:
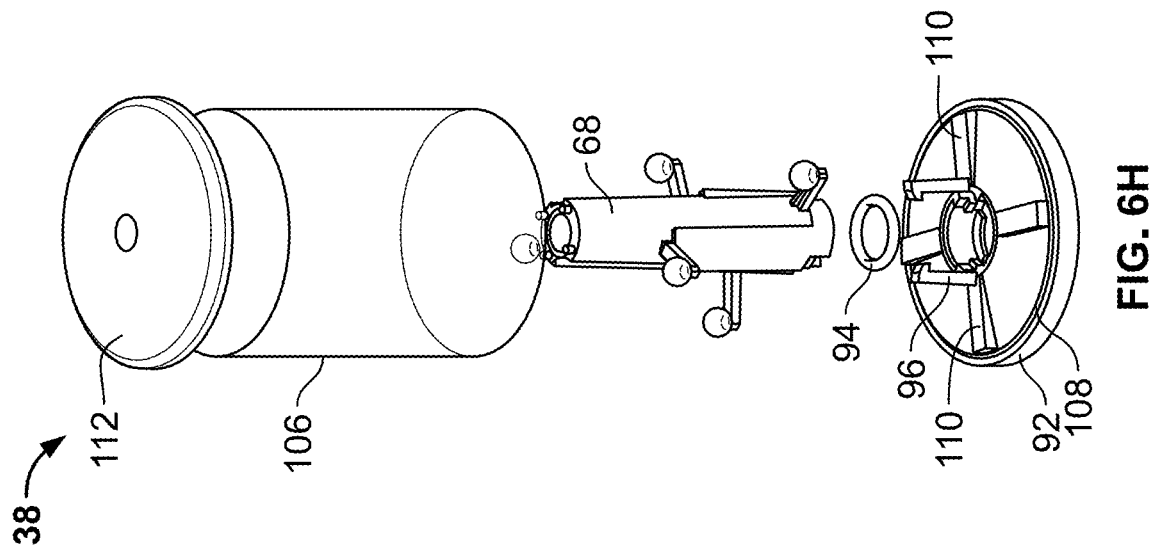
FIG. 6H illustrates an exploded view of the array of FIG. 6G.
Figure 6G:
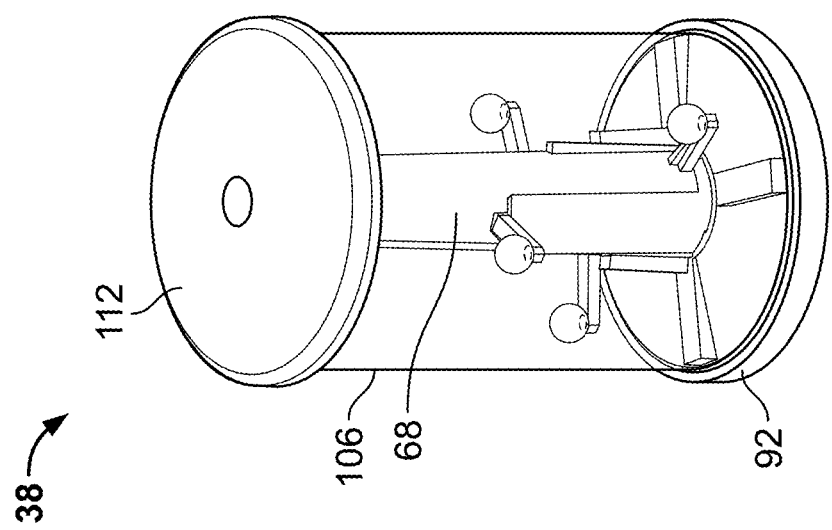
FIG. 6G illustrates a front perspective view of an array according to another embodiment of the navigation system.

As shown in FIGS. 6G-6H, the 360 degree array 38 may be configured to receive, or be securely and releasably coupled with, a shield 106. The shield 106 may extend 360 degrees around the body 68, the arms 84, and the markers 42. The collar 92 may extend away from the body 68 farther than the arms 84 extend from the body 68 (FIGS. 6G-6H). The collar 92 may comprise a groove 108 extending around, or proximate to, its perimeter for releasably securing the shield 106. The collar 92 may include one or more guides 110 that extend from the collar aperture 104 to the groove 108 to further guide and secure the shield 106 within the groove 108. A top cover 112 may be releasably secured over the shield 106 opposite of the collar 92, the top cover 112 including a groove 114 (not shown) similar to groove 108 for receiving the shield 106.

Figure 6J:
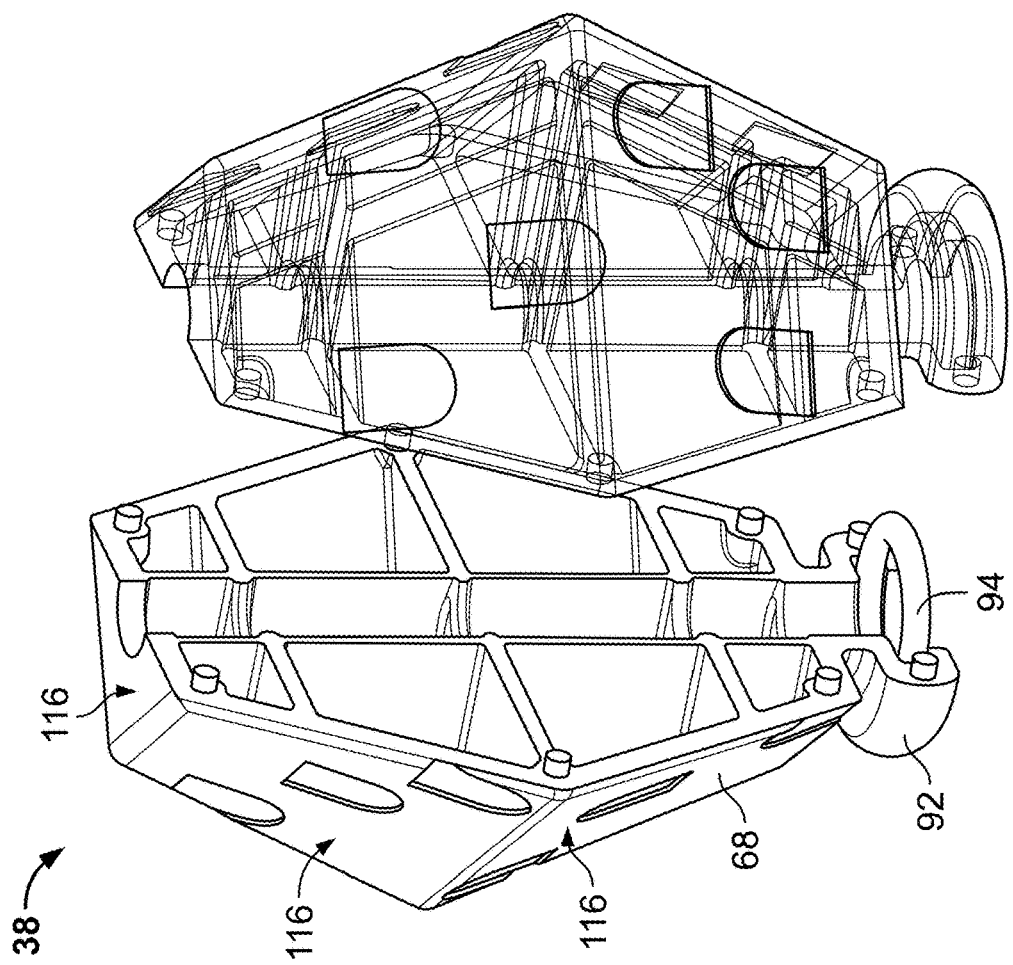
FIG. 6J illustrates an exploded view of the array of FIG. 6I.
Figure 6I:
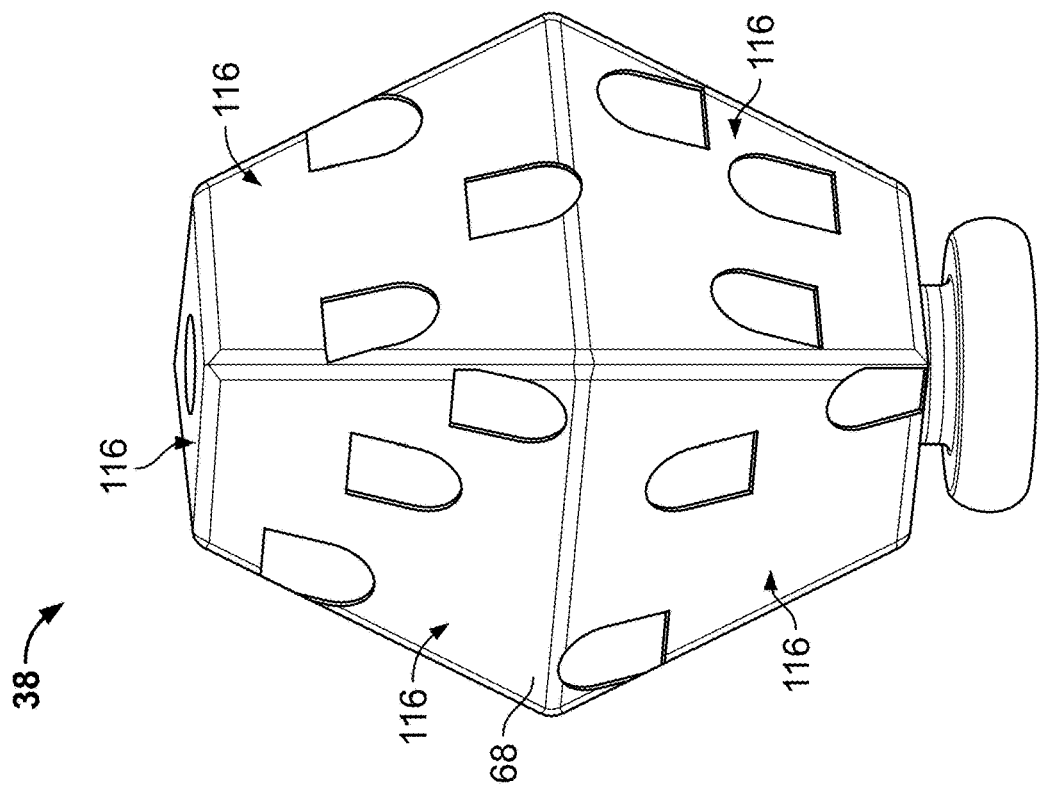
FIG. 6I illustrates a front perspective view of an array according to yet another embodiment of the navigation system.

As illustrated in FIGS. 6I-6K, the 360 degree array 38 may be a 360 degree prismatic array 38. The body 68 may be a polygon (e.g., a prism), such as a ten-sided pyramid having a profile of two opposing frustums. The exterior surfaces, or faces, 116 of the body 68 may each have one or more pockets 118 disposed therein. The pockets 118 may have a pocket-shaped profile (i.e., continuously curved on a first end leading to substantially straight sidewalls that lead to a flat second end opposite the continuously curved first end). Markers 42, such as adhesive reflected dots, may be placed within the pockets 118. Advantageously, the pocket-shaped profile of the pockets 118, particularly the curved first end, assists in guiding and securing the markers 42. The body 68 may be integrally formed with the collar 92, with the retention mechanism 94 configured to be secured with the collar 92. The body 68 may be integrally formed in one or more cooperative sections, as shown in FIG. 6J. As illustrated in FIG. 6K, which shows the body 68 rotated 90 degrees (1, 2, 3, and 4), the pockets 118 may be in varying orientations and positions on each face 116 of the body such that no two faces 116 have the same pocket 118 position and orientation. Advantageously, when used with markers 42, this causes the marker 42 placement to be unique when viewing each 90 degree rotation of the body 68 and the respective faces 116. For example, some pockets 118 may be toward a center 120 of the body 68 while other pockets 118 are toward distal ends 122 of the body, and pockets 118 may be rotated variously between 0 degrees and 360 degrees relative to one another. Advantageously, this configuration allows each pocket 118 may be positioned uniquely on the face 116 relative to all pockets 118 on all faces 116, which is especially beneficial when using the array 38 with markers 42, as each marker is in a different relative position and orientation, which allows cameras 34, 36 to see more of the markers 42, and sense more spatial data, when the system 10 is in-use.

Figure 7:
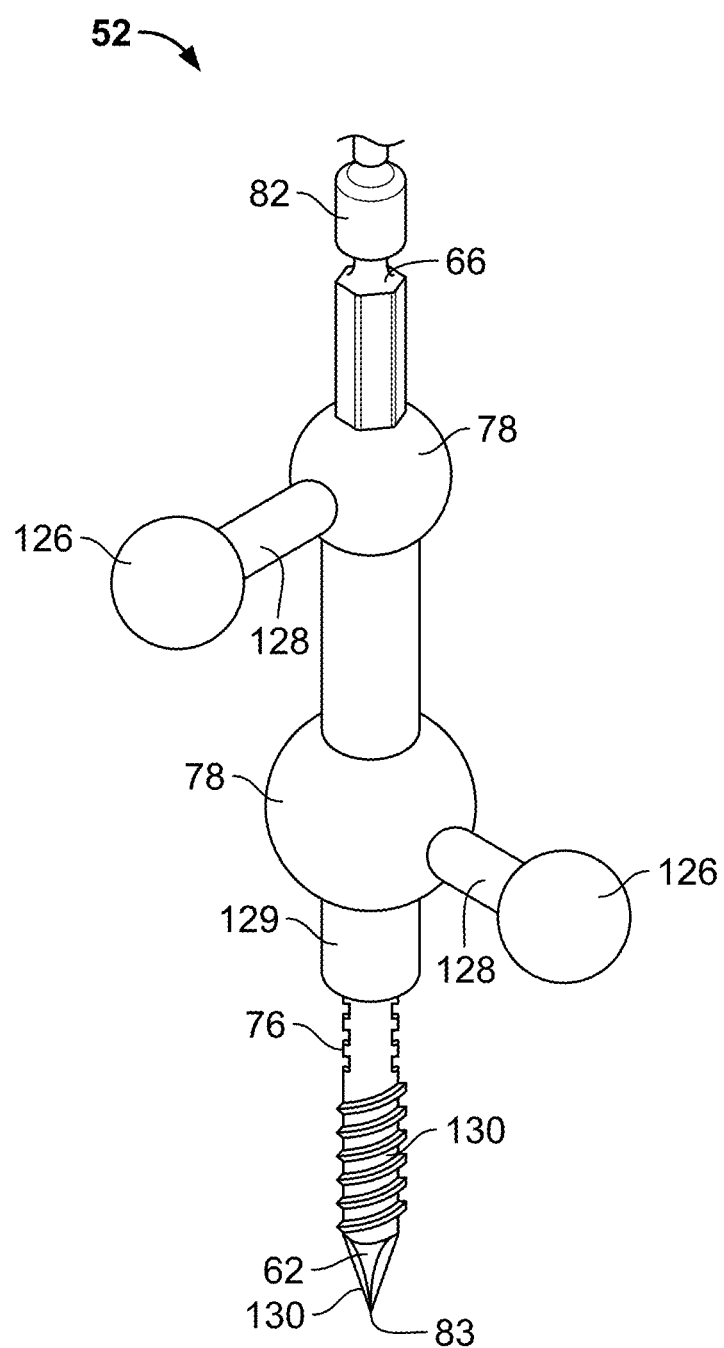
FIG. 7 illustrates a spine pin according to an embodiment of the navigation system.
Figure 8A:
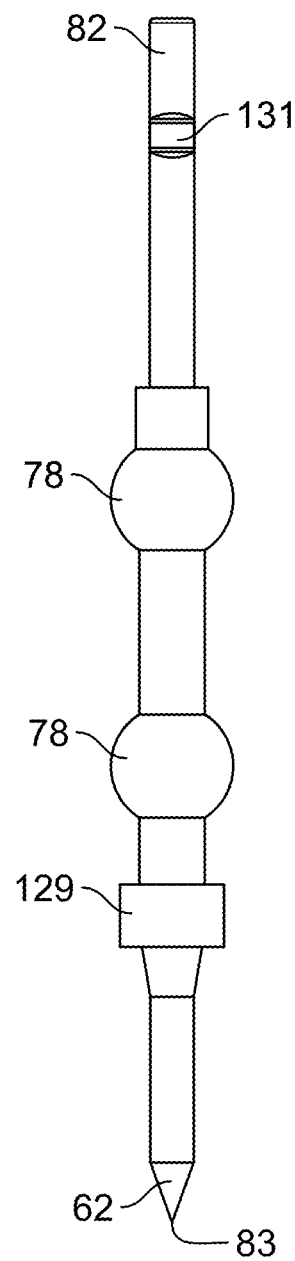
FIG. 8A illustrates a spine pin according to another embodiment of the navigation system.

Referring to FIGS. 7-8E, a fourth aspect of the system 10 includes the spine pin 52 and/or a spinal clamp 124. The spine pin 52 and the spinal clamp 124 allow for secure and releasable attachment of the array 38, connecting the array 38 with the anatomical feature 4, such as a vertebrae, or more specifically, a spinous process. As shown in FIG. 7, the spine pin 52 may have distal radiographic glyph elements 126 that extend outwardly from the pin 52 by glyph arms 128. The glyph arms 128 may extend from the radiographic glyph elements 78 to the distal radiographic glyph elements 126, such that the glyph arms 128 connect the radiographic glyph elements 78 and the distal radiographic glyph elements 126. Advantageously, this configuration of glyph elements 78, 126 allows for the pin 52 to contribute to the tracking capabilities of the system 10 by functioning as radiographic fiducials.

Proximate to the depth retention feature 76 and opposite of the tip 62, the pin 52 may include a depth limiter 129 (e.g., an expanded circumferential body). The depth limiter 129 functions as a physical stop when the pin 52 is being inserted into the anatomical feature 4, such as to prevent the pin 52 from being inserted too deeply into the feature 4 and risk causing injury to the patient as a result thereof.

Figure 8B:
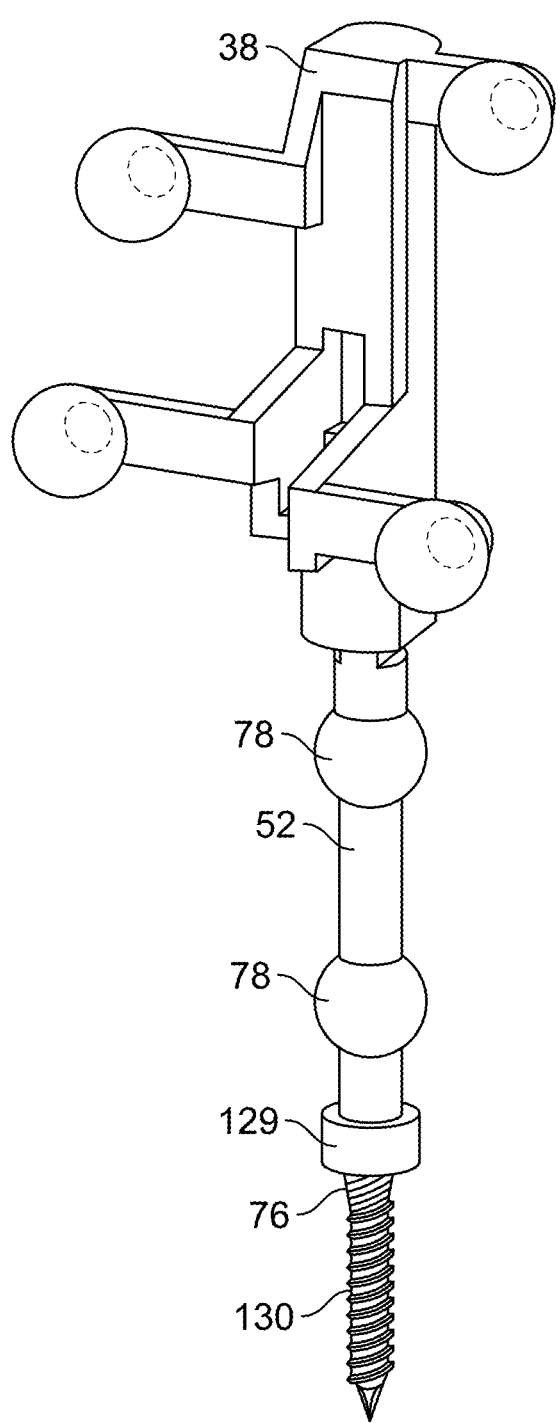
FIG. 8B illustrates a spine pin and an array (as a tracker assembly) according to an embodiment of the navigation system.
Figure 8C:
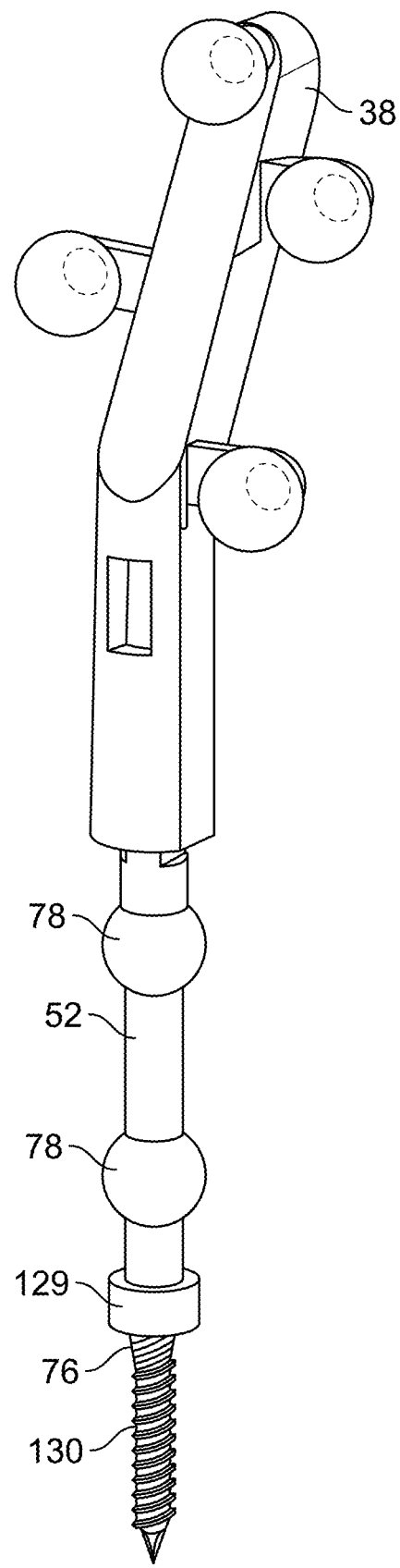
FIG. 8C illustrates a spine pin and an array (as a tracker assembly) according to yet another embodiment of the navigation system.

The axial retention feature 76 may include a helical thread, as shown. Meanwhile, the portion of the pin 52 between the axial retention feature 76 and a tip end 83 of the pin 52 may include bone thread 130. The bone thread 130 and the axial retention feature 76 may be a differential pitch to increase bone retention when the pin 52 is engaged with the anatomical feature 4 (e.g., a spinous process). The pin 52 may include a tool engagement feature 131 for engaging and retaining a tool, such as the spine tracker inserter 54 (shown in FIG. 9A) during installation of the pin 52 (FIGS. 9B and 9C). FIGS. 8B-8C illustrate the pin 52 engaged with the array 38.

In some embodiments of the system 10, a spinous clamp 124 is provided. The spinous clamp 124 serves to secure the array 38 with the anatomic feature 4 by clamping onto the feature 4 and providing an interface for releasably securing the array 38. The spinous clamp 124 may include a central body 132 that ends from an array end 134 of the clamp 124 to a clamp end 136 of the clamp 124. The clamp 124 may be symmetrical, as shown in FIG. 8D, or asymmetrical, as shown in FIG. 8E. The clamp 124 may comprise opposing first and second grasps 138, 140 that are configured to secure the anatomical feature 4, such as a spinous process. The grasps 138, 140 may be resiliently biased towards a first, closed position (as shown), and configured to translate to a second, open position by pivoting one or more wings 142 toward the central body 132. In the embodiment shown in FIG. 8D, the pivoting of the wings 142 causes laterally disposed arms 144 to translate, transitioning the grasps 138, 140 from the first position to the second position. The arms 144 may be contoured, such as continuously tapering inward toward their center, such as to minimize obstructing the view of the surgical area to the surgeon. The grasps 138, 140 may each include a plurality of spikes 146 to increase the grip between the grasps 138, 140 and the anatomical feature 4. At the array end 134 of the clamp 124, the clamp 124 may include an array orientation feature 148, such as a flat surface on the central body 132, to ensure that the array 38 is correctly clocked when engaging the array 38 with the clamp 124. The clamp 124 may include a driver retention element 150, such as a notch, to ensure that the clamp 124 is retained in a tool, such as the spine tracker inserter 54, during installation of the clamp 124 on the anatomical feature 4. The central body 132 may include radiographic glyph elements 78 and distal radiographic glyph elements 126.

As shown in FIG. 8E, the clamp 124 may be asymmetrical. The asymmetrical clamp has grasps 138, 140 that are a first jaw 152 and a second jaw 154, respectively. The first jaw 152 may be mobile, and the second jaw 154 may be fixed relative to the central body 132. The mobile first jaw 152 may be resiliently biased in a first, closed position. The mobile first jaw 152 may be hingedly connected with a support 156. The support 156 is in turn connected to a biased member 158. The biased member 158 may be disposed around the central body 132 and between two biasing members 160, such as springs, that retain the biased member 158 in the first, closed position. When the biased member 158 is translated along the central body 132, the biased member 158 translates the support 156, which in turn causes the mobile first jaw 152 to pivot to the second, open position, converting the translation movement of the biased member 158 to pivotal movement of the first mobile jaw 152. The biasing members 160 may be disposed around the central body 132.

Figure 10:
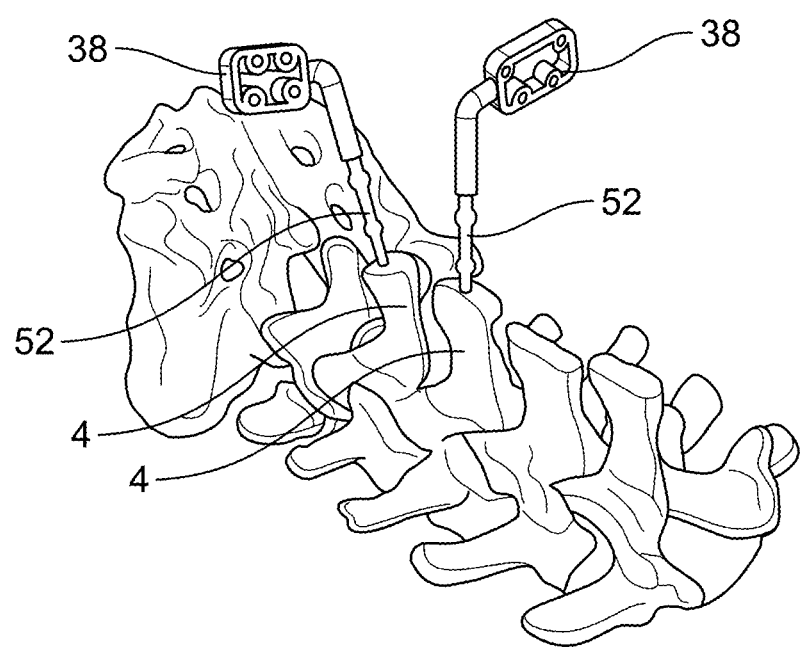
FIG. 10 illustrates arrays and spine pins removably secured with a spine of a patient.
Figure 11D:
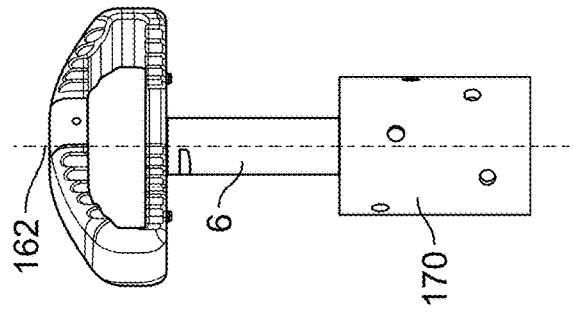
FIGS. 11A-11H illustrate an instrument with an integrated 360 degree variously rotated around an axis according to an embodiment of the navigation system.
Figure 11H:
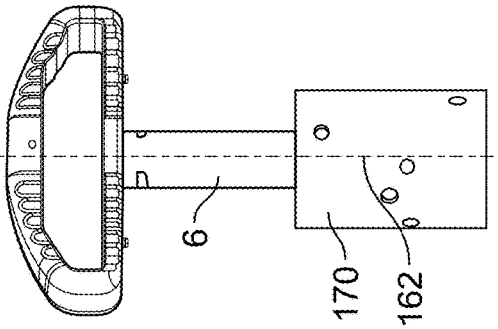
Figure 11C:
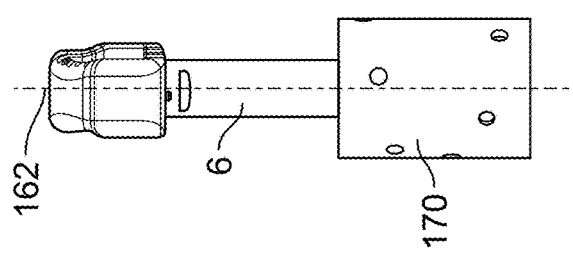
Figure 11G:
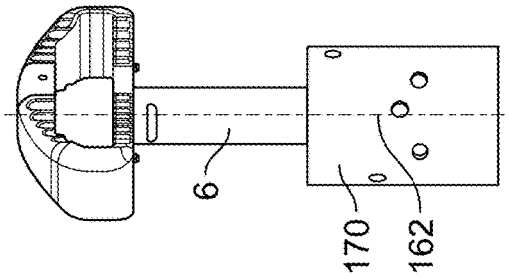
Figure 11B:
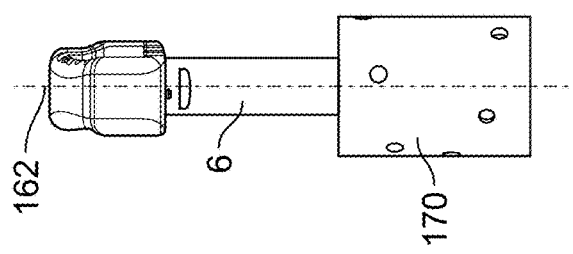
Figure 11F:
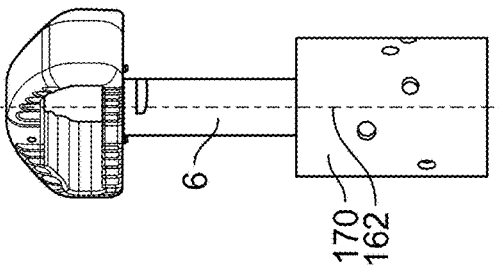
Figure 11A:
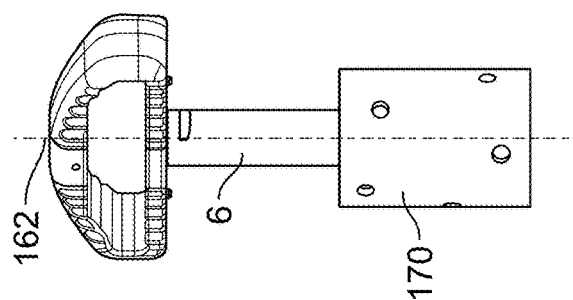
Figure 11E:
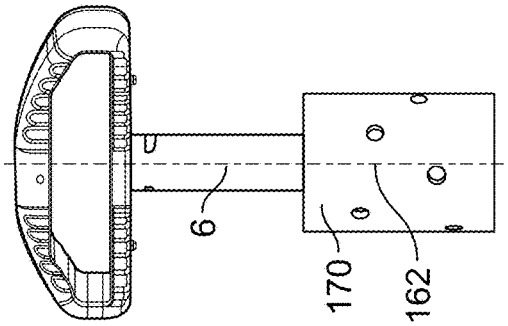

FIG. 10 illustrates spine pins 52 coupled to arrays 38 in accordance with an embodiment of the system 10. As can be seen, left handed and right handed arrays 38 can be moved away from the operative corridor, advantageously allowing the surgeon unrestricted, or less restricted, access, while still maintaining tracking capabilities of the arrays 38. The arrays 38 of the present disclosure are especially useful when coupled with instruments 6, as the pattern of the markers 42 on the arrays 38 allow the tracking system 10 to determine the position of the array 38, and thus the instrument 6, in 3D space as the instrument 6 is rotated. This is especially true for axially symmetric instruments 6 that are rotated during use, as the instrument 6 itself appears unchanged as it rotates along the axis 162.

While arrays 38 have been shown to be affixed to a mating feature through the connection portion 64 of the array 38 on the complementary surface 66 of the spine pin 52, it is contemplated that any of the arrays 38 may be adapted to be affixed to a mating feature on the distal end of the surgical instrument 6 in a similar fashion.

FIGS. 11A-11H illustrate the proximal end of an axially symmetric surgical instrument 6 in various rotational positions around an axis 162 according to a fifth aspect of the present disclosure. The instrument comprises a handle 164 at a handle end 166 of the instrument 6. A shaft 168 extends from the handle 164 to a cylindrical array 170. The cylindrical array 170 includes a plurality of recesses 172. The recesses 172 may be uniquely patterned around the cylindrical array 170, as shown, and may be configured to at least partially receive the markers 42. As the instrument rotates 6 (as shown in FIGS. 11A-11H), at least three recesses 172, and thus associated markers 42, remain visible to the cameras 34, 36 so that the system 10 can identify the spatial position of the array 38 and its associated instrument 6. According to some embodiments of the system 10, the recesses 172 are configured so that the 3D center of the visible marker area remains stable as the cylindrical array 170 is rotated.

Figure 12A:
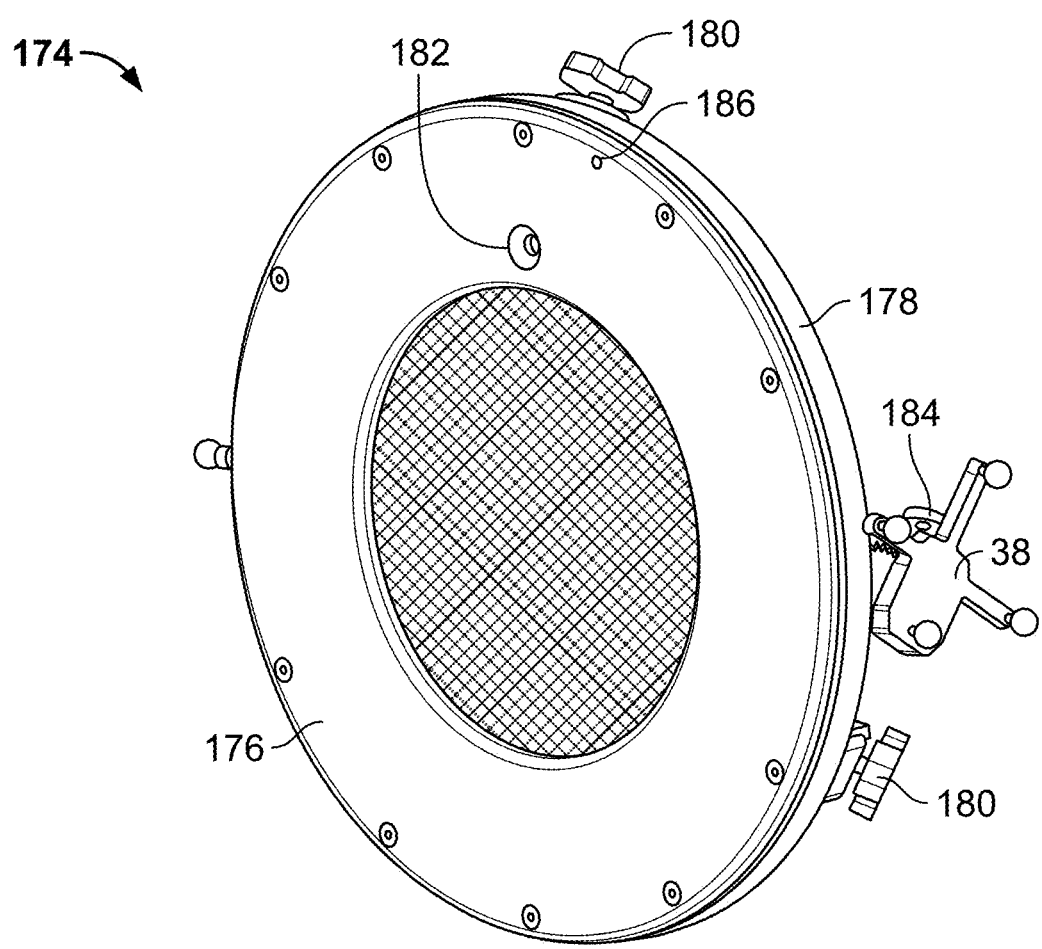
FIG. 12A illustrates a C-arm array mount according to an embodiment of the navigation system.
Figure 12B:
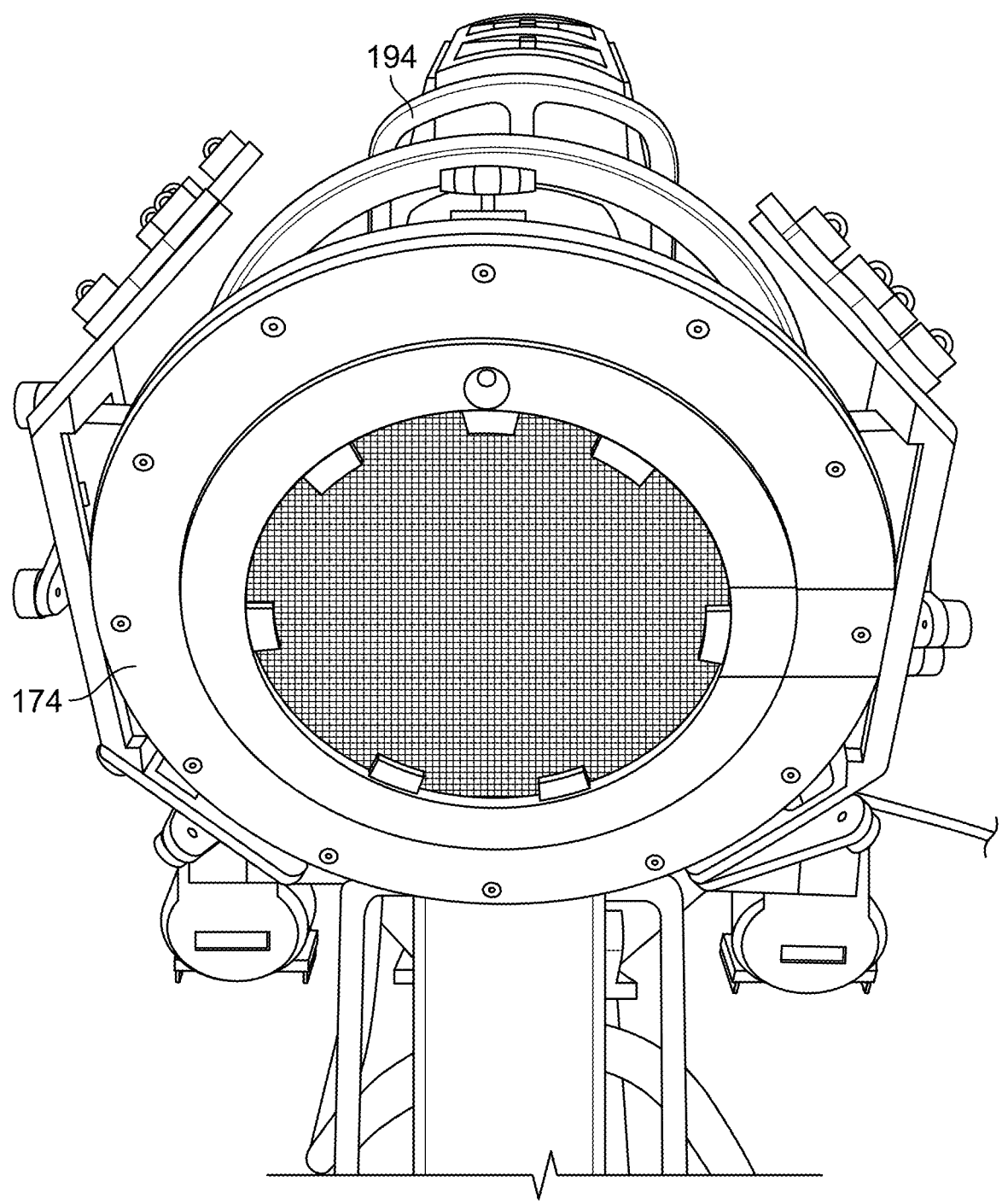
FIG. 12B illustrates the C-arm mount array of FIG. 12A mounted to a C-arm.

Referring to FIG. 12A-12B, a sixth aspect of the system 10 includes a C-arm array mount 174. The C-arm array mount 174 may be configured to attach to a C-arm 194 receiver end), such as commercially C-arms sold by GE OEC (9800 and 9990 series), Philips (Pulsera), Siemens (Arcadis), and Ziehm (Vision) which may be connected via a video cable (such as BNC cable) to the system 10. The C-arm array mount 174 may be constructed of a black polycarbonate glyph mount 176 operably connected to, or mounted to, a ring 178. The ring 178 may be constructed of, for example, aluminum. The mount 174 may include clamps 180, such as ring clamps, to pull a back face (not shown) of the glyph mount 176 so that the glyph mount 176 references the receiver end. The clamps 180 may press on an external perimeter of the receiver end casting, allowing the ring 178 to be positioned radially and rotationally so that a top most screw on the receiver end is centered (e.g., aligned) with a countersunk alignment hole 182 of the C-arm mount 174. The mount 174 may include an assembly alignment pin 186 for guiding the assembly of the glyph mount 176 with the ring 178.

The array 38 may be included into the array mount 174 at the back (i.e., opposite of the glyph mount 176) of the ring 178. The array 38 may include a mounting element 184, such as a thumbscrew, to secure the array 38 to the mount 174. The array 38 and the mounting element 184 may be constructed of a material(s) that enable them to be autoclaveable for repeated use between patients. Also beneficially, the present design avoids the use of specialized tools for installing or adjusting the ring 178 or the array 38. Thus, using the mount 174, the C-arm array mount 174 provides continuous line of sight from the array 38 to the navigation system 10, which can track the C-arm 194 in the vertical and horizontal orientations for all operative imaging levels. While a planar optical tracking array 38 is shown in FIG. 12A, it is contemplated that the 360 degree arrays 38 and 360 degree prismatic arrays 38 may also be utilized. The system 10 may utilize data from the sensed C-arm mount 174, enabling the use of hospital existing C-arms 194 and a calibration tool to accurately register pre-operative CT data sets to patients positioned for surgery in the OR.

With reference to FIGS. 26A-26D, registration plates (not shown) may be placed over the drape of the C-arm 194 so that the drape is engaged with the ring 178. A/P, +25, −25, and lateral images may be taken, received by the system 10, and the system 10 can execute the registration and calibration algorithms for the received images as will be described in greater detail below.

Figure 40:
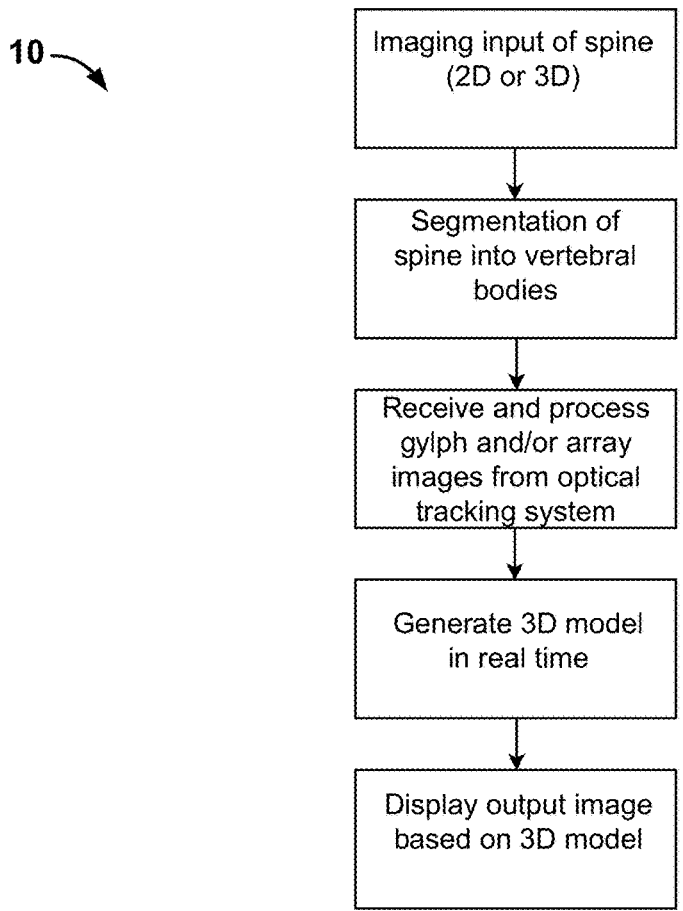
FIG. 40 is a flowchart that illustrates an embodiment of the navigation system.

In a seventh aspect of the system 10, and referring to FIG. 40, the system 10 includes computer executable instructions containing instructions to reconstruct 3D spine models from received imaging inputs (such as 2D and 3D medical images from pre-op and intra-op sources such as CT, CBCT, and MRI,) that are segmented into rigid bodies (e.g., vertebrae) based on tracked anatomical features 4. The computer executable instructions are configured to dynamically track and display each anatomical feature 4 in real time. The computer executable instructions of the system 10 are configured to track and correlate the real time location of surgical tools relative to each tracked anatomical feature. The computer executable instructions are configured to calculate and display a dynamic 3D spine model with streaming data of virtual tools overlaid over the displayed dynamic 3D spine model to augment direct anatomy visualization.

Figure 41:
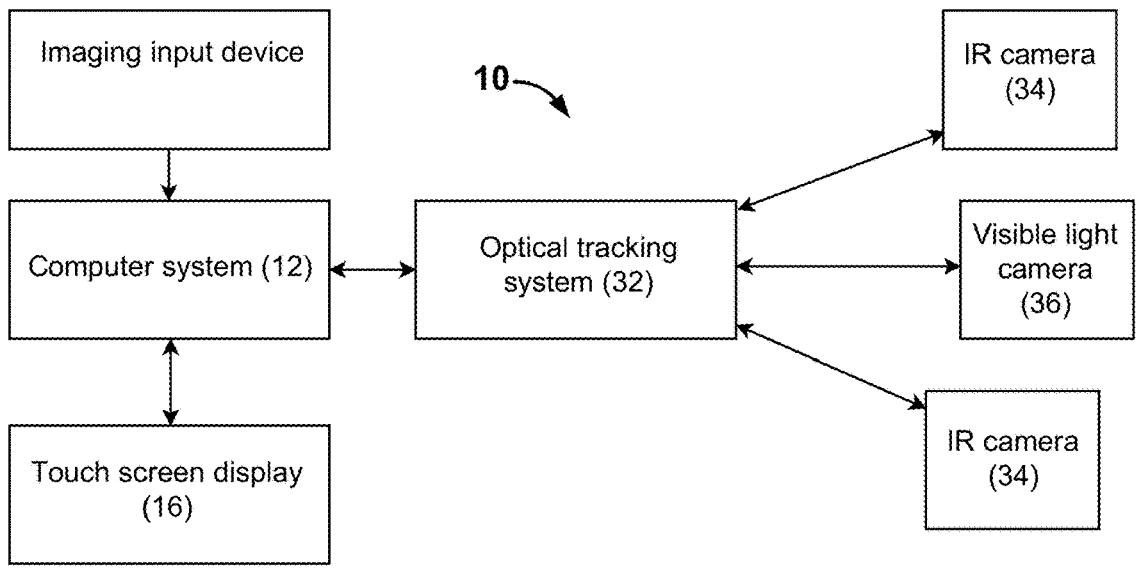
FIG. 41 is a block diagram that illustrates an embodiment of the navigation system.

As can be seen in FIG. 41, the imaging input device (e.g., pre-op and intra-op sources) is in communication with the computer system 12. The computer system 12 is in communication with the touch screen display 16, which can display data from the system 10 to the surgeon and receive input data from the system. The computer system 12 is in communication with the optical tracking system 32, including the IR cameras 34 and the visible light cameras 36. The computer system 12 may control the cameras 34, 36 (views, IR/visible light functionality, etc.), cause the cameras 34, 36 to capture and transmit images, and receive image data from the cameras 34, 36.

The computer executable instructions may be configured to execute a registration step. As used herein, the term "registration" is used to mean the correlation of one or more reference points of a virtual 3D data set with one or more reference points of the patient's current anatomical position. A registration step may be configured to occur for each receiving image source. In a preferred embodiment, the registration step includes parameters regarding the physical flexibility of the patient's spine. The registration step may vary according to the received image data. For example, if the received image data is from a pre-operative CT data set synced to one or more intraoperative 2D c-arm images, registration includes image recognition of one or more spine pins and one or more image markers within two fluoro images will register each vertebrae and reconstructing a 3D model from the pre-op 3D image. If the registration is of an intra-op CT/CBCT, image recognition of one or more spine pins within the intra-op 3D image will register each vertebrae. Meanwhile, if the image data is from an MRI-CT, imagine recognition of the CT image will merge MR images to each CT segment/vertebrae. In a fluoro-MRI registration, the instructions may be configured to register the 3D MRI image without any CT images.

The computer executable instructions of the system 10 may be configured to identify the spine pin 52. The computer executable instructions may be configured to sense the spine pin 52 and use the sensed spine pin 52 to scale the intraoperative radiographic image to register patient space, image space, and navigation space. The pins 52 may have glyph elements 78, 126 (e.g., spheres) that have a known predetermined diameter. When imaged by the cameras 34, 36, each glyph element 78, 126 has one or more characteristic identifiers in each imaging modality that can be leveraged by image recognition techniques (such as the known predetermined diameter).

Figure 13:
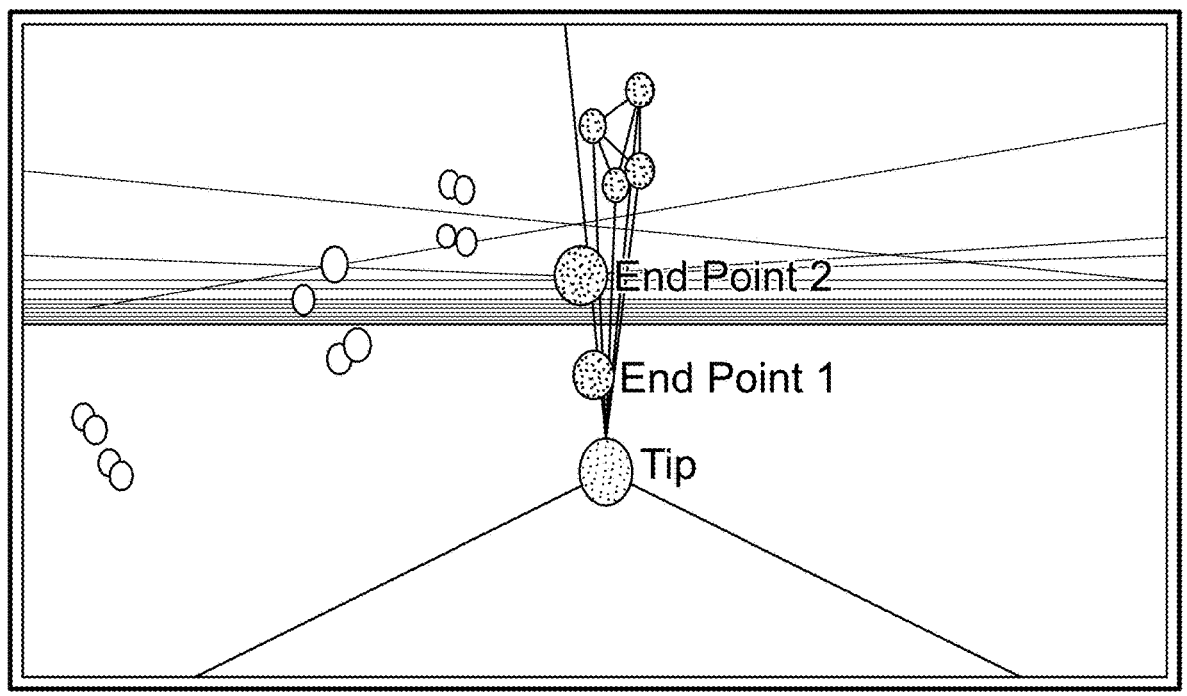
FIG. 13 illustrates calculations used to identify one or more spine pins from received images.
Figure 14C:
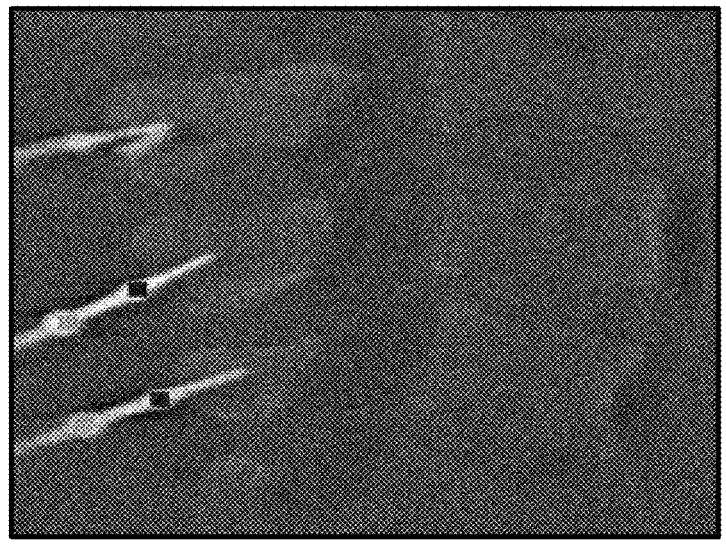
FIGS. 14A-14C illustrate images of a set of spine pins affixed to the spinous processes of first, second, and third vertebrae.
Figure 14B:
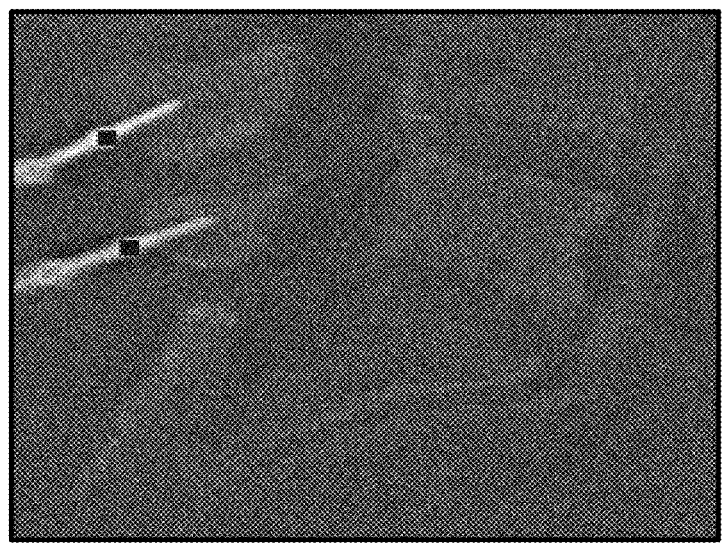
Figure 14A:
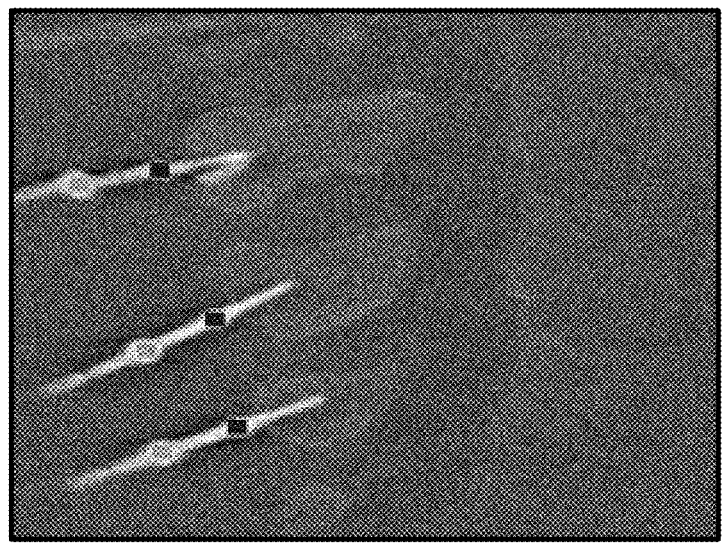

By way of example, for a CT, the imaged glyph element may have a characteristic of a halo around it that can be used to correlate the center of the radiographic halo to the center of the glyph element 78, 126. Also by way of example, for a fluoroscopic image, the imaged glyph element 78, 126 may be displayed as a black dot. The location of that center position may be restricted to an accuracy of a first 3D pixel (voxel). The addition of a second glyph element 78, 126 allows sub-voxel accuracy based on the known distance between the two glyph elements 78, 126 and the double halo (or double dot). When these imaged glyph elements 78, 126 are placed along a single axis, a five degree of freedom pin is generated. To generate all six degrees of freedom, a second pin 52 having five degrees of freedom may be located in the image so that the orientation of the spine may be determined. If it is desirable to use only one spine pin 52 and resolve all 6 degrees of freedom, a 6 degree of freedom spine pin 52 can be used which has at least two glyphs 78, 126 on a first axis and an additional glyph 78, 126 (e.g., a distal glyph 126) orthogonal to the axis of the pin 52. FIG. 13 illustrates calculations used to identify one or more spine pins 52 in an image. As can be seen in FIG. 13, using the positions and orientations in 6 degrees of freedom of the arrays 38, the computer executable instructions were configured to calculate the two glyph centers of each marker 42. FIGS. 14A-14C illustrate a set of spine pins 52 positioned within the spinous processes of three adjacent vertebrae identified in accordance with the method described herein. In some embodiments, the computer executable instructions may include image recognition configured to determine the geometric shape of the entire spine pin 52.

After the system 10 determines the orientation of the pin 52, whether in 5 degrees of freedom or six degrees of freedom, the computer executable instructions may be configured to determine a relative position for the pin(s) 52. The optical tracking system 32, through cameras 34, 36 can sense the arrays 38 coupled with the pins 52. If the pin 52 is a six degree of freedom pin 52 (e.g., has the distal glyph 126 in addition to a glyph 78), then only one array 38 is needed by the system for the computer executable instructions to determine the position of the pin 52. If the pin 52 is a five degree of freedom pin 52 (e.g., does not include the distal glyph 126), then two pins 52 and arrays 38 coupled with the pins 52 are required for the computer executable instructions to determine the directive of the spine relative to the cameras 34, 36. The optical tracking system 32 may be configured to sense left/right arrays 38 that are coupled to the pins 52, and the computer executable instructions may be configured to calculate a relative position for each pin 52 based on the sensed arrays 38. The computer executable instructions may be configured to compare the determined relative positions of the radiographic orientation of the pins 52 to confirm that they align within an acceptable error tolerance. One this correlation is confirmed by the system 10, any relative movement of the spine detected from the tracking system 32 can be used to update the segmented vertebra locations in the radiographic data. Moreover, as the tracking arrays 38 may have six degrees of freedom, even if the pin 52 has 5 degrees of freedom, one registration has been confirmed, all of the arrays 38 can be removed except the one that the surgeon desires to remain so that the operative area is unobstructed. Depending on surgeon preference, multiple spine pins 52 and arrays 38 may be left in place (i.e., connected to the anatomical feature 4) to show an indication of relative movement of the anatomical features 4 (individual vertebral bodies). If a traditional 3D radiographic view, similar to a CT, is preferred, the navigation system 10 can detect where the top of an instrument 6 is located and, based on the determined position of the anatomical feature 4, the system 10 can determine the most proximate vertebral body that is closest to the top, or intersecting the tip as a reference to determine the orientation of the 3D data set relative to the instrument.

The computer executable instructions may be configured to perform a segmentation step. As used herein, "segmentation" describes a process that identifies individual vertebrae within 3D image data so that the vertebrae can be separated and treated, manipulated, and displayed distinct from one another. The segmentation step may employ a segmentation algorithm that uses imaging processing and image recognition software to automate the spinal level segmentation process. FIG. 15 depicts a segmentation process where the computer executable instructions automatically identify and extract the spine curve, then detects and identifies each individual vertebra, until they are segmented from one another. One or more adaptive meshes may be applied to generate a segmented 3D model of the spine. Each vertebra or other anatomical feature 4 can be separately colored to visibly enhance the bone-soft tissue interface, or just the margin can be colored.

The computer executable instructions of the system 10 may be configured to perform segmental tracking. As used herein, "segmental tracking" refers to the ability of the system 10 to track each vertebra that is of clinical significance. Advantageously, segmental tracking includes a single registration even during the procedure, increased accuracy, and allowing the surgeon to continue to navigate while the spine moves during the placement of, for example, interbody implants, without losing accuracy of the tracking.

The computer executable instructions of the system 10 may be configured to perform 3D-2D image registration. As used herein, "3D-2D image registrations" refers to the receiving a 2D image (fluoro), calibrating the 2D image, and registering the location of the patient's anatomy to the 3D image (pre-op CT) while the patient is positioned for surgery using at least two perspectives. Using the 2D image, the 3D image can then be registered with the navigation system 10. The 3D-2D image registration may include a step of receiving a pre-operative CT into the system 10. The computer executable instructions may be configured to segment the vertebrae into individual levels from the CT model using a segmentation algorithm. FIG. 16A illustrates a CT model of a spine, and FIGS. 16B and 16C illustrate the segmenting out of three spinal levels of the spine of FIG. 16A. The computer executable instructions can extrapolate and generate, by a digitally reconstructed radiograph (DRR) algorithm, a set of 2D images based on the 3D CT model.

Figure 17A:
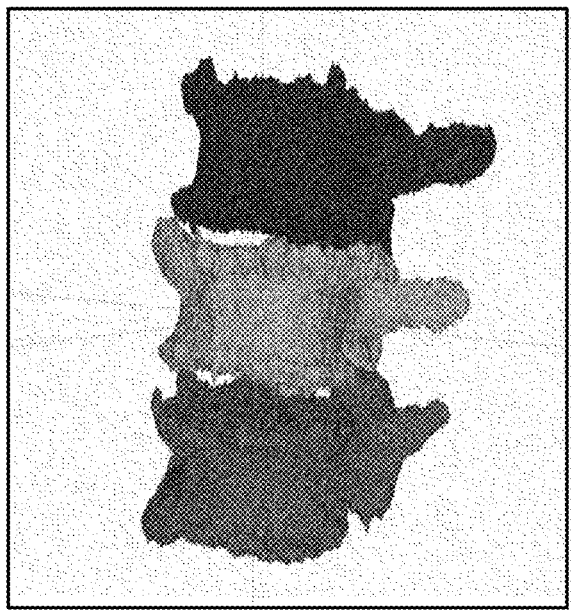
FIGS. 17A-17D illustrate a segmented 3D image set and various 2D DRR views of the segmented 3D image set according to an embodiment of the navigation system.
Figure 17B:
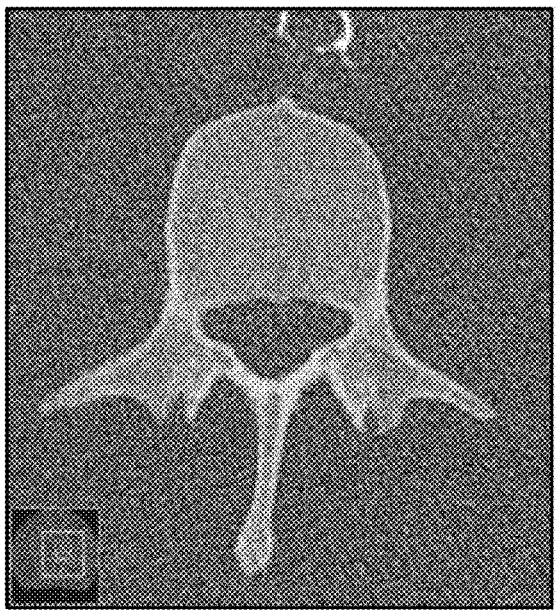
Figure 17C:
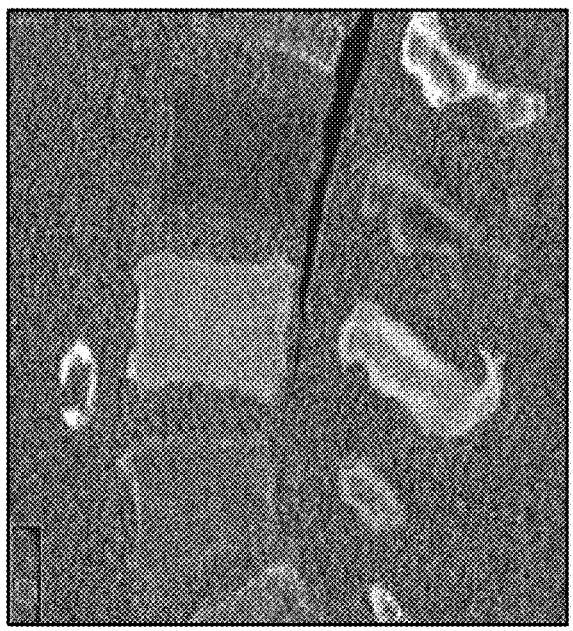
Figure 17D:
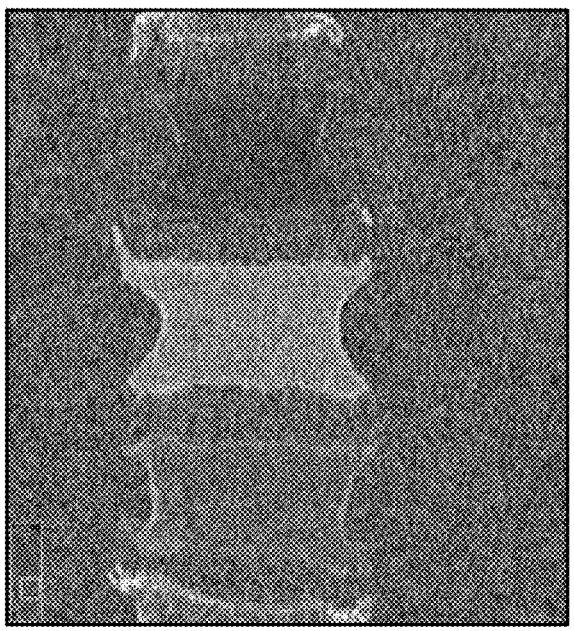
Figure 18A:
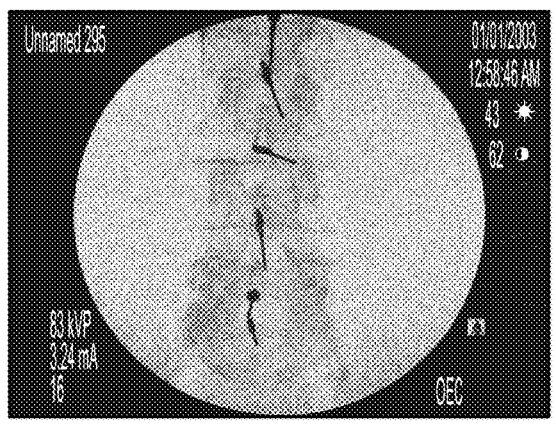
FIGS. 18A and 18B illustrate images with a set of spine pins affixed to the spinous processes of first, second, third, fourth, fifth and sixth vertebrae captured by a C-arm according to an embodiment of the navigation system.
Figure 18B:
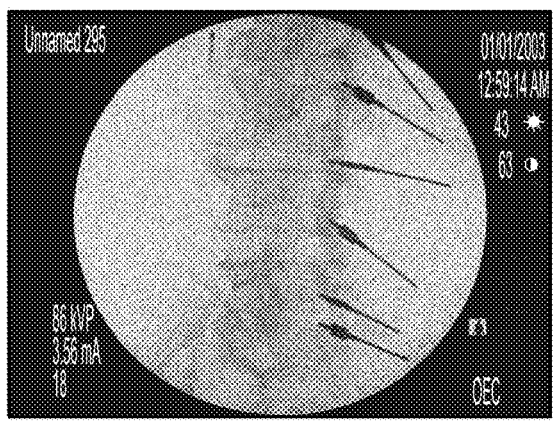

FIG. 17A illustrates a segmented 3D image data set. FIG. 17B illustrates a 2D DRR (axial view) of the 3D image data set. FIG. 17C illustrates the 2D DRR (sagittal view) of the 3D image data set. FIG. 17D illustrates the 2D DRR (coronal view) of the 3D data set. When spine pins 52 are inserted into the vertebral levels of interest, which can be done under fluoroscopic visualization using the C-arm 194, the geometry of the glyphs elements 78, 126 of the spine pins 52 provide the system 10 with the scaling necessary to register the patient space, image space, and navigation space, as discussed above. A C-arm 194, which may be tracked by the navigation system by the C-arm array mount 174, captures at least one image of at least one of the vertebral levels of interest in at least one view. The computer executable instructions may be configured to receive the at least one image. Exemplary images captured by the C-arm 194 are depicted in FIGS. 18A and 18B. In some embodiments, the registration can be verified. By way of a first example, using automated image processing and automated image recognition, the computer executable instructions may search, via an imaging algorithm, each generated segmental DRR to determine a match of a 2D representation of the 3D image data set with the image of the 2D intraoperative fluoroscopic image. By way of example, the algorithm may determine the match by a cross correlation value (via a similarity score) that exceeds a predetermined value in two views to result in a single solution. By way of a second example and with reference to FIGS. 27A-27D, a successful registration may show the DRR (e.g., a simulated C-arm shot) superimposed over a real C-arm image. Each level may be identified in a four shot C-arm series window and may show a green border over any images that align with 99.5% Z-score (or other predesignated level). Unregistered levels may not have a DRR associated (partial levels) to omit unnecessary information. The GUI may display a confirm button for each image that the surgeon can select to verify the registration. In some embodiments of the system 10, at least two verifications (of two images) must be performed to progress to the navigation screen of the GUI. In FIGS. 27A-27D, FIG. 27C has failed the verification and FIGS. 27A, 27C, and 27D have passed the verification. Next, the computer executable instructions may be configured to adjust the model position of each vertebral body from the Pre-Op CT position to the current operative patient position.

Figure 25:
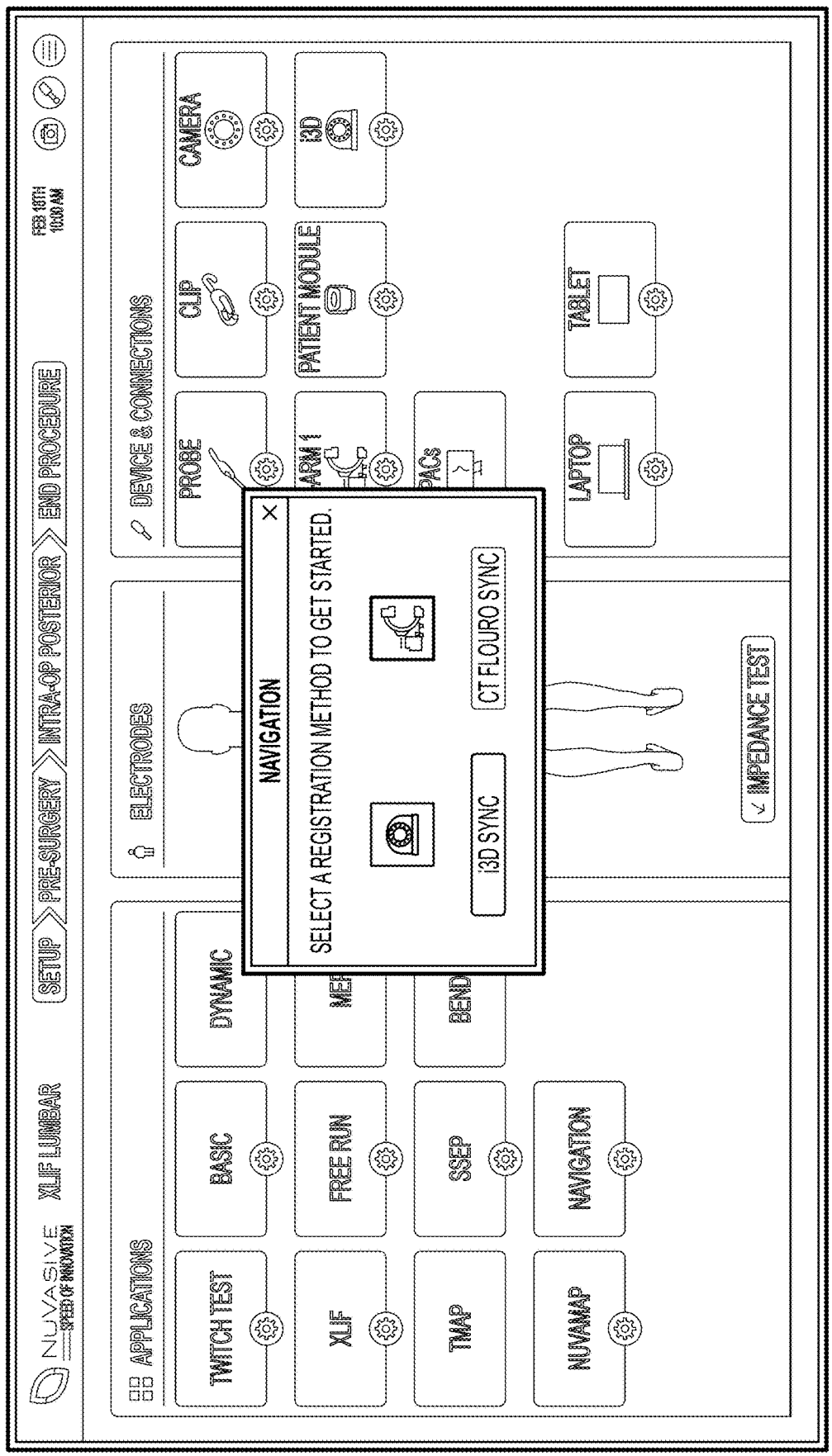
FIG. 25 illustrates a 2D-3D image registration menu screen displayed on a display screen according to an embodiment of the navigation system.
Figure 26A:
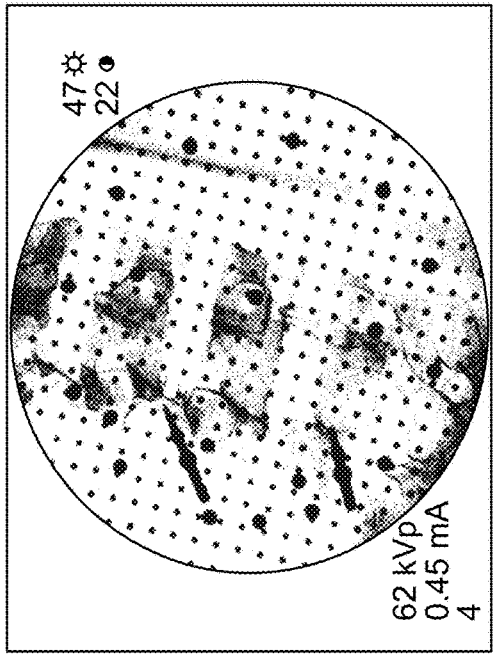
FIGS. 26A-26D illustrate a registration and calibration algorithm screen for the received images displayed on a display screen according to an embodiment of the navigation system.
Figure 26B:
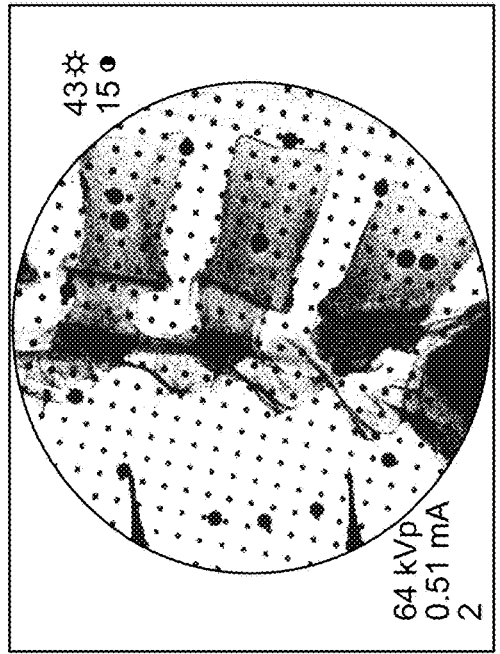
Figure 26C:
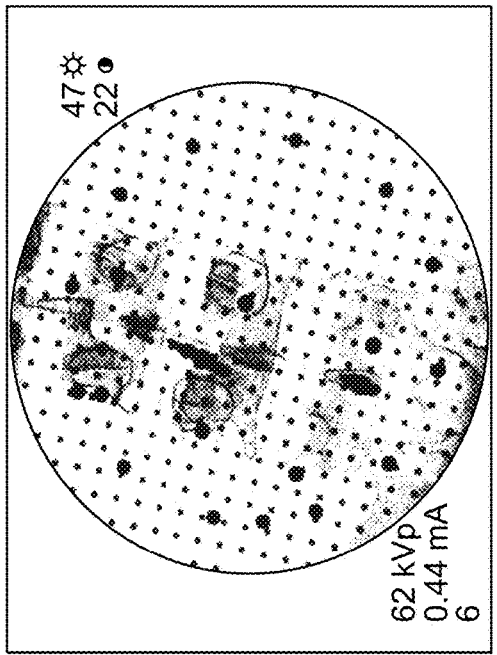
Figure 26D:
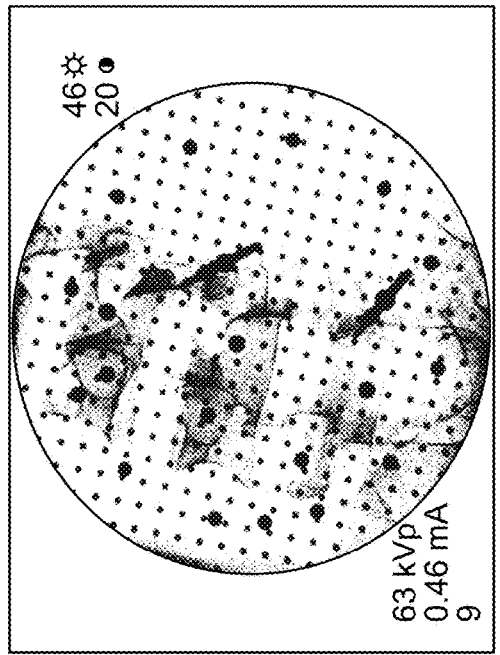
Figure 27A:
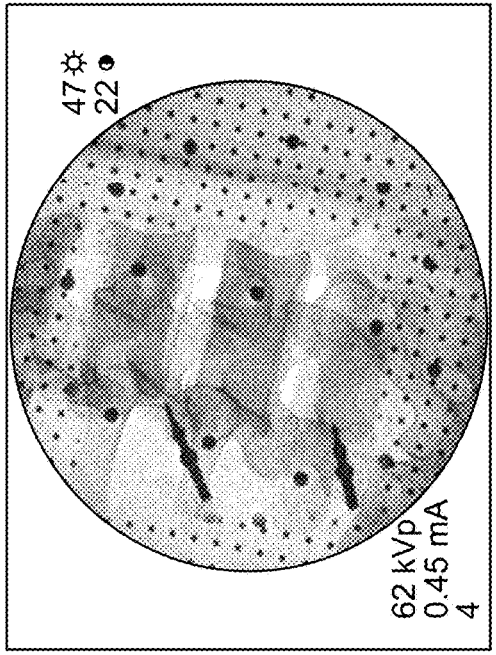
FIGS. 27A-27D illustrate a verification screen for the resulting registration determination displayed on a display screen according to an embodiment of the navigation system.
Figure 27B:
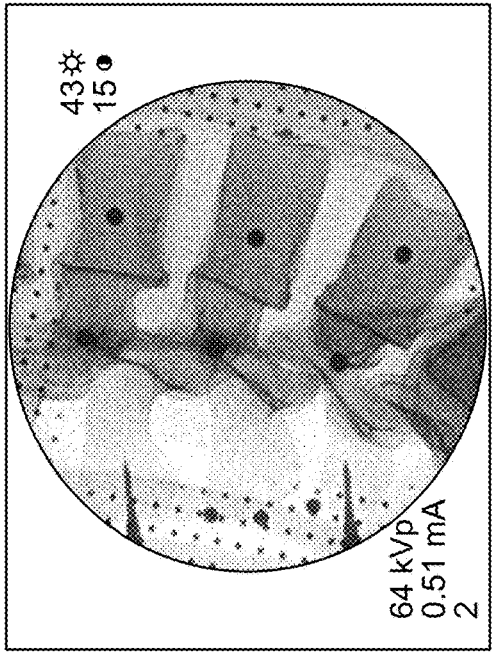
Figure 27C:
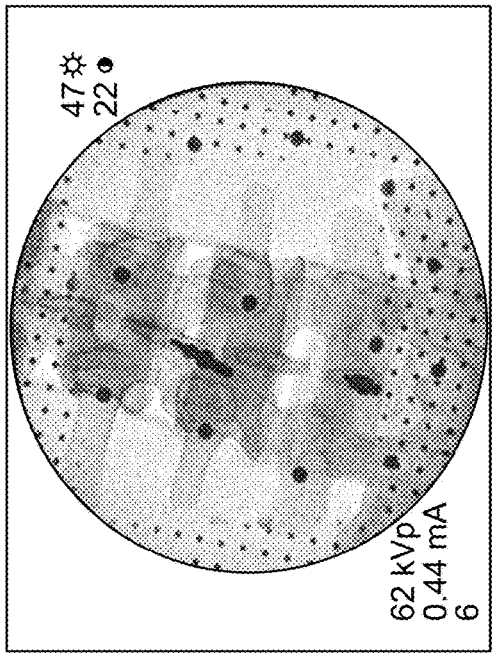
Figure 27D:
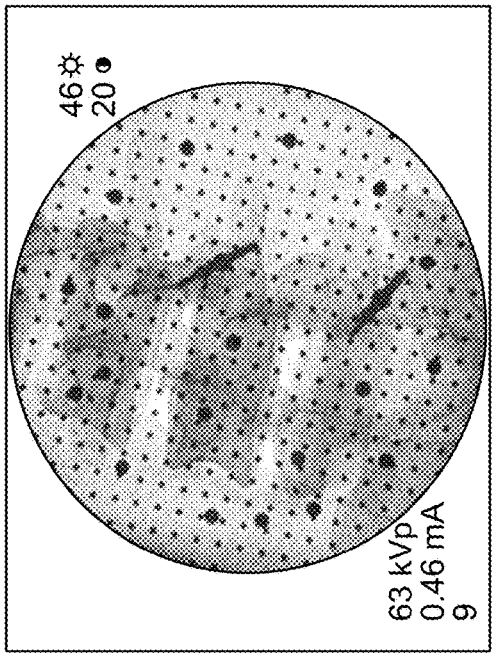

The computer executable instructions may be configured to cause a 3D-2D image registration menu screen to be displayed on the display screen 16 (FIG. 25).

Figure 28:
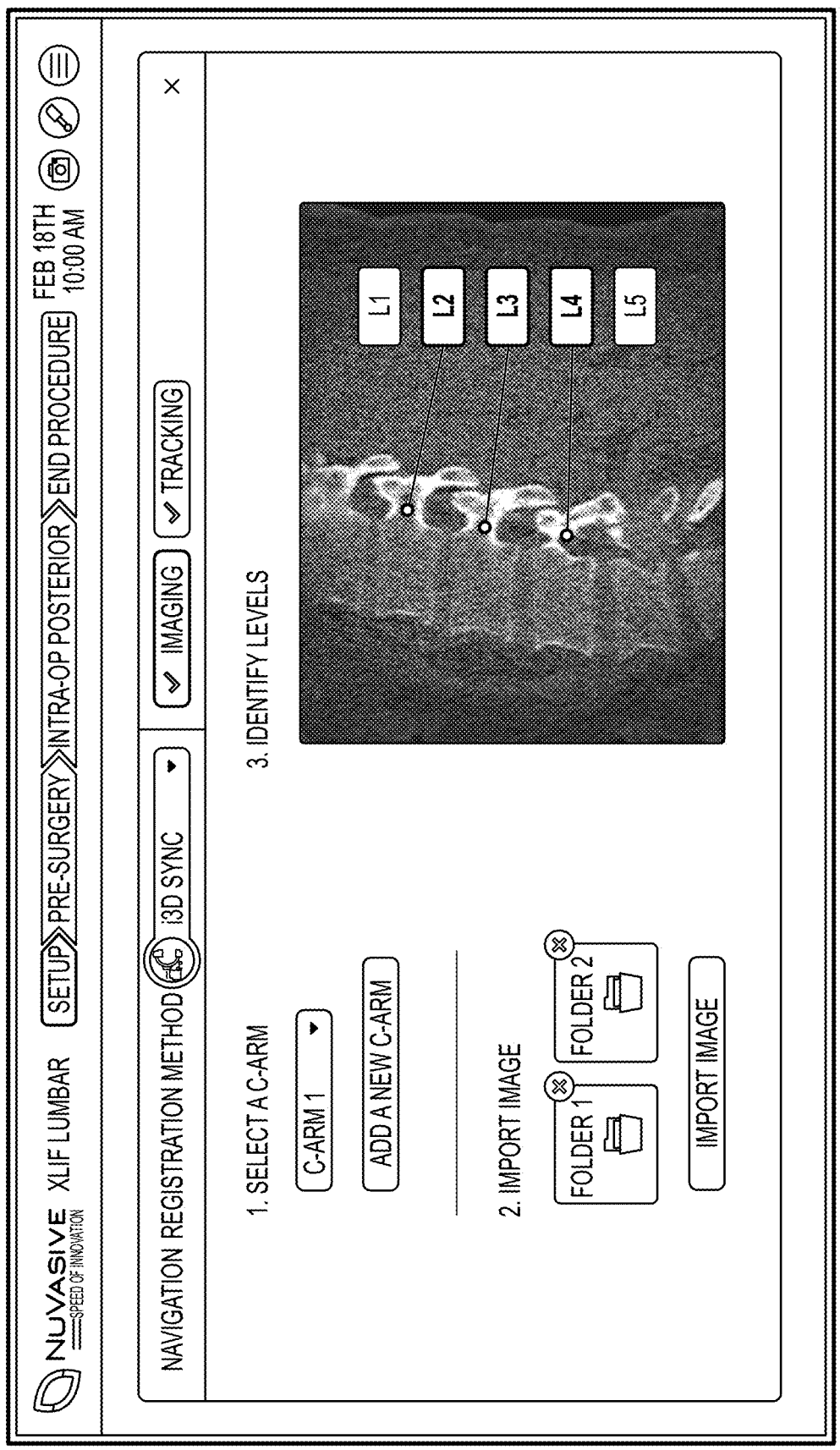
FIG. 28 illustrates a 3D-3D image registration menu screen displayed on a display screen according to an embodiment of the navigation system.

The computer executable instructions of the system 10 may be configured to perform 3D-3D image registration. As used herein, "3D-3D image registration" refers to the capturing and receiving a 3D intraoperative image and importing/registering the 3D intraoperative image with the navigation system 10. Spine pins 52 may be inserted into the vertebral levels of interest (such as under fluoroscopic visualization). As described above, the geometry of the glyphs elements 78, 126 of the spine pins 52 provide the computer executable instructions with the scaling parameters necessary to register the patient space, image space, and navigation space. Additionally, as the pins 52 are imaged in the intraoperative 3D image, the pins 52 (particularly the metal of the construction of the pins 52) serves as seed points to optimize the segmentation algorithm. Once segmentation is performed, the computer executable instructions cause the intraoperative 3D imager to capture image(s) of the vertebral levels of interest. The computer executable instructions are configured to receive the intraoperative 3D image from the intraoperative 3D imager, and the image of the spine can be segmented. In some embodiments, first the pins 52 are segmented from bone, and next, vertebrae are segmented into individual levels from the CT model using the segmentation algorithm. The computer executable instructions may be configured to cause a 3D-3D image registration menu screen to be displayed on the display screen 16 (FIG. 28).

The computer executable instructions of the system 10 may be configured to perform 3D MRI-2D image registration. As used herein, "3D MRI-2D image registration" refers to the capturing and receiving a 2D image (fluoro) and registering the location of the patient's anatomy (e.g., the anatomical features 4) with the patient is positioned for surgery using at least two different perspectives. The computer executable instructions may be configured to register, based on the 2D image, the location of the patient's anatomy. Advantageously, 3D MRI-2D image registration does not require a pre-op CT and can be used in facilities that lack 3D imaging equipment. Another benefit to MRI-2D image registration is the facilitation of soft tissue navigation, as the computer executable instructions may be configured to generate and display spatial awareness between soft tissues and instruments 6. For example, using the system 10 in embodiments employing 3D MRI-2D image registration, a surgeon can visualize and locate vessels and nerve roots for procedures such as XLIF to provide safe access to a surgical target site. The computer executable instructions may be configured to cause a 3D MRI-2D image registration menu screen to be displayed on the display screen 16.

Figure 19:
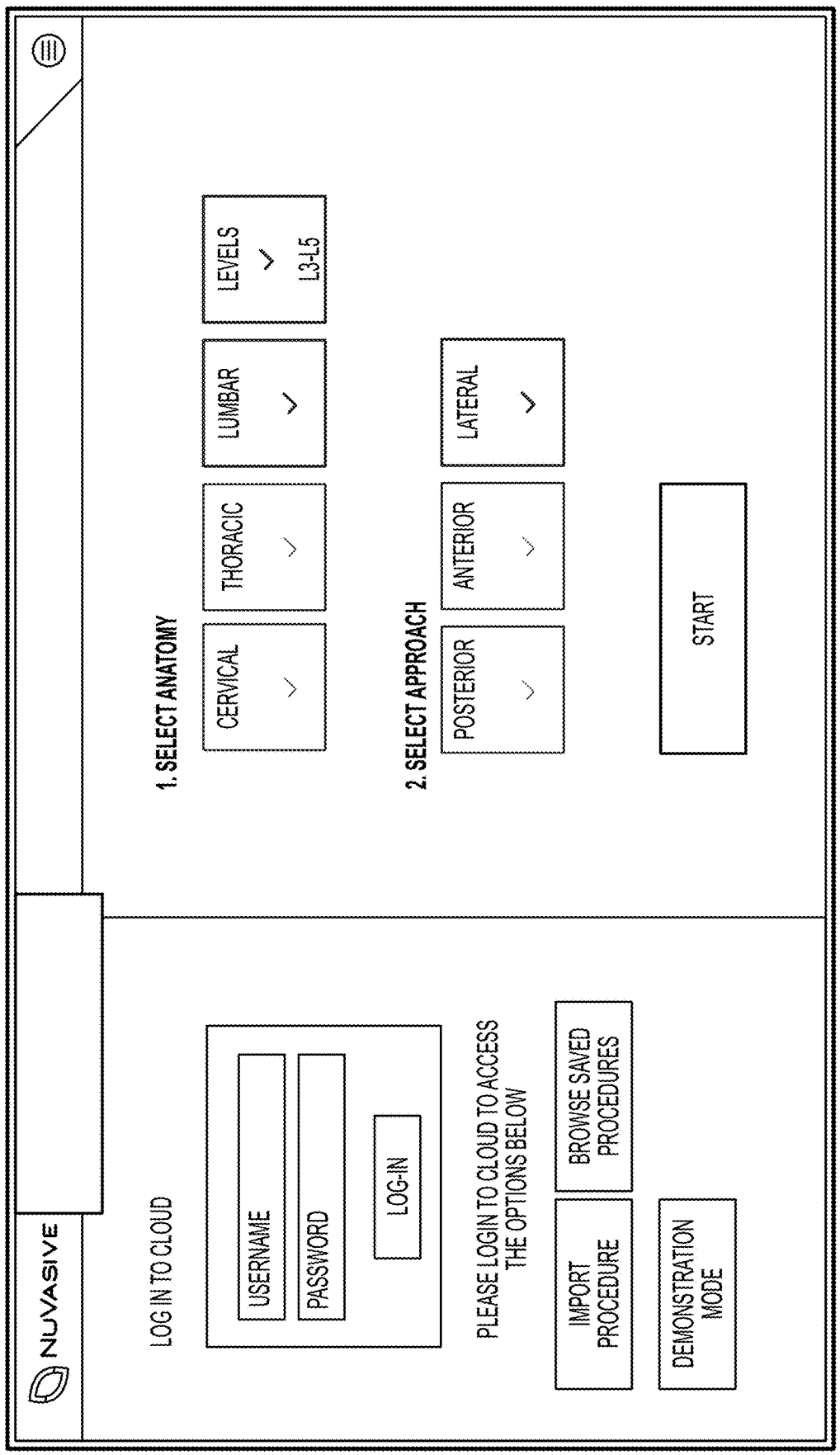
FIG. 19 illustrates a start-up menu on a display screen according to an embodiment of the navigation screen.
Figure 20:
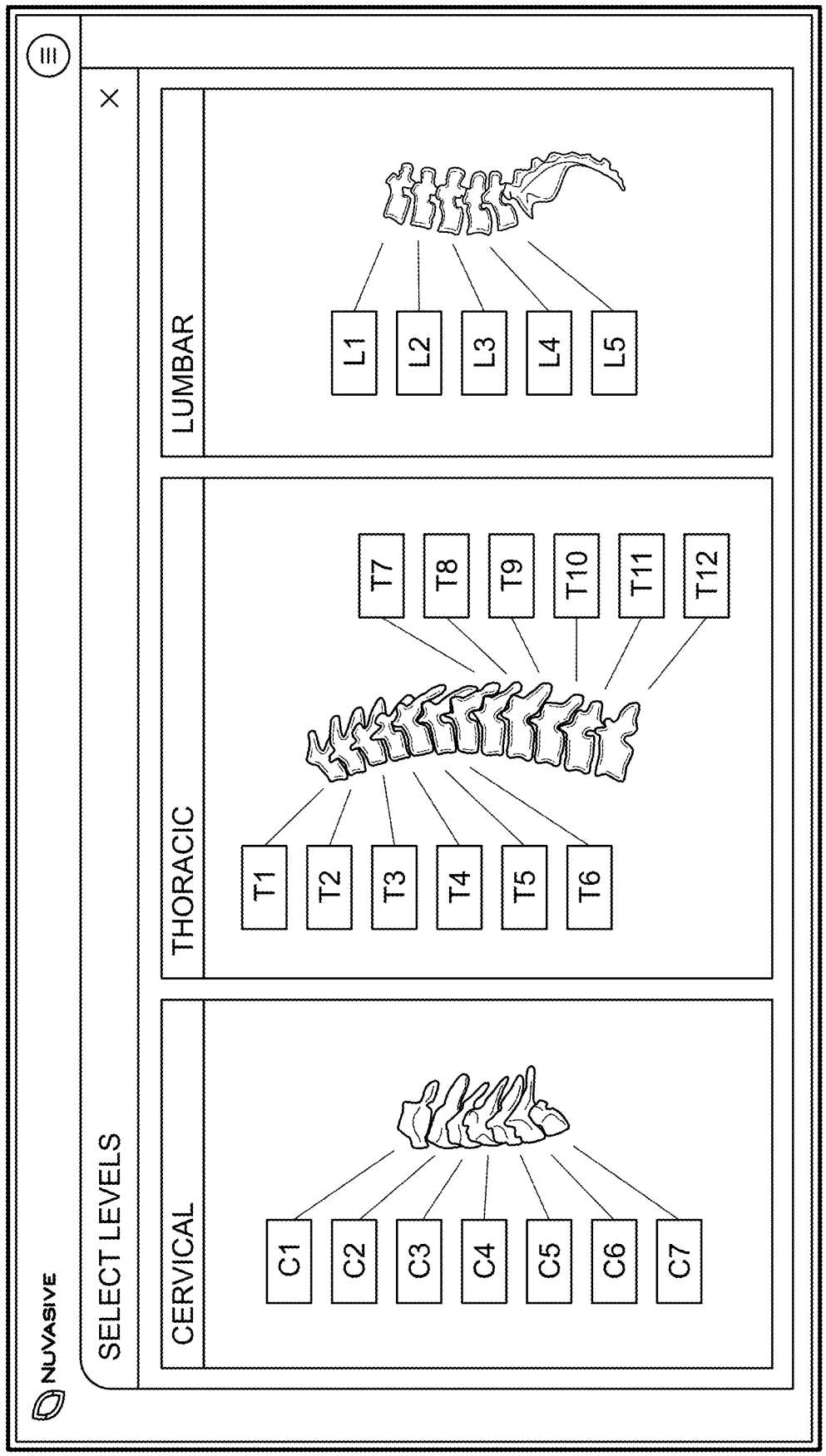
FIG. 20 illustrates a level selection menu on a display screen according to an embodiment of the navigation system.

The computer executable instructions of the system 10 may cause the display screen(s) 16 to display various workflow and visualization of the generated images utilizing the above described registrations. For example, some embodiments of the system may include computer executable instructions that cause "wizards" (step-by-step guided instructions) to display to surgeons to walk the surgeons through navigation setup and usage. FIG. 19 illustrates an example start-up menu screen GUI on the display screen 16. From the selection area, the surgeon may input case-specific information. For example, the surgeon may select the anatomical region that is the subject of the surgical procedure, the levels of the surgical procedure (e.g., the level selection menu screen shown in FIG. 20), and the surgical approach (e.g., posterior, anterior, lateral). In FIG. 19, the surgeon selected a lumbar procedure, levels L3-L5, from a lateral approach. Selecting a "start" button moves the surgeon to the next step in the workflow. As can be seen, the surgeon can also save procedures, import saved procedures, and enter "demonstration" mode for, for example, training or surgical planning purposes. The surgeon can also access settings and saved procedures through a secure login access to the cloud. It will be appreciated that any of the computer executable instructions contained herein may be in the cloud or locally stored in the navigation system 10 (such as by computer system 12).

Figure 21:
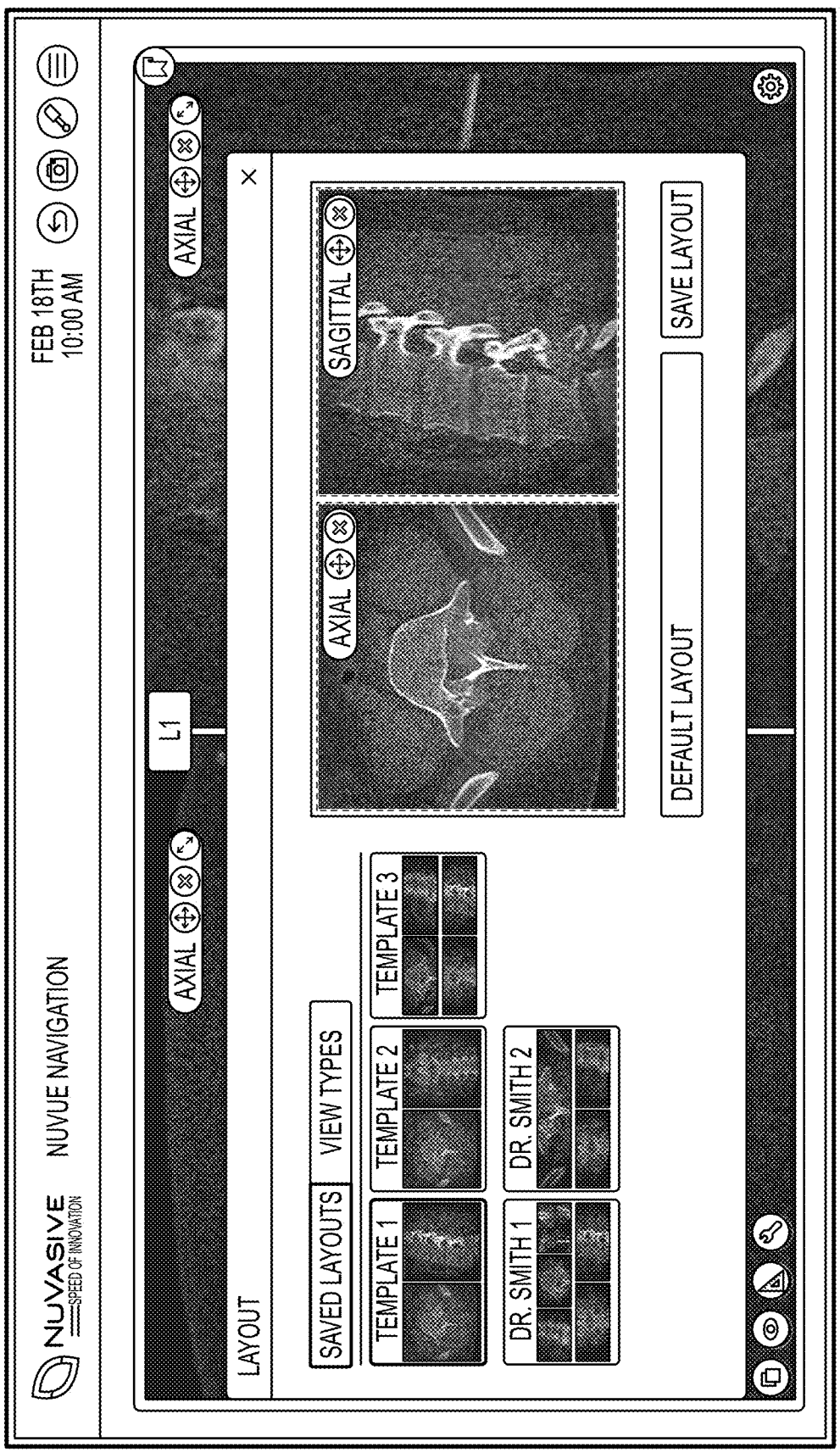
FIG. 21 illustrates a template and surgeon profile menu on a display screen according to an embodiment of the navigation system.
Figure 22:
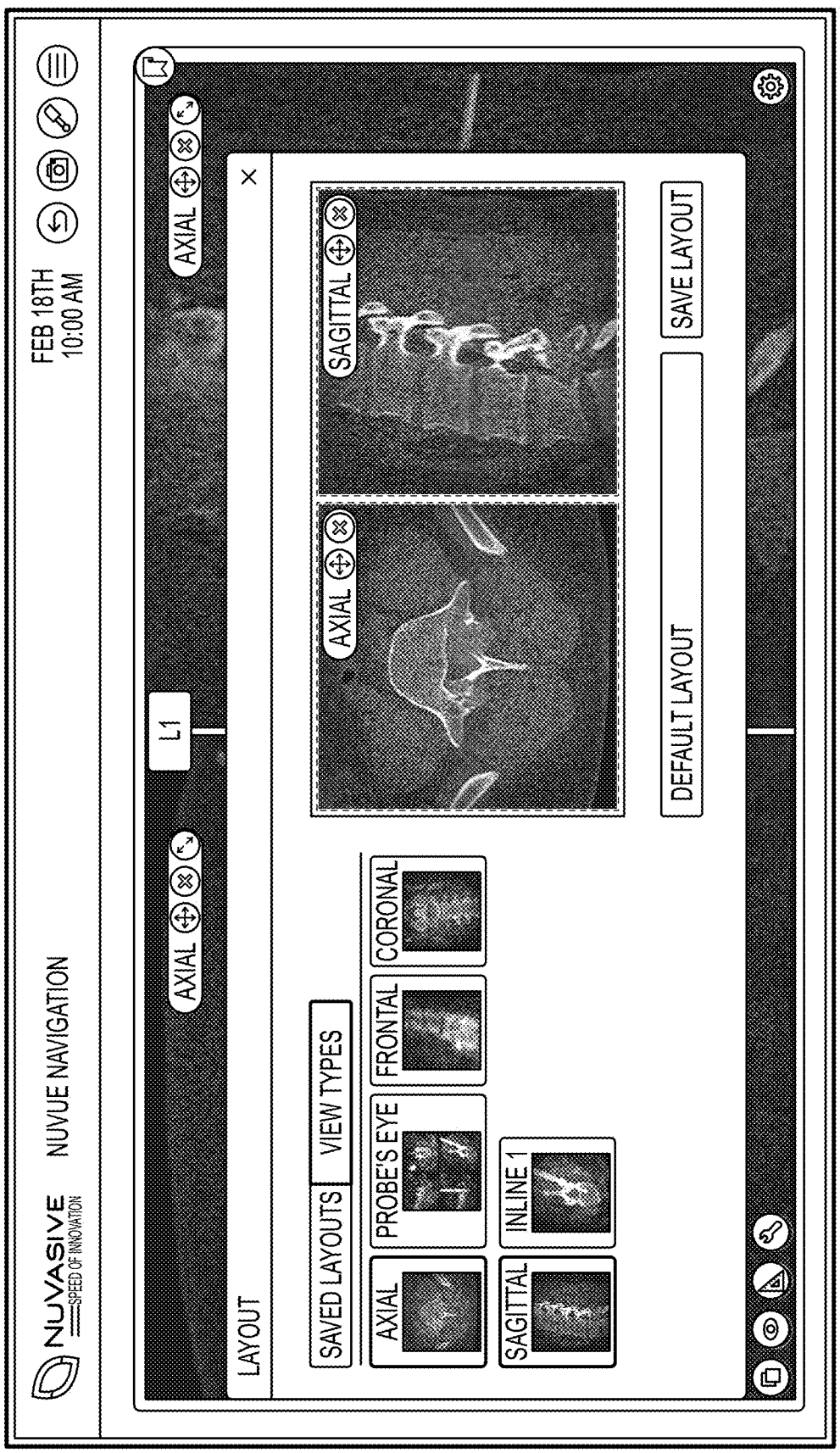
FIG. 22 illustrates a setup screen menu of stored templates on a display screen according to an embodiment of the navigation system.

The computer executable instructions may retrieve stored templates and surgeon profiles, such as templates for preferred views (e.g., axial, probe's eye, frontal, coronal, sagittal, inline, etc.) to streamline initial setup of the system 10 with a patient. The computer executable instructions may cause the display screen 16 to display a menu of the templates and surgeon profiles to the surgeon and receive template and surgeon profile selections from the surgeon, as shown in FIG. 21. FIG. 22 illustrates a setup screen menu where stored templates for preferred views are displayed on the display screen 16. The computer executable instructions may be configured to receive the selected templates selections from the surgeon.

Figure 23:
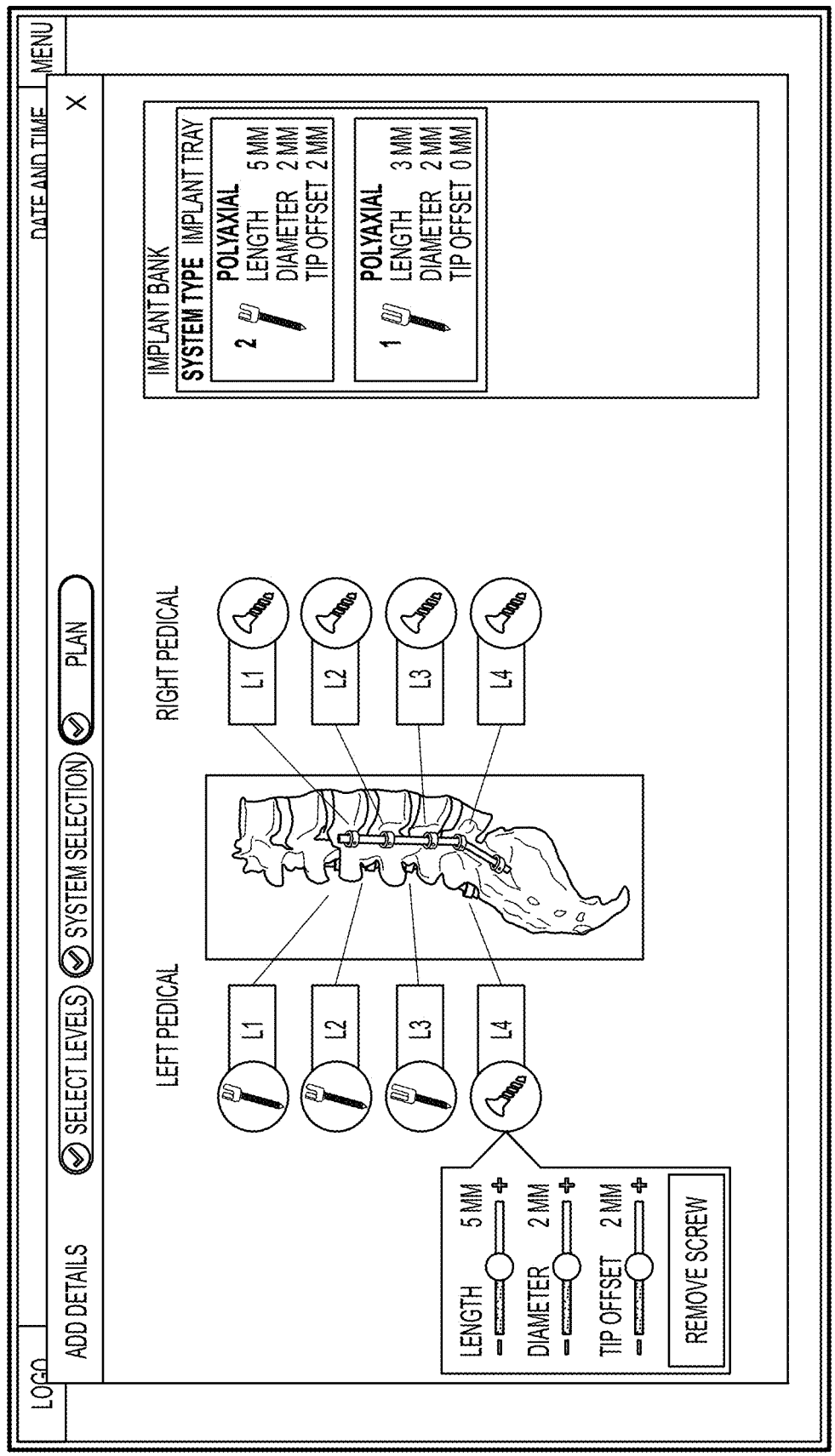
FIG. 23 illustrates a surgical planning screen displayed on a display screen according to an embodiment of the navigation system.

The computer executable instructions may be configured to enable the surgeon to load the pre-operative image data set and view, on the display screen 16, 2D and/or 3D image data for the purposes of planning the surgical procedure. FIG. 23 illustrates an example of a surgical planning screen displayed on the display screen 16. As can be seen in FIG. 23, the computer executable instructions may be configured to cause the display screen 16 to display a surgical planning menu where the surgeon (e.g., the surgeon or other OR personnel) can select the levels, screw types, and screw sizes for the surgical procedure.

Figure 24:
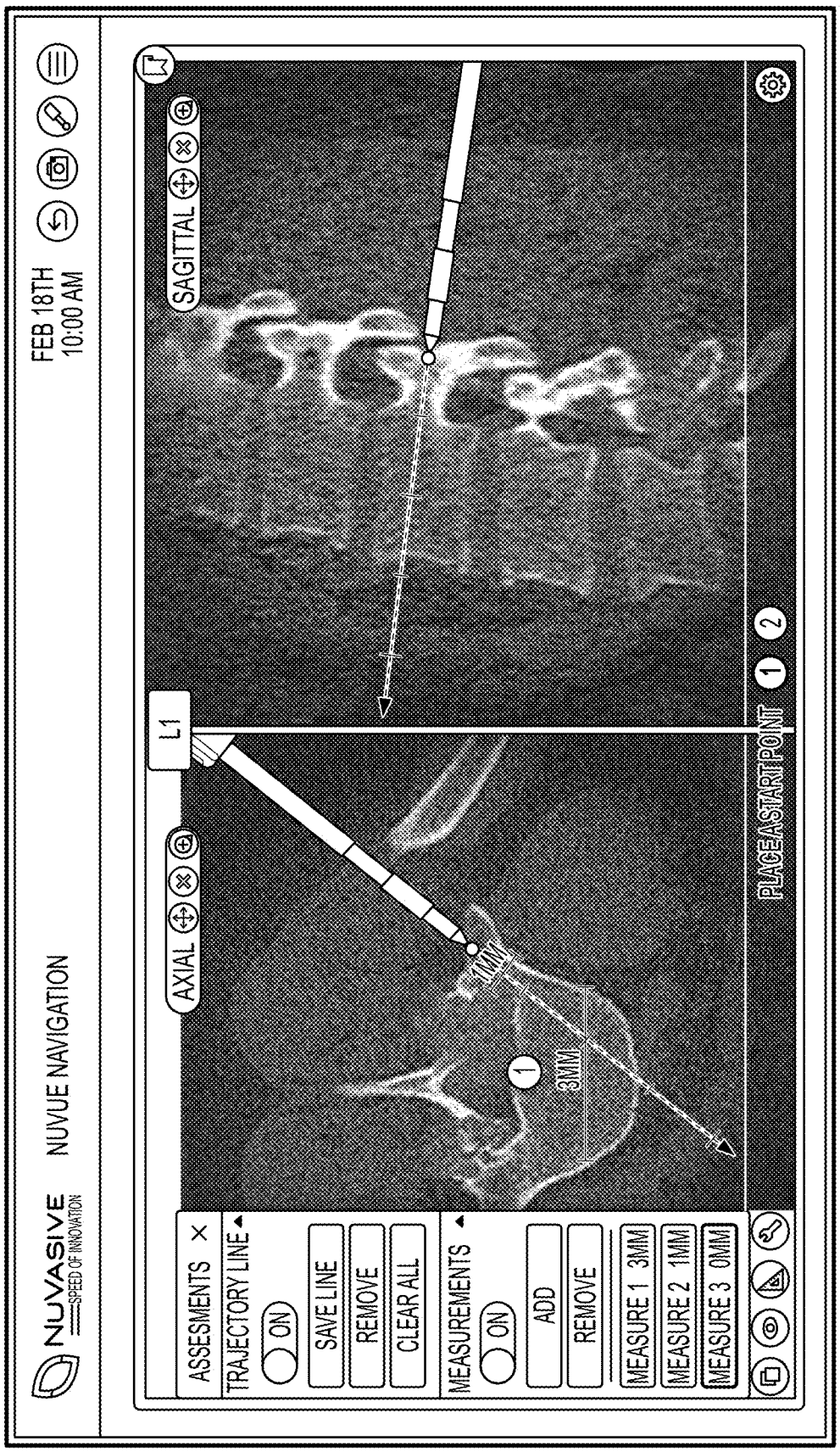
FIG. 24 illustrates another surgical planning screen displayed on a display screen according to an embodiment of the navigation system.
Figure 36A:
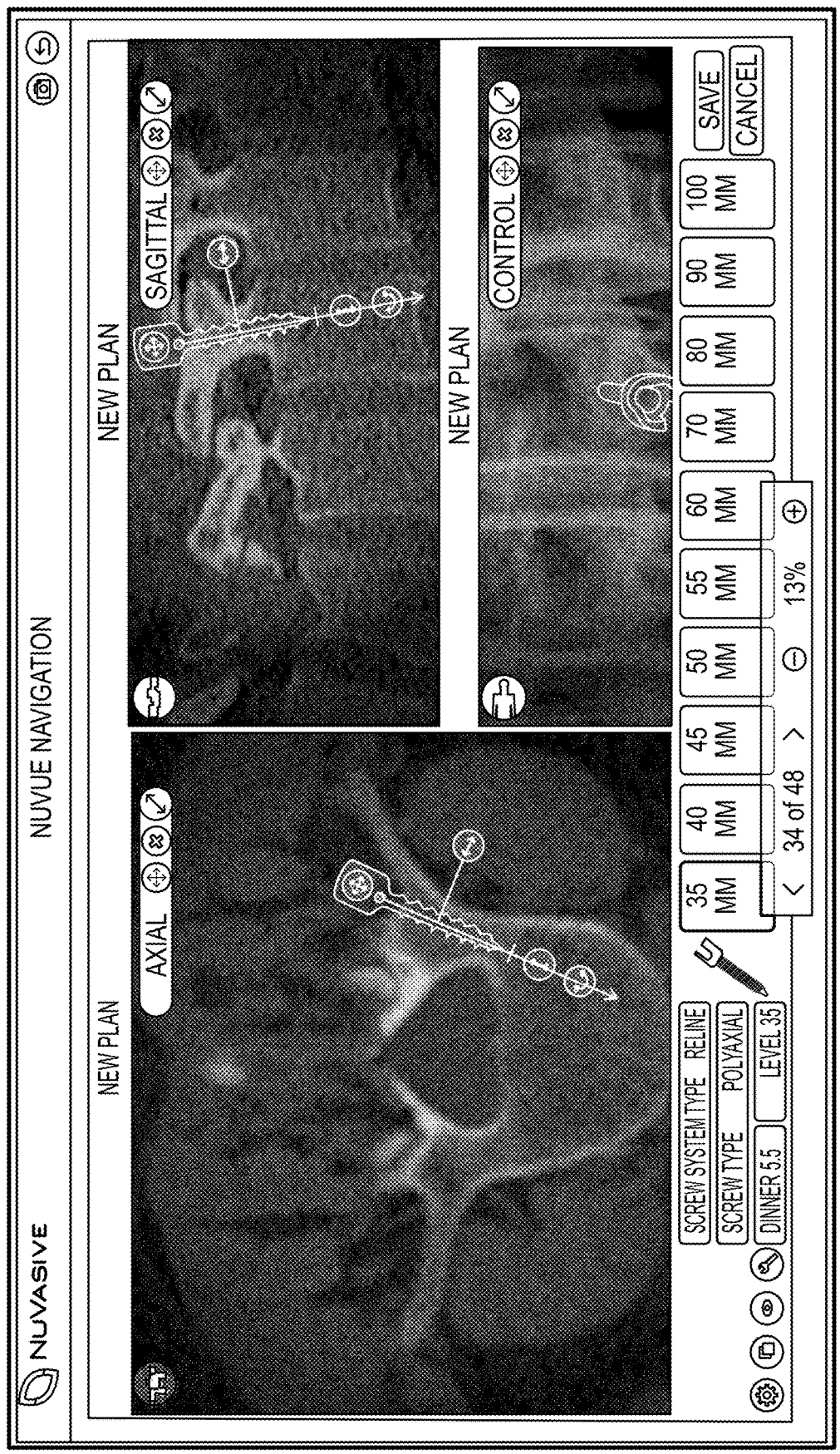
FIGS. 36A and 36B illustrate surgical plan menu screens displayed on a display screen according to an embodiment of the navigation system.
Figure 36B:
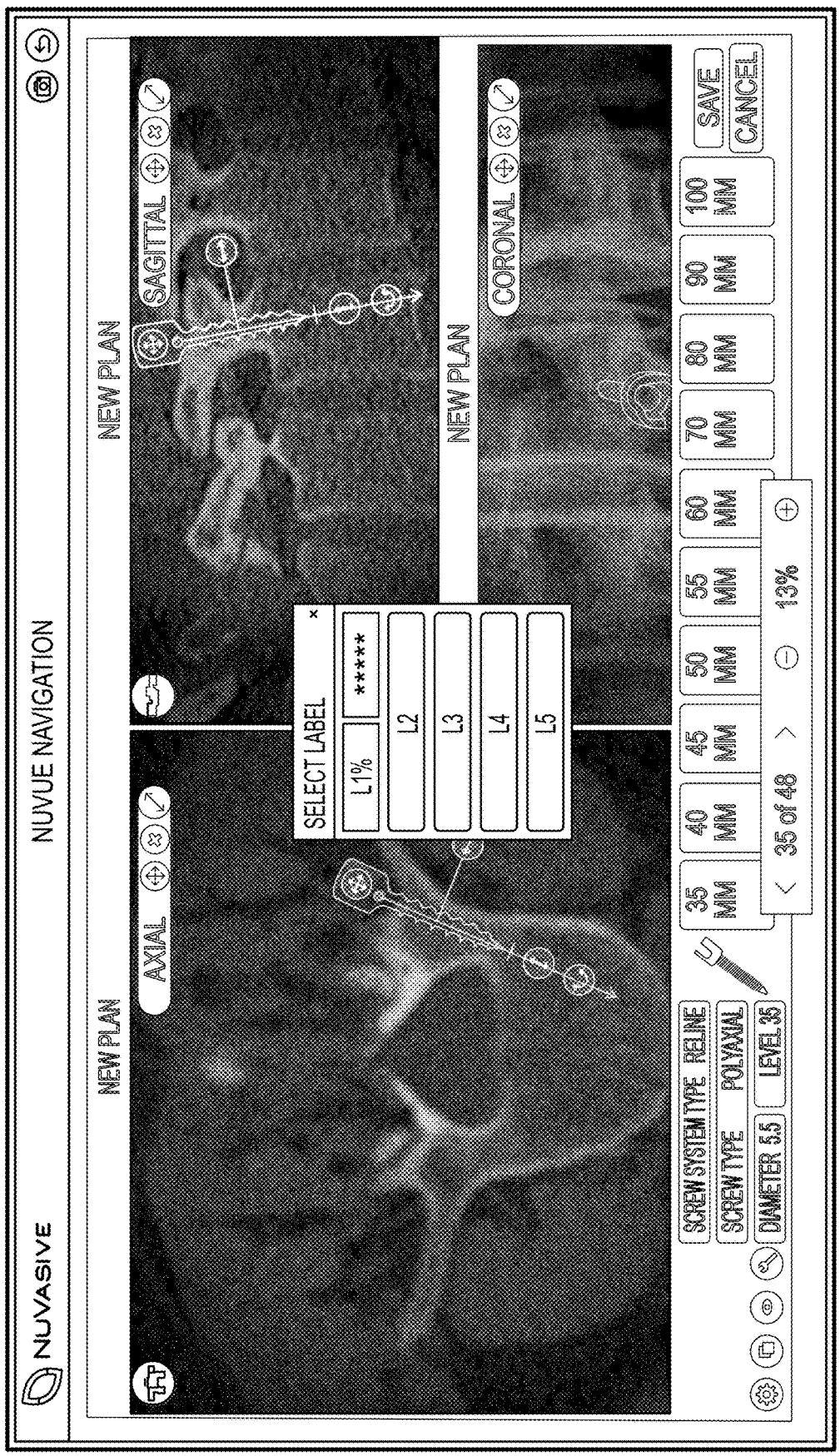

As can be seen in FIG. 24, the computer executable instructions may be configured to cause the display screen 16 to display a surgical planning screen where a surgeon can access a axial, sagittal, and coronal views of the pre-operative image data set, determine one or more anatomical measurements (e.g., pedicle width, vertebral body width or vertebral body depth), and propose a surgical trajectory. The surgical plan may be saved for each individual vertebral body plan so the system 10 may present a 3D or C-arm view(s) of the individual vertebra body plan during the appropriate time in the surgical procedure. With reference to FIGS. 36A and 36B, according to some embodiments of the system 10, screws may be placed in each pedicle according to best fit (either manually via surgeon selected or automatically by the system 10). The surgical plan may be saved for each individual vertebral body plan so the system may present a 3D or C-arm view(s) of the individual vertebral body plan during the appropriate time in the surgical procedure. As can be appreciated, other surgical planning types may be incorporated into the computer executable instructions, such as NuvaMap surgical planning software by NuVasive, Inc.

Figure 29:
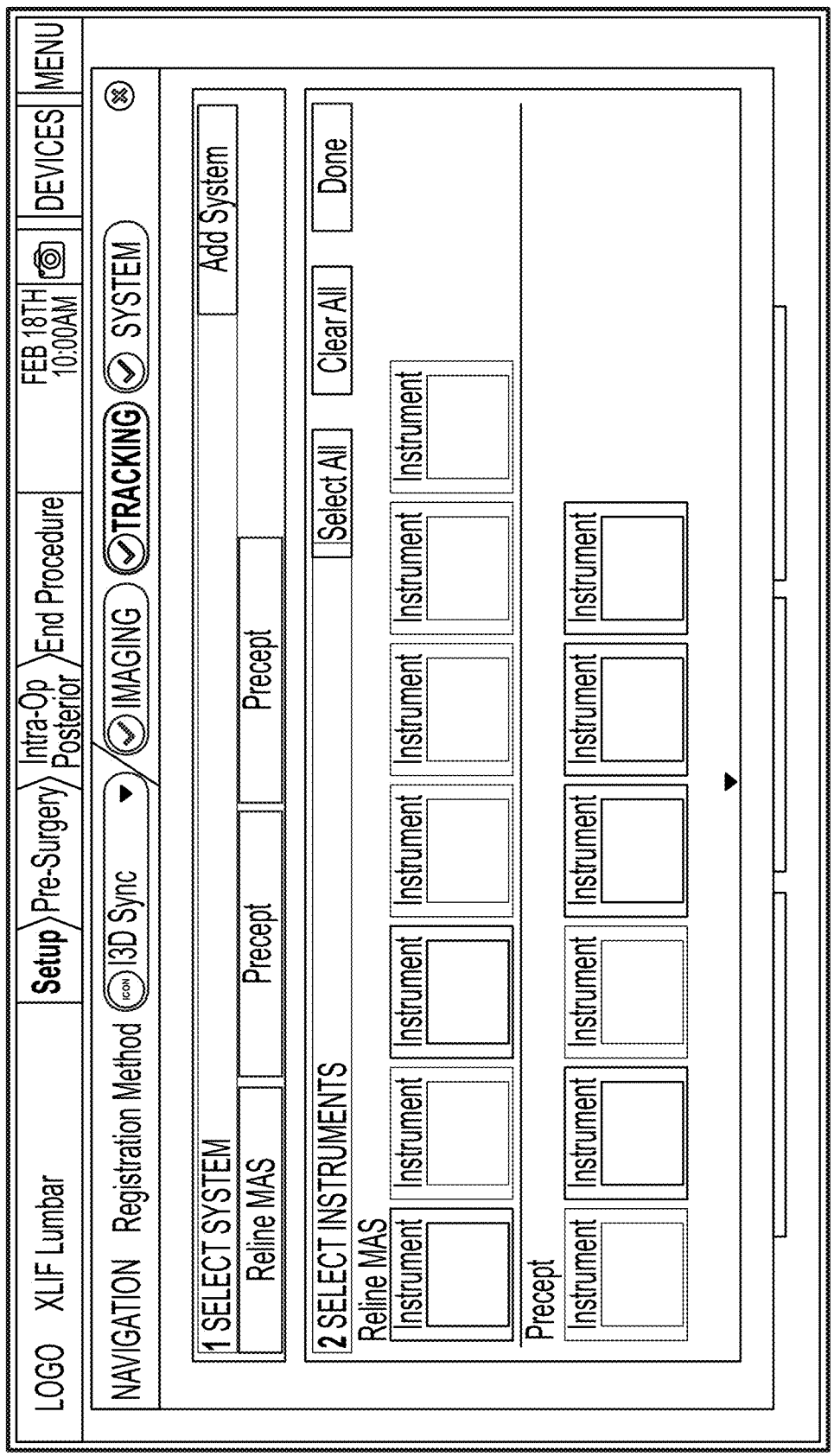
FIG. 29 illustrates an instrument setup menu screen displayed on a display screen according to an embodiment of the navigation system.
Figure 30:
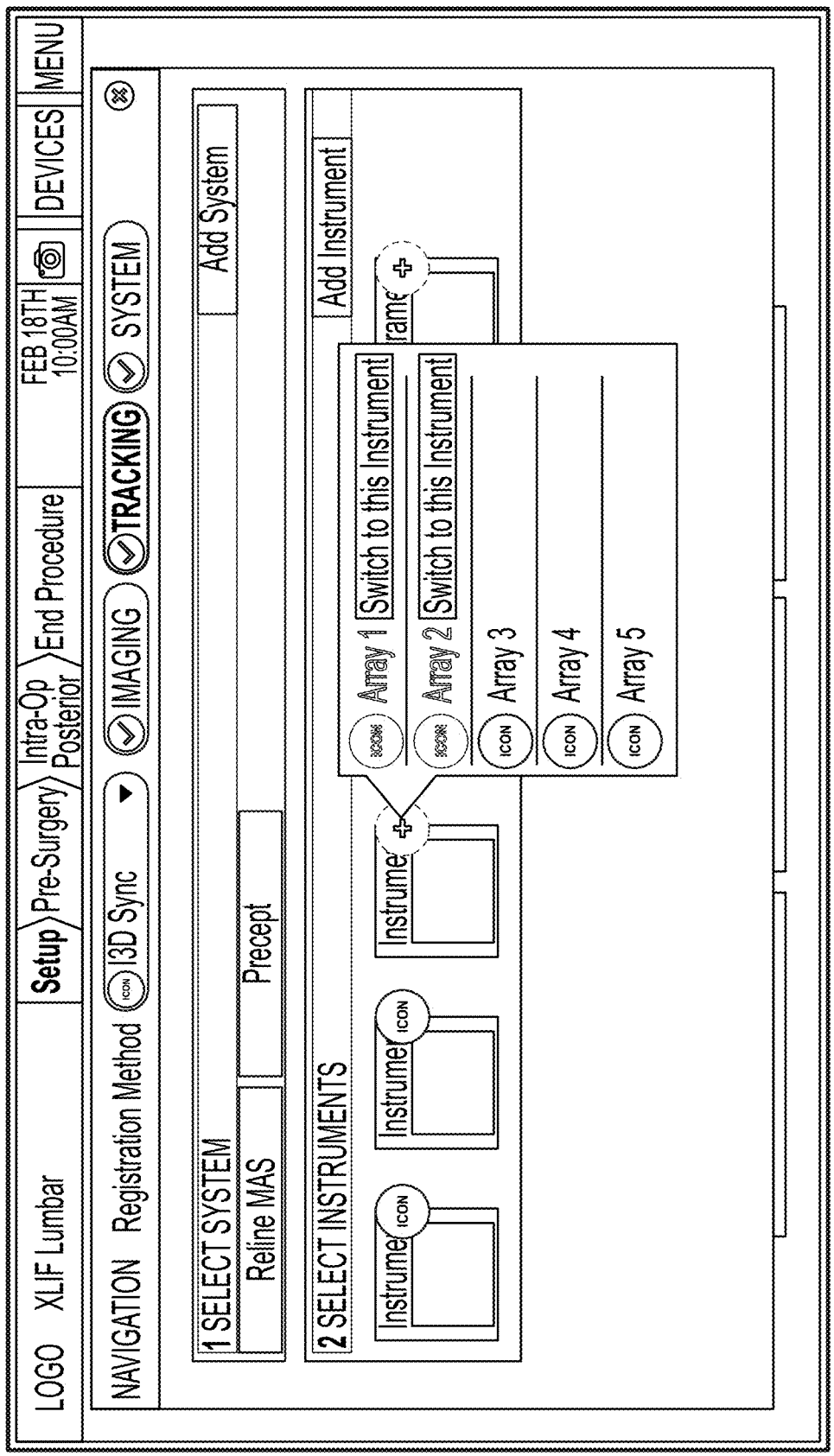
FIG. 30 illustrates an array assignment menu screen displayed on a display screen according to an embodiment of the navigation system.

The computer executable instructions may be configured to cause the display screen 16 to display an instrument setup menu (FIG. 29) and an array assignment menu (FIG. 30). The computer executable instructions may cause the system 10 to capture one or more images via the optical tracking system 32 and automatically recognize the array(s) 38. The system 10 may also utilize adapters for instruments 6, which allow the system 10 to recognize the instrument, identifying a first level describer (e.g., screwdriver for a screwdriver). The computer executable instructions may cause the display screen 16 to display a menu, such as a drop-down menu, so that the surgeon may select a final description for the instrument 6. Advantageously, this feature allows the surgeon to continue the operative workflow and seamlessly select navigated instruments 6.

Figure 31:
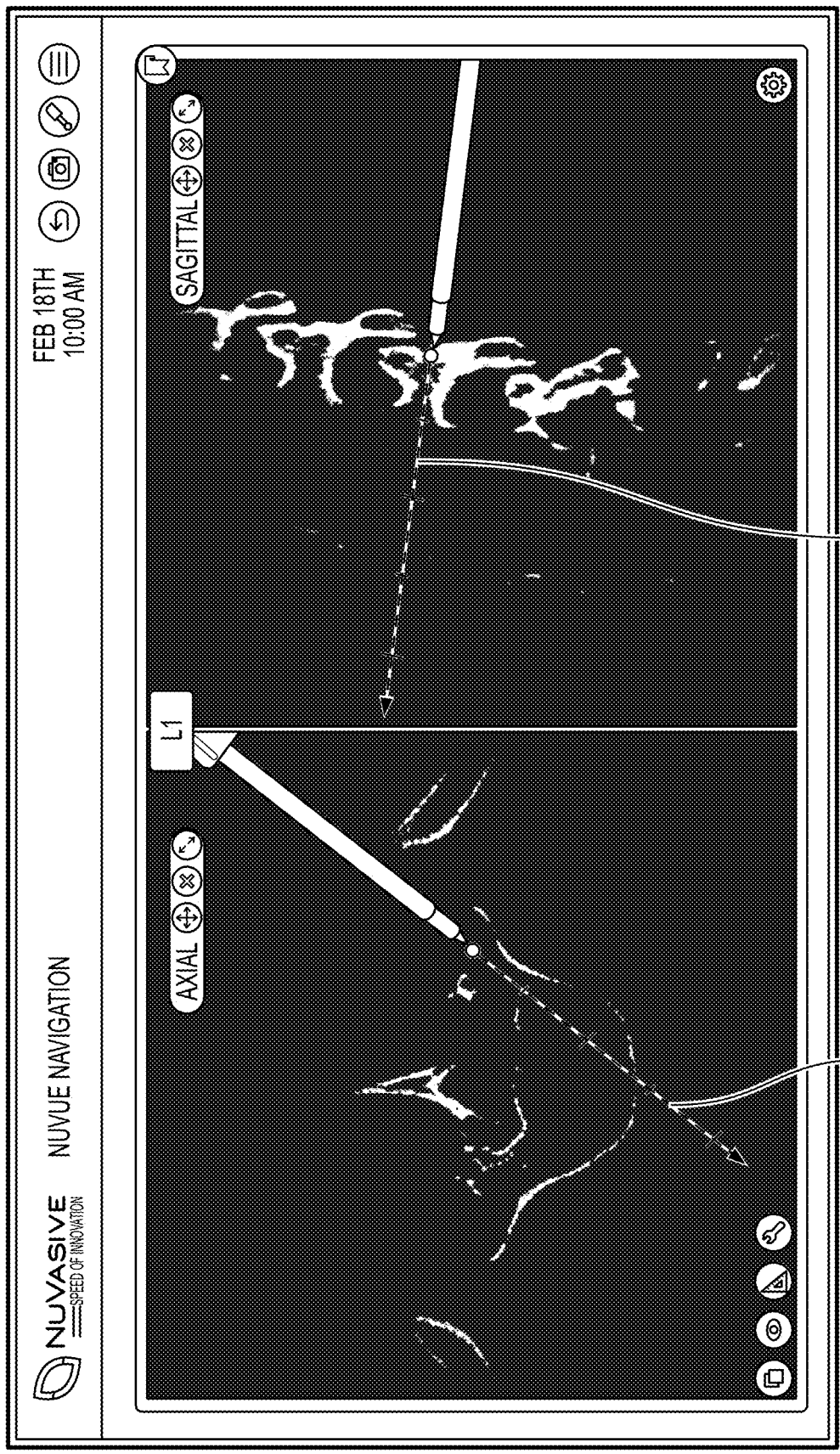
FIGS. 31-33 illustrate projected trajectory and screw screens displayed on a display screen according to an embodiment of the navigation system.
Figure 32:
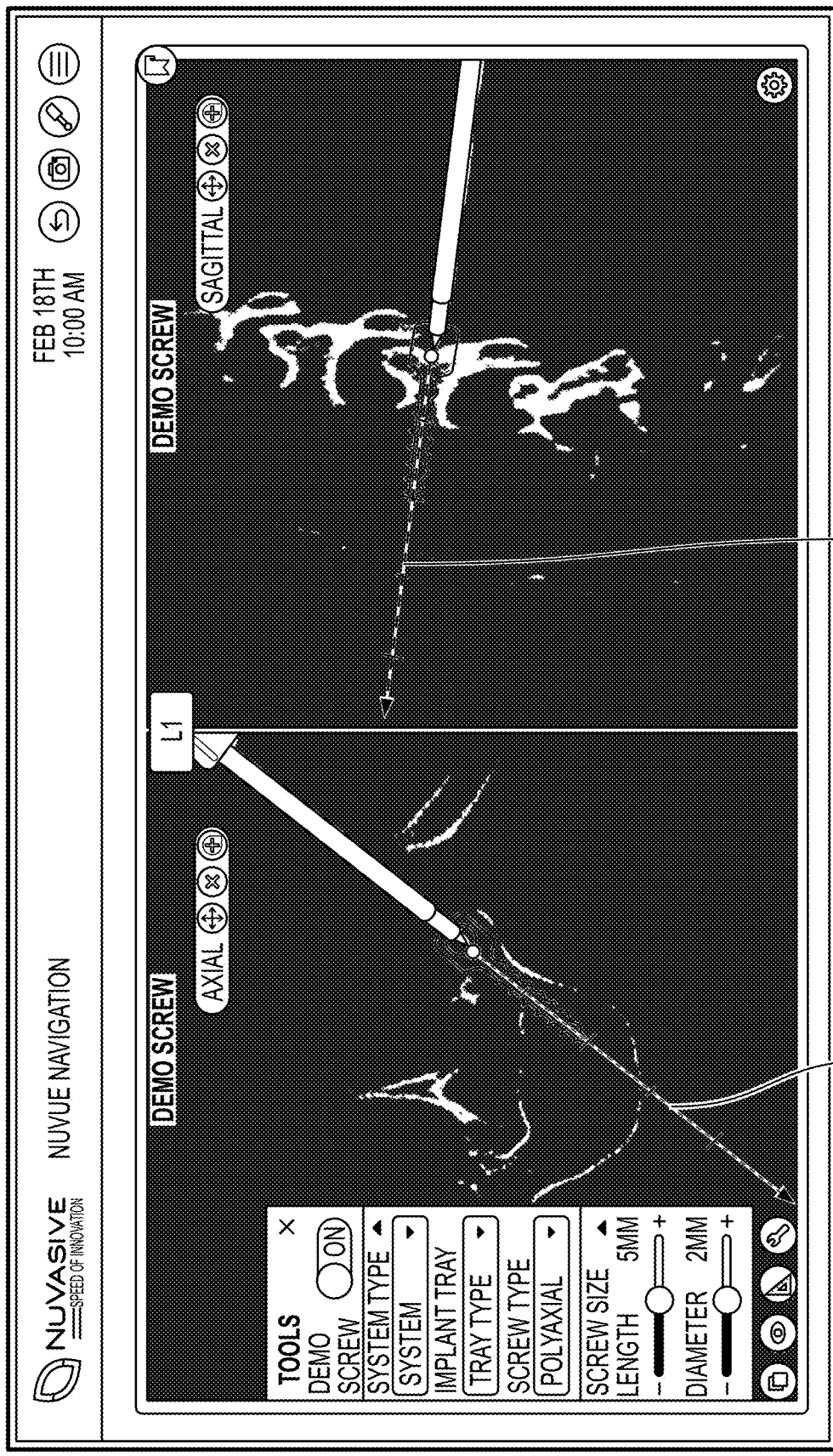
Figure 33:
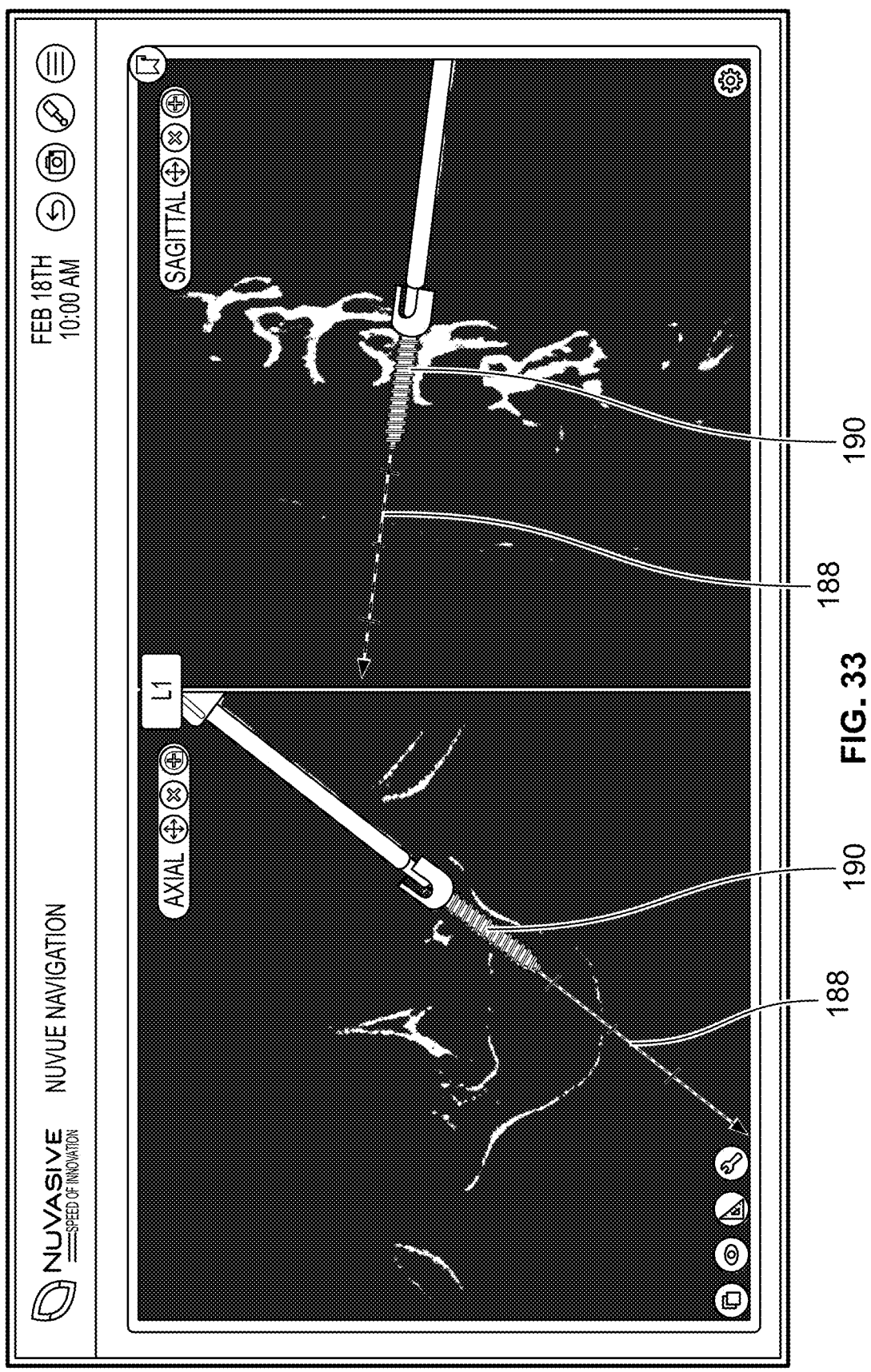

The computer executable instructions may be configured, particularly after registration and setup steps are completed, to cause representations of one or more surgical instruments to be overlaid on the 2D representation of the 3D image data set in real time. By way of example, the representation of the instrument can be an engineering model (such as computer-aided design model), a wire frame model, or a simple shape (such as a cylinder, rectangular, or block). The computer executable instructions may be configured to further generate a simulated trajectory 188 (such as of a pedicle screw) based on the location of the surgical instrument with respect to the anatomy and display the simulated trajectory 188 on the 2D representation on the display screen 16, as shown in FIGS. 31-33. As can be seen in FIG. 32, the computer executable instructions may be configured to cause a tool menu to display, in which various options such as system type, implant type, and screw type of the simulated trajectory 188 can be selected by the surgeon. The computer executable instructions can be configured to display a simulated implant 190 (e.g., pedicle screw) based on the simulated trajectory and surgeon inputs regarding the tool menu. Once the surgeon is satisfied with the trajectory and implant selection, the system 10 can be used to navigate the real-world implant 191 (not shown) to its intended location, preferably following the simulated trajectory 188 as depicted in FIG. 33. While a positioning of a pedicle screw is described here, it will be appreciated that the navigation system 10 can provide navigation information for any number of instruments and implants.

Figure 35A:
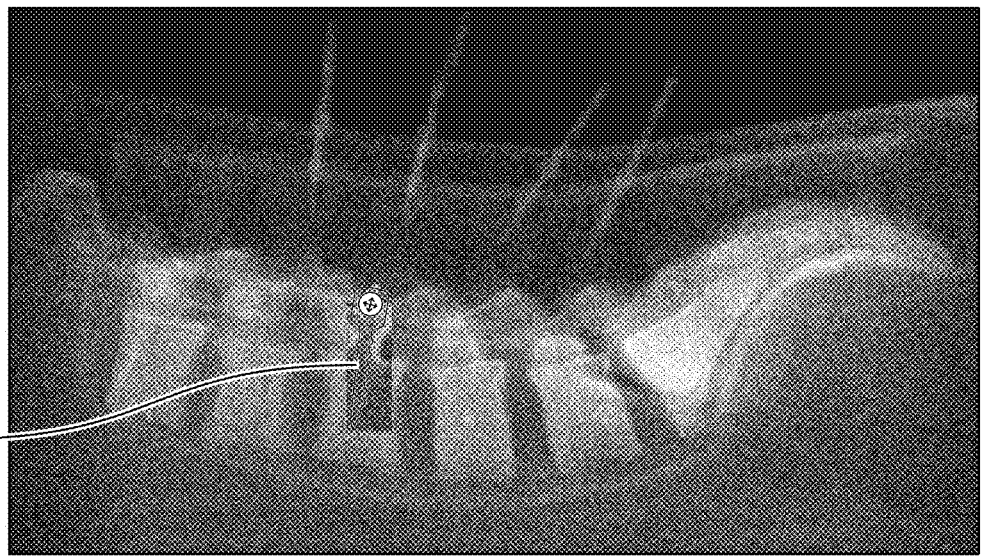
FIGS. 35A and 35B illustrate a bookmarked screw feature displayed on a display screen according to an embodiment of the navigation system.
Figure 35B:
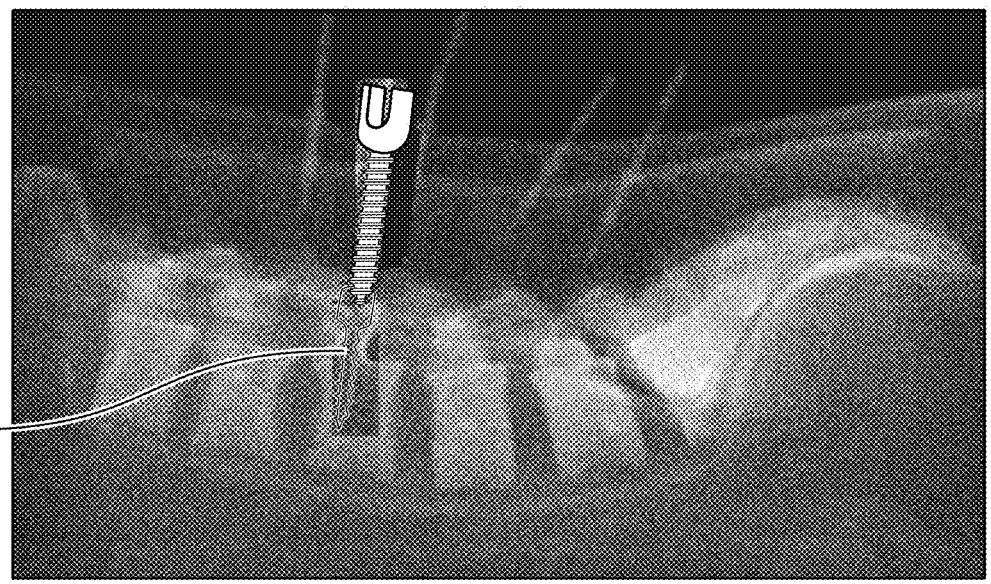

The system 10 may comprise computer executable instructions configured to generate a simulated bookmarked screw 192 and cause the simulated bookmarked screw 192 to be displayed to the surgeon on the display screen 16. This feature is beneficial when a surgeon desires to insert two screws into a single vertebra aligned from a particular perspective (e.g., lateral). Shown in FIGS. 35A and 35B, using the generated segmental DRR, as discussed above, the computer executable instructions may be configured to generate a simulated bookmarked screw to capture the final location of a first placed screw in a vertebrae. When the surgeon is ready to place the second screw in the vertebrae, the simulated bookmarked screw is displayed over the DRR image such that the surgeon has a reference for alignment for placing the second screw. The simulated screw may be depicted by a solid, opaque representation of a screw, an outline of a screw with a transparent body, or a line. The computer executable instructions may be configured to generate the simulated screws in views other than DRR, such as a 3D sagittal sliced view. FIG. 35A illustrates a simulated bookmarked screw in DRR of spine for reference, and FIG. 35B illustrates a screw being placed over the simulated bookmarked screw.

In an eighth aspect, the system 10 generates a 3D post-op simulated CT. According to this aspect, the last locations of the dynamically tracked vertebrae and the final position of each placed screw may be processed by the system 10, via computer executable instructions, to generate a post-op 3D view of the patient. Beneficially, this 3D view is an accurate depiction of the patient immediately following surgery, such that an additional 3D scan at the end of the surgery is not required, resulting in less radiation exposure to the patient and OR staff, and a savings of time (i.e., lower risk of morbidity and cost savings).

Figure 37:
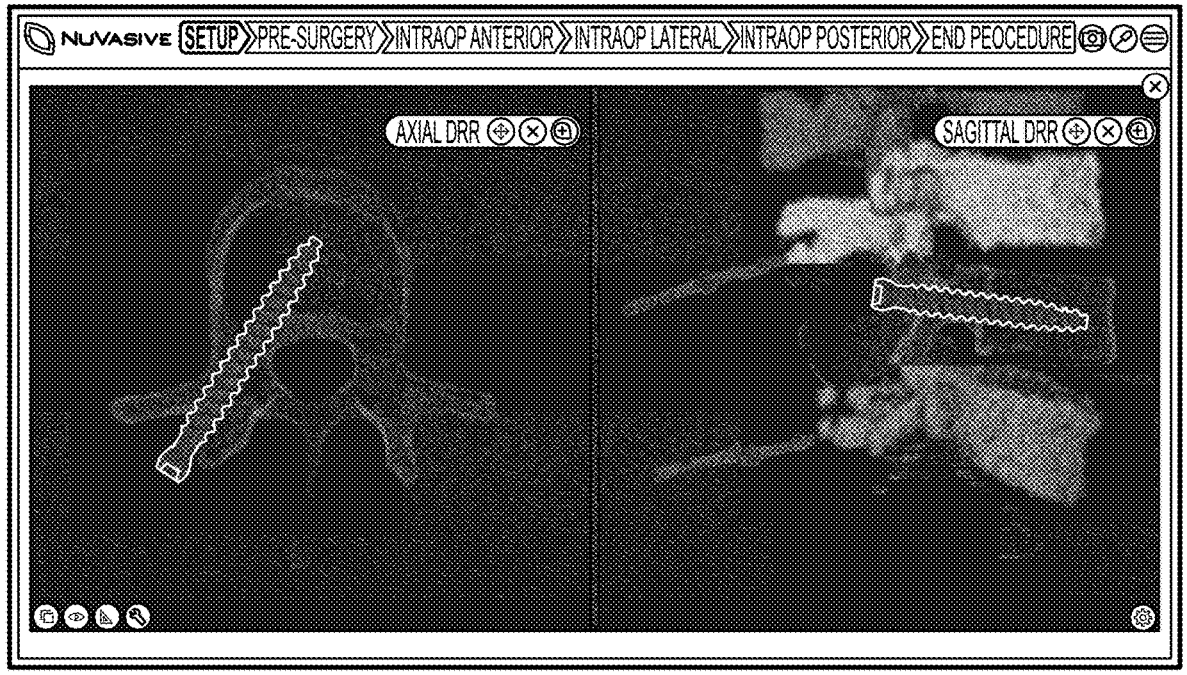
FIGS. 37 and 38 illustrate planned trajectories screens according to planned screws from pre-surgery displayed on a display screen according to another embodiment of the navigation system.
Figure 38:
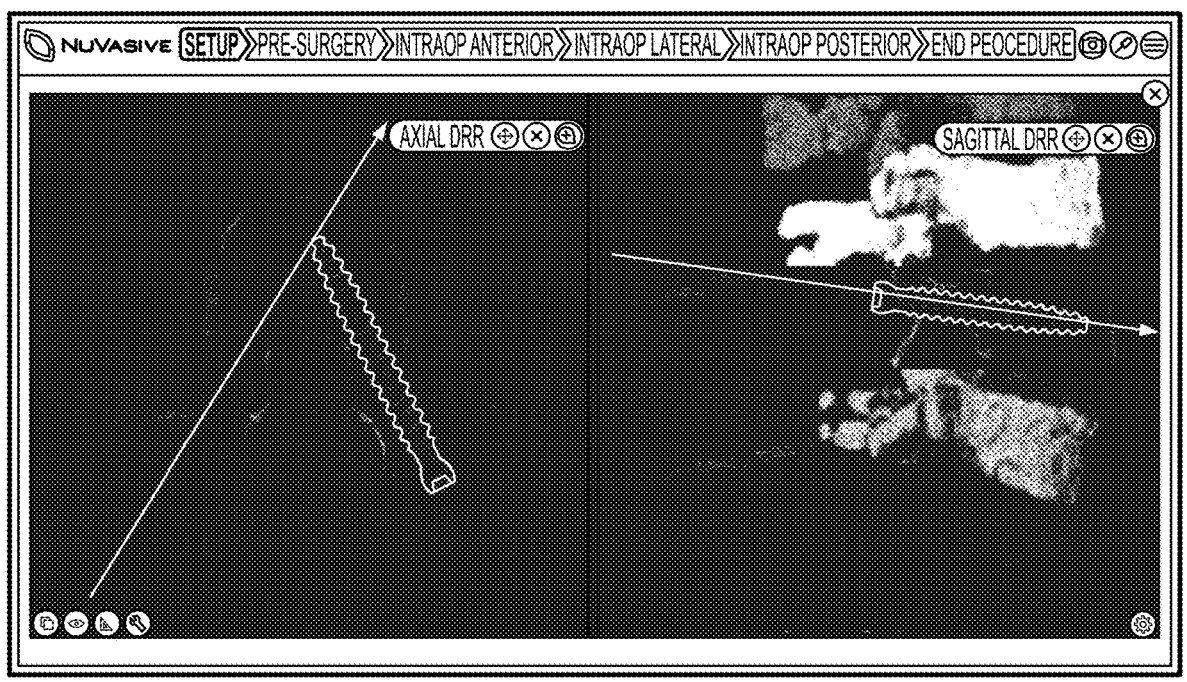
Figure 39:
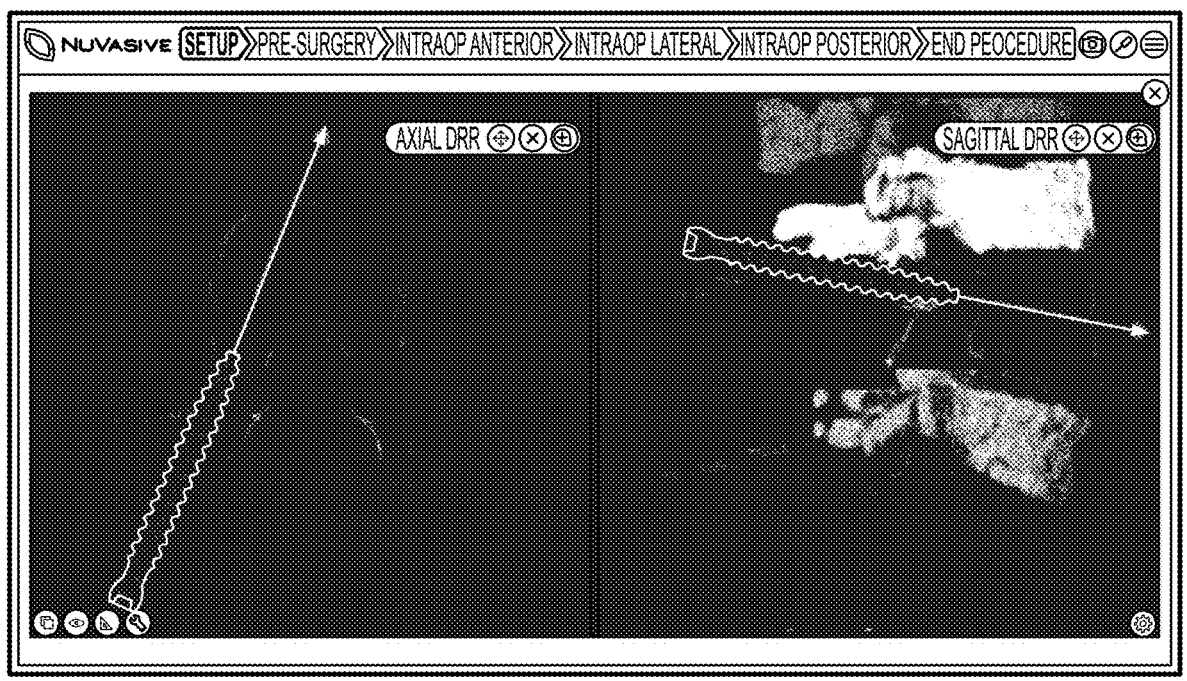
FIG. 39 illustrates a screen displaying the bookmarked screw feature displayed on a display screen according to another embodiment of the navigation system.

The segmentation steps described above are particularly advantageous in that they provide for additional viewing options for the surgeon. Referring to FIGS. 37-39, the GUI may display different view of the surgical site based on surgeon preference. Referring to FIG. 37, the GUI may display different views of the surgical site based on surgeon preference. In some embodiments, only registered vertebral bodies may display and may be shown in current orientation (not pre-op CT orientation) based on registration. The adjacent vertebrae levels may be displayed in their new locations as solid engineering files, such as 3D.stl or other format files, and all may be tracked relative to the single patient reference array 38 (above operative level). In some embodiments, a DICOM image may be navigated for only a vertebral body that is currently being worked on by the surgeon. The Axial DRR or tool view of the CT slice and Lateral DRR (either left or right half) or Sagittal tool view CT is shown in FIG. 37. FIG. 38 illustrates a displayed planned trajectories according to planned screws from pre-surgery, as discussed above, which may be toggled on and off by the surgeon. The bookmarked screw feature may also be toggled on and off by the surgeon, shown in FIG. 39. The GUI may include a "Hold New Trajectory" selection for providing the surgeon the option to adjust a new trajectory of the planned screw based on real world surgical conditions and the surgeon's professional medical judgment.

In an ninth aspect of the system 10, the system 10 receives images captured from more than one camera 34, 36 such that a first camera 34, 36 has a field of view of an operative area and a second camera 34, 36 has a field of view of a registration apparatus (e.g., a C-arm 194). The system 10 may include computer executable instructions configured to calibrate the relative position of the first camera 34, 36 and the second camera 34, 36 by referencing an array 38. The cameras 34, 36 may be provided together, for example in the camera base 37, or separately. The system 10 may perform dynamic calibration when the cameras 34, 36 are tracking in the same direction or tracking from opposite directions.

For example, the system 10 may include a first infrared camera 34 within the sterile operative field to capture images of and track arrays 38 in communication with the spine, as discussed above. The system 10 may include a second infrared camera 34 positioned outside of the sterile operative field which captures images of and track a registration device. The second infrared camera 34 may capture images of and track at least one of the arrays 38 tracked by the first infrared camera 34, but may not track all of the arrays 38 tracked by the first infrared camera 34 due to field of view obstructions. However, as discussed above, the system 10 may receive these data and generate 3D models and display 2D representations of the 3D models on the display screen 16.

In another example, the system 10 utilizes more than one camera 34, 36 may be used to capture and track more than one array 38 that is connected to the anatomical feature 4 that is a single rigid segment, such as the S 1/pelvis complex, that may be treated as a single structure.

In yet another illustrative use, during a lateral spine procedure, for example, an XLIF procedure, a first infrared camera 34 may capture and track spine tracker arrays 38 while a second infrared camera 34 captures and tracks the operative corridor and an array 38 affixed to the iliac crest. Although neither the first nor the second cameras 34 may track the same array 38, the system 10 may use the registered and segmented a single, rigid structure allowing the system to calculate an indirect correlation between cameras 34 during registration so that, while neither camera 34 needs to track a common array 38, the two cameras 34 transmit images and data that the system 10 can receive to generate a unified 3D view of the surgical area.

In a tenth aspect of the system 10, the system 10 is configured to generate an augmented reality. The system 10 may include at least three cameras 34, 36, where the first and second infrared cameras 34 may be used for tracking the marker arrays 42, which may be infrared markers 42, while the third visible light spectrum camera 36 is focused on the operative area. This at least three cameras 34, 36 configuration allows computer executable instructions of the system 10 to generate an accurate portrayal of the position of the virtual tool location and tracking markers 42 by superimposing images captured by the infrared cameras 34 and the visible light spectrum camera 36. This overlapping of the virtual representation and the visible element can be used for segmented vertebral bodies, too, when the vertebral bodies have arrays 38 connected to them. The surgeon can then view the vertebral bodies and the surgical instruments from either of the infrared cameras 34 with overlap from the visible camera 36 such that system 10 can, for example, visually guide the surgeon through a predetermined surgical plan entered into the system 10 by the surgeon. The system 10 may include a wearable camera and array assembly that can be worn by the surgeon such that the system 10 can display, for example through augmented reality glasses, a simulated vertebrae and instrument over the patient.

In an embodiment of the system 10, the system 10 is configured to use the augmented reality feature for trouble shooting problems with one or more arrays 38. For example, if an array 38 is blocked or contaminated, the system 10 may be configured to display highlighted pixels in the visible light spectrum to display the position of the blocked or contaminated array 38. The system 10 may overlay on the highlighted pixels a symbol, such as a colored ball, of the tracked infrared position of the markers 42 of the array 38. This troubleshooting feature enables a surgeon to understand whether a line of sight issue exists with the array 38 or whether one of the markers 42 is defective.

Especially advantageous is that the presently described navigation system 10 enables calibration of the navigation system 10 without interrupting surgical work plan flow. For example, the system 10 can display enlarged pixels where the system 10 has determined the position of an instrument so that the surgeon can confirm that the OR conditions are calibrated with, and accurately displayed by, the simulation. If calibration is necessary, then the system 10 can use image recognition, such as by capturing and receiving images from the visible light cameras 36, to recalibrate itself. The calibrating may be motion activated, activated by, and calibrated by, the surgeon rotating the instrument 6 in view of the visible light camera 36.

An instrument 6 may have many attachments, such as a screw driver. The system 10 may contain computer executable instructions configured to capture and track the instrument 6 and associated screw via the cameras 34, 36, and calculate the diameter and length of the screw. The computer executable instructions may be configured to display a virtual representation of the appropriate screw onto the display screen 16. The virtual representation of the screw may have a color code associated with screw size, such as screw diameter and screw length for easy visual identification by the surgeon.

In an eleventh aspect, the system 10 may perform redundant spine tracking. As discussed above, the system 10 may include more than one vertebral tracking array 38. The system 10 may track the movement of each of the arrays 38, and if the relative movement of the arrays 38 exceeds a predetermined value, the surgeon can select, through the GUI, to track a secondary array 38 as a reference or reregister the vertebral body.

Figure 34:
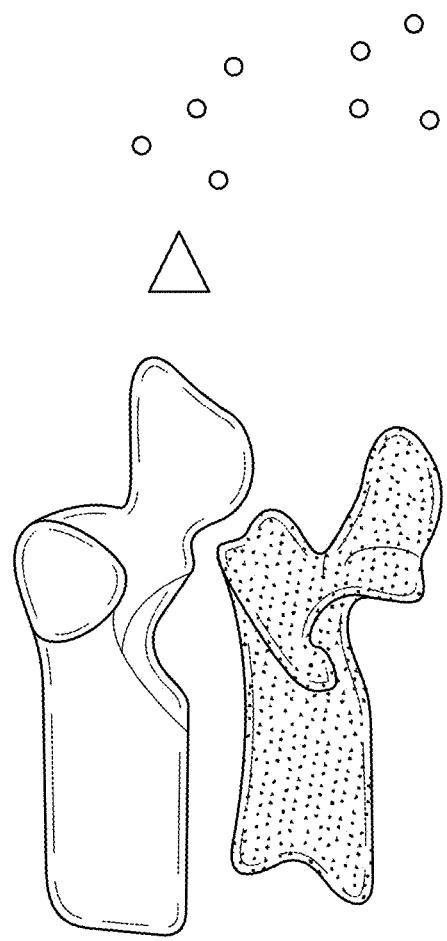
FIG. 34 illustrates a segmented vertebrae screen displayed on a display screen according to an embodiment of the navigation system.

In a twelfth aspect, the system 10 tracks individual segmented vertebral bodies and displays individual movement of the vertebral bodies. Referring to FIG. 34, each vertebra can be tracked by the system 10 through the spine pins 52 and arrays 38, as discussed above, and segmented from the rest of the vertebrae. The system 10 may include computer executable instructions that are configured to, based on the tracked and segmented vertebrae, generate and display simulated vertebrae that the surgeon can view and select in any 2D or 3D perspective moving relative to the adjacent vertebra. The simulated individual segments may contain respective radiographic data that can be viewable when system 10 receives instructions from the surgeon to slice open the simulated segments. The outer shell of the simulated segment can be given a specific color to assist the surgeon in differentiating one vertebra from adjacent vertebra also being tracked and simulated. The computer executable instructions may be configured to display and hide a background (i.e., non-vertebral body tissues). The background may be displayed as a differential color from the simulated vertebrae, such as black or another contrasting color to assist the surgeon by lighting the vertebra in which the surgeon is interested. When the background is hidden from the 3D view, a deformable transform matrix can be applied to display a simulation of how the soft tissues have stretched. If CT and MRI images have been merged, then this deformable transformation matrix can be used to highlight the soft tissues, including using further colors to highlight different tissue types. In some embodiments of the system 10, the computer executable instructions are configured to receive input from a surgeon to highlight a border of a particular vertebral body. This feature is particularly advantageous for operating on osteoporotic patients, and the surgeon would benefit from this aid in discerning the border of the vertebral body.

In a thirteenth aspect, the system 10 may be used in systems and methods for surgical planning and assessment of spinal deformity correction, as described in International Application Number PCT/US17/20491, which is incorporated by reference herein in its entirety. Advantageously, the navigation system 10 can be combined with the surgical planning and assessment such that computer executable instructions of the system 10 are configured to capture and track, at the start of the surgical procedure, the positions and orientations of the vertebrae. The computer executable instructions may be configured to receive images from the cameras 34, 36 and update spinopelvic parameters, or calculate the change in foraminal or canal volume to assess proper decompression, automatically to determine compliance with an optimized surgical plan. Advantageously, this automatic tracking and updating eliminates the need to interrupt surgical workflow to manually capture additional C-arm images.

In a fourteenth aspect, the system 10 may be utilized with rod bending software and machines, such as the BENDINI spinal rod bending system by NuVasive, Inc., described in U.S. Pat. No. 7,957,831 and U.S. Pat. No. 8,549,888, which are incorporated by reference herein in their entireties. As spinal rod bending systems use digitalized locations of screws to generate bend instructions, the present system 10 streamlines the process through the reference (i.e., the arrays 38) affixed to more than one vertebrae, the system 10, via the optical tracking system 32, can capture the location, the position, and orientation of the screw when the screw was inserted into the spine. Advantageously, this automates the digitization step in the workflow for the use of spinal rod bending systems and allows the virtual rod preview to be dynamically updated as the surgery progresses, as the vertebrae, implant, and instruments can continue to be automatically and continually tracked over the surgical procedure. Advantageously, once the rod is created using the spinal rod bending system, the system 10 can be configured to generate and simulate directional information to the surgeon to facilitate navigation of the rod insertion.

In a fifteenth aspect, the system 10 provides for integrated neuromonitoring when used in conjunction with intraoperative neuromonitoring, such as the NVM5 neuromonitoring platform by NuVasive, Inc. Neuromonitoring platforms are set forth in, for example, U.S. Pat. Nos. 8,538,539; 8,548, 579; 8,550,994; 8,556,808; 8,562,521; 8,591,432; 8,602, 982; 8,628,469; 8,634,904; 8,663,100; 8,672,840; 8,679, 006; 8,696,559; 8,708,899; 8,738,123; 8,747,307; 8,753, 271; 8,764,649; 8,768,450; 8,784,330; 8,821,396; 8,942, 801; 8,945,004; 8,956,283; 8,977,352; 8,989,866; and 9,037,250, which are hereby incorporated by reference in their entireties. The navigation features of the system 10 described herein may be integrated with EMG and free run activity, such that location of where EMG results occurred may be tracked and overlaid onto the 2D representations/ views of the spine generated by the navigation system 10. By way of example only, implanted devices such as pedicle screws can be colored red, yellow, or green based on their proximity to the bone-soft tissue interface, such that close or breached may display the implanted devices as red, near may display the implanted devices as yellow, and an acceptable margin of distance may display the implanted devices as green.

The foregoing description illustrates and describes the processes, machines, manufactures, and other teachings of the present disclosure. Additionally, the disclosure shows and describes only certain embodiments of the processes, machines, manufactures, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention (s) set forth herein.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. For example, any of the features of a particular example described herein may be used with any other example described herein without departing from the scope of the present invention. According to some embodiments, some or all of the surgical navigation systems, methods, and workflows described below can be used in conjunction with some or all of the systems, methods, and workflows described above.

The following is claimed:

1. A system for surgical navigation, comprising:
   a spine pin that includes:
      a first end section having a tri-lobular cross sectional profile and being configured to couple with an array and resist rotation relative to a coupled array;
      a second end opposite the first end and having a sharp tip configured to be inserted into an anatomical feature;
      a first radiographic glyph; and
      a second radiographic glyph separated from the first radiographic glyph by a distance;
   a first array including tracking markers, the first array being configured to be releasably secured with a vertebra via a connection with the first end section of the spine pin;
   at least one camera configured to track the first array; and
   a computer system including a processor, wherein the computer system is configured to:
      receive one or more camera images of the array from the at least one camera; and
      display a simulation of the first anatomical feature on a display screen.

2. The system of claim 1, wherein the first array includes hemispherical markers in six degrees of freedom.

3. The system of claim 1, further comprising a second array including tracking markers, the second array being configured to be releasably secured with a second anatomical feature.

4. The system of claim 1, wherein the first array comprises recesses, and wherein the markers are at least partially received in the recesses.

5. The system of claim 1, wherein the first array includes at least two oppositely facing surfaces, each surface having a plurality of markers.

6. The system of claim 5, wherein the markers include at least one marker disposed at a first surface of the first array and at least one marker disposed at a second surface of the first array.

7. The system of claim 1, wherein the first array is a 360 degree array.

8. The system of claim 1, wherein the first array is a 360 degree prismatic array.

9. The system of claim 1, further:
   comprising a C-arm coupled with a C-arm array mount including at least one C-arm array marker; and
   wherein the computer system is further configured to:
      receive one or more camera images of the at least one C-arm array marker from the at least one camera.

10. The system of claim 1, wherein the at least one camera includes an infrared camera and a visible light camera.

11. The system of claim 1, wherein the computer system is further configured to:
    receive one or more 3D images;
    recognize the first and second radiographic glyphs in the one or more 3D images;
    sense the tracking markers of the first array; and
    perform registration using the sensed tracking markers of the first array and the recognized first and second radiographic glyphs.

12. The system of claim 1, wherein the computer system is further configured to:
    receive one or more 3D images;
    recognize a geometric shape of the first and second radiographic glyphs separated by the distance in the one or more 3D images;
    sense the tracking markers of the first array; and
    perform registration using the sensed tracking markers of the first array and the recognized geometric shape.

13. The system of claim 1, wherein the distance is between 5 millimeters and 100 millimeters.

14. The system of claim 1, wherein the first radiographic glyph and the second radiographic glyph are coaxial with a length of the spine pin.

15. The system of claim 1, further comprising:
    a first glyph arm extending from the first radiographic glyph;
    a third radiographic glyph coupled to the first glyph arm;
    a second glyph arm extending from the second radiographic glyph; and
    a fourth radiographic glyph coupled to the second glyph arm.

16. The system of claim 1, further comprising:
    a depth limiter disposed between the second radiographic glyph and the second end.

17. The system of claim 1, wherein the tri-lobular cross sectional profile is rounded.

18. The system of claim 1,
    wherein the spine pin further includes a tool engagement feature; and
    wherein the system further comprises a spine pin inserter configured to couple with the tool engagement feature and facilitate insertion of the spine pin.

19. An apparatus comprising:
    a spine pin including:
       a first end section having a tri-lobular cross sectional profile and being configured to couple with an array and resist rotation relative to a coupled array;

a second end opposite the first end and having a sharp tip configured to be inserted into an anatomical feature;
a first radiographic glyph; and
a second radiographic glyph separated from the first radiographic glyph by a distance; and
a first array including tracking markers, the first array being configured to be releasably secured with a vertebra via a connection with the first end section of the spine pin.

* * * * *